(12) United States Patent
Hasan et al.

(10) Patent No.: US 9,828,622 B2
(45) Date of Patent: Nov. 28, 2017

(54) PHOTOACTIVATABLE ANTIMICROBIAL AGENTS AND THERAPEUTIC AND DIAGNOSTIC METHODS OF USING SAME

(75) Inventors: Tayyaba Hasan, Arlington, MA (US); Ulysses W. Sallum, Quincy, MA (US); Sarika Verma, Waltham, MA (US); Gerard Nau, Sharon, MA (US)

(73) Assignee: The General Hospital Corporation, Boston, MA (US)

( * ) Notice: Subject to any disclaimer, the term of this patent is extended or adjusted under 35 U.S.C. 154(b) by 1430 days.

(21) Appl. No.: 12/990,997

(22) PCT Filed: May 5, 2009

(86) PCT No.: PCT/US2009/002812
§ 371 (c)(1),
(2), (4) Date: Jan. 21, 2011

(87) PCT Pub. No.: WO2009/137062
PCT Pub. Date: Nov. 12, 2009

(65) Prior Publication Data
US 2011/0112059 A1    May 12, 2011

Related U.S. Application Data

(60) Provisional application No. 61/050,453, filed on May 5, 2008.

(51) Int. Cl.
| | | |
|---|---|---|
| *A61K 31/545* | (2006.01) | |
| *C12Q 1/34* | (2006.01) | |
| *C07D 501/52* | (2006.01) | |
| *C12Q 1/04* | (2006.01) | |
| *G01N 33/542* | (2006.01) | |
| *G01N 33/569* | (2006.01) | |

(52) U.S. Cl.
CPC .............. *C12Q 1/34* (2013.01); *C07D 501/52* (2013.01); *C12Q 1/04* (2013.01); *G01N 33/542* (2013.01); *G01N 33/56911* (2013.01); *G01N 2333/986* (2013.01)

(58) Field of Classification Search
CPC .......... C12Y 305/02006; A61K 31/545; A61K 31/43; A61K 9/0019; A61K 9/2004; C07D 501/20; C07D 501/52; C12Q 1/34; C12Q 1/04; G01N 33/542; G01N 33/56911; G01N 2333/986
USPC ............. 514/209; 530/300; 435/18; 540/219
See application file for complete search history.

(56) References Cited

U.S. PATENT DOCUMENTS

| | | | |
|---|---|---|---|
| 4,740,459 A | 4/1988 | Chen et al. | |
| 5,338,843 A | 8/1994 | Quante et al. | |
| 5,514,561 A | 5/1996 | Quante et al. | |
| 5,955,604 A | 9/1999 | Tsien et al. | |
| 6,462,070 B1 | 10/2002 | Hasan et al. | |
| 6,727,356 B1 | 4/2004 | Reed et al. | |
| 2004/0115207 A1 | 6/2004 | Irwin et al. | |
| 2008/0064025 A1 | 3/2008 | Su | |
| 2010/0016208 A1 | 1/2010 | Hasan et al. | |

FOREIGN PATENT DOCUMENTS

| | | | |
|---|---|---|---|
| EP | 09743049 | 5/2009 | |
| WO | 9703697 A2 | 2/1997 | |
| WO | WO 2005/071096 | 8/2005 | |
| WO | 2007059266 A2 | 5/2007 | |
| WO | WO 2007059226 A2 * | 5/2007 | ............. A61K 31/39 |

OTHER PUBLICATIONS

Cincotta et al, 1990, SPIE Proceedings, 1203, 202-209.*
Form PCT/US/210, WO, Sep. 4, 2001.
Form PCT/ISA/237, WO, Sep. 4, 2009.
Form PCT/IB326, WO, Nov. 18, 2009.
EPO Form 1503, EP, Dec. 16, 2011.
Xing Bengang et al: Cell-permeable near-infrared fluorogenic substrates for imaging beta-lactamase activity, Journal of the American Chemical Society, vol. 127, No. 12, Mar. 30, 2005, pp. 4158-4159.
Rovaldi C R et al: Photoactive porphyrin derivative with broad-spectrum activity against oral pathogens In Vitro, Antimicrobial Agents and Chemotherapy, American Society for Microbiology, Washington, DC, vol. 44, No. 12, Dec. 1, 2000, pp. 3364-3367.
Bouvier J et al: A fluorescent peptide substrate for the surface metalloprotease of Leishmania, Experimental Parasitology, New York, NY, vol. 76, No. 2, Mar. 1, 1993, pp. 146-155.
Zeina B et al: Killing of cutaneous microbial species by photodynamic therapy, British Journal of Dermatology, vol. 144, No. 2, Feb. 2001, pp. 274-278.
Xiang Zheng et al., Angewandte Chemie International Edition, vol. 48, No. 12, 2148-2151 (Mar. 2009).
Bengang Xing et al., Journal of the American Chemical Society, vol. 127, No. 12, pp. 4158-4159 (2005).
Draganescu et al., "Fhit-nucleotide specificity probed with novel fluorescent and fluorogenic substrates," Journal of Biological Chemistry, Feb. 18, 2000, 275(7): 4555-4560.
Erdem et al., " Rapid, low-cost fluorescent assay of-lactamase-derived antibiotic resistance and related antibiotic susceptibility," Journal of Biomedical Optics, SPIE—International Society for Optical Engineering, Oct. 2014, 19(10): 105007 (11 pages).
Extended European Search Report in European Application No. 15200112.9, dated May 18, 2016, 11 pages.
Gam, "Toward high throughput directed evolution of protease specificity using fluorescence activated cell sorting," Dissertation Presented to the Faculty of the Graduate School of the University of Texas at Austin, May 1, 2004, 187 pages.

(Continued)

*Primary Examiner* — Jeffrey S Lundgren
*Assistant Examiner* — Ibrahim D Bori
(74) *Attorney, Agent, or Firm* — Fish & Richardson P.C.

(57) ABSTRACT

The present invention provides photosensitizer compounds for use in detecting beta-lactamase activity. Methods and kits that utilize the photosensitizer compounds of the invention for the detection of, quantitation of, and classification or typing of microbial beta-lactamases.

4 Claims, 16 Drawing Sheets

(56) References Cited

OTHER PUBLICATIONS

Jiang and Mellors, "Membrane protein proteolysis assayed by fluorescence quenching: assay of O-sialoglycoprotein endopeptidase," Analytical Biochemistry, May 1988, 259(1): 8-15.
Papanicolaou et al., "Dicrimination of extended-spectrum beta-lactamases by a novel nitrocefin competition assay," Antimicrobial Agents and Chemotherapy, Nov. 1990, 34(11): 2484-2192.
Ulrich et al., "The Chemistry of fluorescent bodipy dyes: versatility unsurpassed," Angew Chemi Int Ed, Feb. 2008, 47(7): 1184-1201.

* cited by examiner

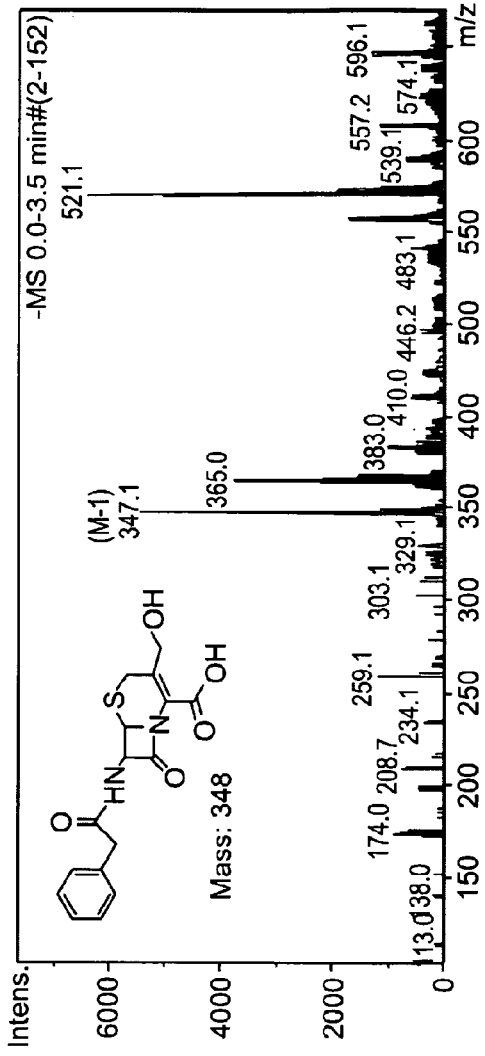
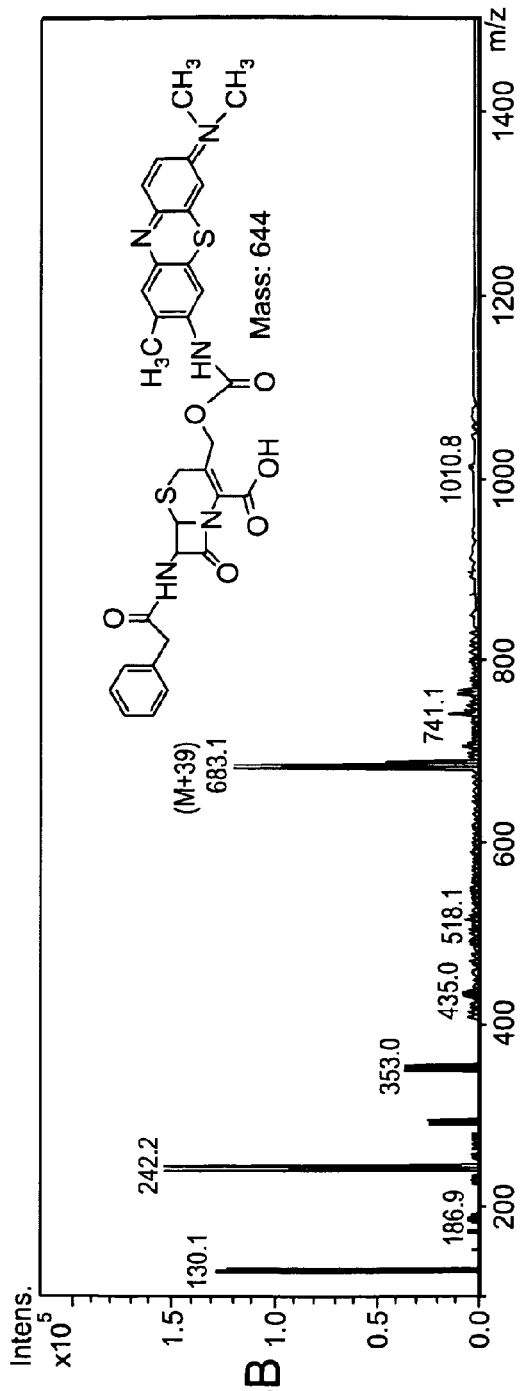
FIG. 3A
FIG. 3B

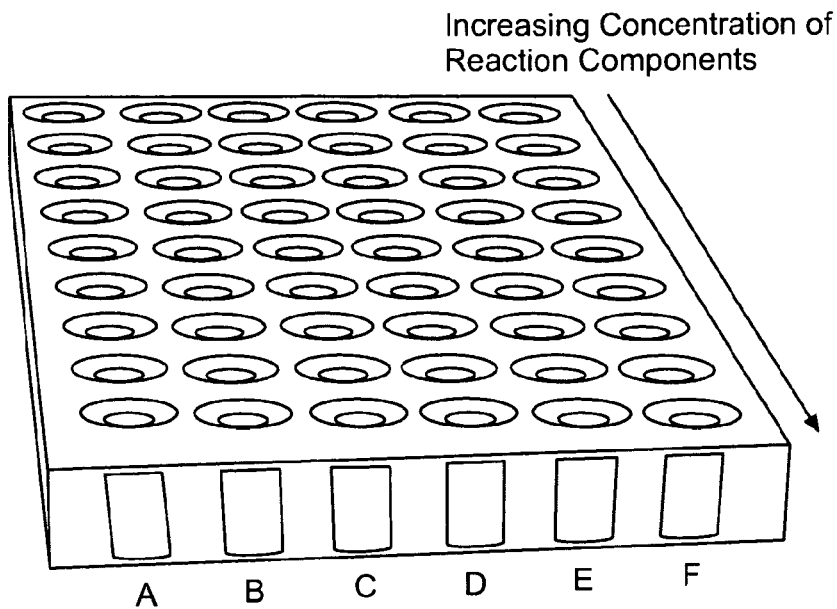

Increasing Concentration of Reaction Components

- A-β-LEAPP and Sample
- B-β-LEAPP and Sample + Competitor β-Lactam 1 (ie. Ceftazidime)
- C-β-LEAPP and Sample + Competitor β-Lactam 2 (ie. Cefotaxime)
- D-β-LEAPP and Sample + Enzyme Inhibitor 1 (ie. EDTA)
- E-β-LEAPP and Sample + Enzyme Inhibitor 2 (ie. Clavulanic Acid)
- F-Sample Alone

**Great Initial Velocity = Greater Fluorescence Emission
Ratios of Initial Velocities Different for Enzymes**

FIG. 12

**Comparison of Inhibition Constants for Pure §-Lactamase & Bacterial Suspensions, with Inhibition Profiles & Minimum Inhibitory Concentrations of *Bacillus cereus* inhibition profiles of panel of §-lactams for *B. cereus*

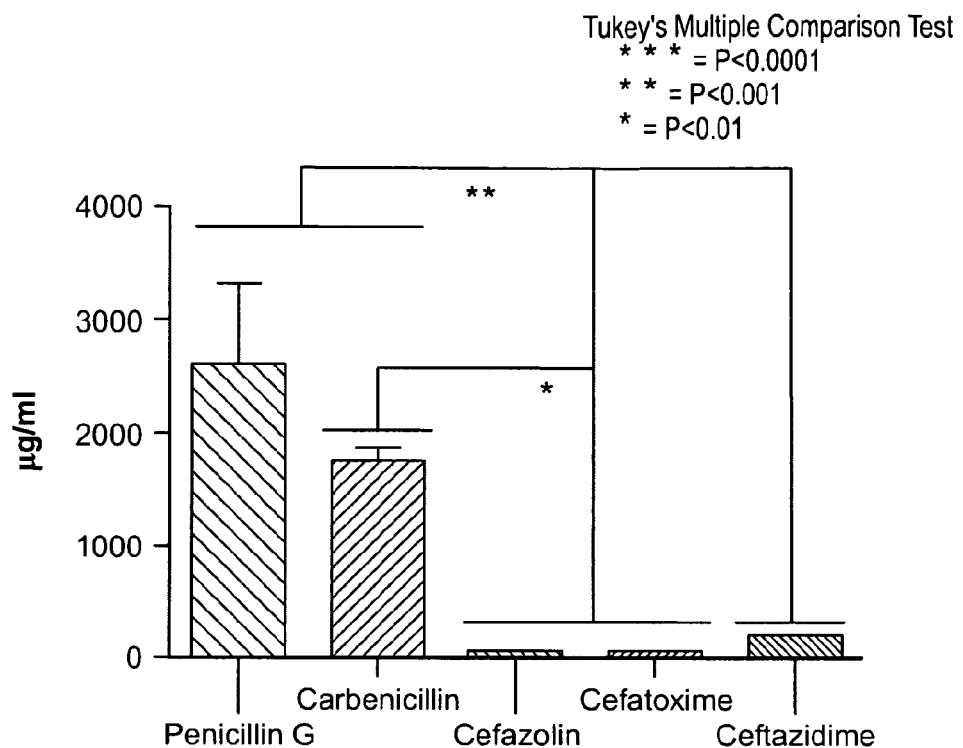
MICs of panel of §-lactams for *B- cereus*. Amoxicillin, clavulanic acid and ampicillin did not inhibit the growth of B. cereus and were not included in (c.) and (d.). Statistical significance was determined via Tukey's multiple comparison test using Graphpad Prism 5. Horizontal bars connected by solid intersections indicate significant difference
FIG. 13D

PHOTOACTIVATABLE ANTIMICROBIAL AGENTS AND THERAPEUTIC AND DIAGNOSTIC METHODS OF USING SAME

CROSS-REFERENCE TO RELATED APPLICATIONS/PATENTS & INCORPORATION BY REFERENCE

This application is the U.S. national phase, pursuant to 35 U.S.C. §371, of PCT international application Sera No. PCT/US2009/002812, filed May 5, 2009, designating the United States and published in English on Nov. 12, 2009 as publication WO 2009/137062 A3, which claims priority to U.S. Provisional Application Ser. No. 61/050,453, filed May 5, 2008. The entire contents of the aforementioned patent applications are incorporated herein by this reference.

This application is also related to International application No. PCT/US2006/044369, filed Nov. 15, 2006, and to U.S. Provisional application Ser. No. 60/736,917, filed Nov. 15, 2005. All of the aforementioned Provisional and International patent applications are hereby expressly incorporated herein by reference in their entireties.

Any and all references cited in the text of this patent application, including any U.S. or foreign patents or published patent applications, International patent applications, as well as, any non-patent literature references, including any manufacturer's instructions, are hereby expressly incorporated herein by reference.

GOVERNMENT SUPPORT

This invention was made with Government support under Grant No. FA9550-04-1-0079 awarded by the Air Force Office of Scientific Research. The Government has certain rights in this invention.

BACKGROUND OF THE INVENTION

The widespread use of antimicrobial chemotherapeutics has had the inevitable consequence of the emergence of antibiotic-resistant pathogens, which has continualy prompted further development and design of new drugs to combat such organisms. Today, more than 70% of the bacteria associated with nosocomial infections in the United States are resistant to one or more of the drugs previously used to treat them. Drug resistance in bacteria—which is not limited to the U.S. but extends throughout the world—includes, for example, the worldwide emergence of *Haemophilus* and gonococci that are resistant to β-lactam antibiotics (e.g., penicillin), methicillin-resistant *Staphylococcus aureus*, multiple-drug resistant *S. aureus* with high-level resistance to vancomycin, various isolated strains of *Pseudomonas* and *Enterobacter* that are resistant to all available antibiotics, and multiple-drug resistant strains of *Mycobacterium tuberculosis*.

While society increasingly has recognized the negative consequences of the misuse of antibiotics, overuse and overprescribing of antibiotics continue to be widespread throughout the world, driven by diagnostic uncertainties, demands by patients, and physicians' lack of time to effectively evaluate patients. Although reducing inappropriate antibiotic use is thought to be the best way to curb resistance, physicians must generally be more selective and prudent in their use and prescribing of antibiotics so that the gains in the battle against infectious diseases over the past century are not lost. The rampant spread of antibiotic resistances mandates a more responsible and sensible approach to antibiotic use.

The β-lactam antibiotics (e.g., β-lactam ring-containing antibiotics, such as, penicillins, cephalosporins, or carbapenems, which inhibit bacterial cell wall synthesis) are a particularly prevalent and important class of antibiotics that are widely prescribed for a large variety of gram-negative and gram-positive infections. Consequently, widespread resistance has emerged. One particularly important mechanism of microbial resistance to the β-lactam antibiotics stems generally from the production of enzymes known as the β-lactamases or cephalosporinases, which enzymatically cleave β-lactam antibiotics thereby causing their inactivation. This type of resistance can be encoded on the chromosome or on extra-chromosomal elements (e.g. bacterial plasmids), which can be transferred horizontally to other bacteria. Other modes of resistance to β-lactam antibiotics also include acquisition of penicillin-binding proteins and decreased entry and/or active efflux of drugs through membrane efflux pump systems.

Clinical detection of β-lactamases represents a key step in the management of antibiotic therapy of bacterial infections. In particular, the amount of beta-lactamase activity and the substrate specificity of that activity are important considerations in determining the appropriate antibiotic therapy for patients suffering from drug resistant bacterial infections.

β-lactam susceptibility and resistance can be detected and/or measured in a variety of ways. For example, Kirby-Bauer antibiotic testing uses antibiotic-impregnated discs to test whether particular bacteria are susceptible to specific antibiotics. A known quantity of bacteria is grown on agar plates in the presence of thin wafers containing relevant antibiotics, such as penicillin or ampicillin. If the bacteria are susceptible to the antibiotics, a zone of inhibition forms around the diffusion zone of the wafers. The size of the zone is correlated to the minimum inhibitory concentratin ("MIC") of antibiotic for that bacteria. In this way, health care providers are able to choose appropriate antibiotics to combat a particular infection.

In addition, agar dilution methods and broth microdilution methods can be used. Many of these labor-intensive and time-consuming methods often fail to detect drug resistance in certain gram-negative bacteria and all require a pregrowth step in which the strain is grown in broth or on a plate under conditions in which the organism is exposed only to the inducing antibiotic. This step is followed by a challenge in the presence of an indicator antibiotic or direct assay of enzymatic activity. These approaches require pure culture inoculation and growth, and involve up to 24 hours of incubation.

Chromogenic substrates have also been used, which, when cleaved by bacterial beta-lactamases, produce a colorimetric change that can be detected or measured. Examples of such substrates include, for example, nitrocefin and centa, which are known in the art. Nitrocefin is sold in the form of impregnated paper discs, which, when placed in the vicinity of a bacterial culture producing β-lactamase, results in the development of a pink color. Although this method provides a rapid qualitative detection (i.e., yes/no), it does not provide any information regarding the relative amount of enzymatic activity or any insight into the type of beta-lactamase activity, and, thus, cannot be used alone to determine the appropriate course of therapy in a clinical setting.

As can be seen, currently available methods for detecting and evaluating beta-lactamase activity and resistance to beta-lactam antibiotics suffer a number of drawbacks. In particular, such methods, while providing qualitative information (yes/no) about drug resistance, are time-consuming and do not easily facilitate the quantitative measurement of enzyme activity or determination of enzyme type or substrate characteristics—which constitute highly valuable information for determining an appropriate strategy for antimicrobial therapy.

Accordingly, new methods and compositions for detecting and evaluating beta-lactamase activity, which are more sensitive, rapid and easier to perform, and which reliably and expediently provide both qualitative and quantitative information as to the activity and/or substrate specificity of a beta-lactamase, would represent an advance in the art.

SUMMARY OF THE INVENTION

The present invention provides methods and compositions that can be advantageously utilized for the qualitative and/or quantitative detection of beta-lactamase activity, which are more sensitive, rapid and easier to perform than prior methods. The methods and compositions of the invention can also be used to evaluate the substrate specificity of a beta-lactamase activity from any sample containing a beta-lactamase enzyme, including, for example, bodily fluids, cells or tissues carrying an infection with a pathogenic beta-lactamase-producing bacterium. The invention advantageously provides a method to determine effective and suitable strategies for the treatment of bacterial infections using appropriate regimes of antibiotics, which are effective against target organisms.

In one aspect, the present invention provides a photosensitizer composition, wherein the composition comprises at least one benzophenothiazinium chloride (EtNBS) photosensitizer conjugated to a cephalosporin linker or fragment thereof. The composition can include two benzophenothiazinium chloride (EtNBS) photosensitizers conjugated to a cephalosporin linker (L) or fragment thereof. The photosensitizer can be bound at the 3' position of a cephalosporin. In one aspect, the photosensitizers are quenched when the linker is uncleaved.

In another aspect, the present invention provides a photosensitizer composition according to formula I:

wherein L is a cephalosporin linker or fragment thereof, X is benzophenothiazinium chloride (EtNBS) and X' is benzophenothiazinium chloride (EtNBS), wherein the photosensitizers are in a quenched state when L is uncleaved.

The photosensitizer composition can further include a targeting moiety, which can target the composition to a pathogen or a host cell, e.g., a macrophage, infected with a pathogen. The targeting moiety can include a liposome, a peptide, or a small anti-microbial peptide or an active fragment or analog thereof.

The photosensitizer composition of the invention can also include one or more binders effective to quench photoactivation of the benzophenothiazinium chloride (EtNBS). The binder can be a fluorophore or a photosensitizer in various aspects.

In still another aspect, the photosensitizer composition of the invention can further include a backbone coupled to the two benzophenothiazinium chloride (EtNBS) and one or more binders effective to quench photoactivation, wherein the binders are connected to the backbone through the linker. The backbone can include a targeting moiety and can be a polyamino acid (e.g., polylysine) in one aspect.

The L (or linker) can include a penicillin, such as, benzthine penicillin, benzylpenicillin (penicillin G), phenoxymethylpenicillin (penicillin V), procaine penicillin, oxacillin, methicillin, dicloxacillin, flucloxacillin, temocillin, amoxicillin, ampicillin, co-amoxiclav, carboxypenicillins, ureidopenicillins, azlocillin, carbenicillin, ticarcillin, mezlocillin, piperacillin, or any fragment or derivative of the above. The L can also include a cephalosporink, such as, (cephacetrile), Cefadroxil (cefadroxyl; Duricef®), Cefalexin (cephalexin; Keflex®), Cephaloglycin, Cefalonium (cephalonium), Cefaloridine (cephaloradine), Cefalotin (cephalothin; Keflin®), Cefapirin (cephapirin; Cefadryl®), Cefatrizine, Cefazaflur, Cefazedone, Cefazolin (cephazolin; Ancef®, Kefzol®), Cefradine (cephradine; Velosef®), Cefroxadine, Ceftezole, Cefaclor (e.g., Ceclor®, Distaclor®, Keflor®, Raniclor®), Cefonicid (e.g, Monocid®), Cefprozil (e.g., cefproxil; Cefzil®), Cefuroxime (e.g., Zinnat®, Zinacef®, Ceftin®, Biofuroksym®), Cefuzonam, Cefinetazole, Cefotetan, Cefoxitin, Carbacephems (e.g., loracarbef (Lorabid®)), Cephamycins (e.g., cefbuperazone, cefmetazole (Zefazone®), cefminox, cefotetan (Cefotan®), cefoxitin (Mefoxin®)), cefotetan or cefoxitin, Cefcapene, Cefdaloxime, Cefdinir (Omnicef®), Cefditoren, Cefetamet, Cefixime (Suprax®), Cefmenoxime, Cefodizime, Cefotaxime (Claforan®), Cefpimizole, Cefpodoxime (Vantin®, PECEF), Cefteram, Ceftibuten (Cedax), Ceftiofur, Ceftiolene, Ceftizoxime (Cefizax®), Ceftriaxone (Rocephin®), Cefoperazone (Cefobid), Ceftazidime (Fortum®, Fortaz®), or Oxacephems (e.g. latamoxef), cefepime (Maxipime®), cefclidine, cefluprenam, cefoselis, cefozopran, cefpirome, cefquinome, cefpirome, or a fragment of derivative of any of the above composition further comprises a targeting moiety.

In another aspect, the present invention provides a method for detecting a beta-lactamase activity in a sample, comprising the steps of: contacting the sample with a photosensitizer composition comprising two or more photosensitizers that are conjugated to a linker, wherein the linker comprises a cleavage site for a beta-lactamase and wherein the photosensitizers are quenched when the cleavage site is intact but unquenched when the cleavage site is hydrolyzed; and detecting cleavage of said linker, wherein cleavage of said linker is indicative of a beta-lactamase activity in the sample.

In still a further aspect, the present invention provides a method for determining the substrate specificity of a beta-lactamase enzyme in a sample, comprising: contacting the sample with a photosensitizer composition comprising two photosensitizers that are conjugated to a linker, wherein the linker comprises a cleavage site for a beta-lactamase enzyme and wherein the photosensitizers are quenched when the cleavage site is intact but unquenched when the cleavage site is cleaved; and determining whether the linker is cleaved, wherein cleavage of the linker indicates the linker is a substrate of the beta-lactamase enzyme.

The invention also provides, in another aspect, a method of typing a beta-lactamase enzyme in a sample, comprising: performing a competitive reaction comprising the steps of (a) contacting the sample with a photosensitizer composition comprising two photosensitizers that are conjugated to a linker, wherein the linker comprise a cleavage site for a beta-lactamase and wherein the photosensitizers are in a quenched state; (b) cleaving the linker to dequench the photosensitizers; (c) light-activating the composition to produce a fluorescence signal; and (d) quantifying the fluorescence signal with a detector to obtain a result, said competitive reaction being performed in the presence of a competing beta-lactam antibiotic; and comparing the result of the competitive reaction to a standard to type the beta-lactamase. The standard can be determined by performing a non-competitive reaction comprising the steps of (a) contacting the sample with a photosensitizer composition comprising two photosensitizers that are conjugated to a linker, wherein the linker comprise a cleavage site for a beta-lactamase and wherein the photosensitizers are in a quenched state; (b) cleaving the linker to dequench the photosensitizers; (c) light-activating the composition to produce a fluorescence signal; and (d) quantifying the fluorescence signal with a detector to obtain a standard.

In certain aspects, the step of detecting an unquenched photosensitizer can include detecting a signal produced by the unquenched photosensitizer. The signal can be a fluorescence emission induced by illuminating the unquenched photosensitizer with an excitation wavelength.

In other aspects, the sample can be a biological sample isolated from an infection in a subject, such as a mammal, including a human. The infection can be caused by an antibiotic-resistant pathogen, which can be a Gram (−) bacterium or Gram (+) bacterial pathogen.

In some aspects, the antibiotic-resistant pathogen can be a *Staphylococcus, Enterococcus, Enterobacter, Escherichia, Haemophilus, Neisseria, Klebsiella, Pasteurella, Proteus, Pseudomonas, Streptophomonas, Burkholderia, Acinetobacter, Serratia,* or *Salmonella* spp.

The antibiotic-resistant pathogen can also be a *Staphylococcus aureus, Staphylococcus epidermis, Enterococcus faecalis, Enterococcus faecium, Escherichia coli, Haemophilus influenzae, Neisseria gonorrhea, Klebsiella pneumoniae, Pasteurella multocida, Proteus mirabilis, Pseudomonas aeruginosa, Stenotrophomonas maltophilia, Burkholderia cepacia, Acinetobacter baumannii, Enterobacter aerogines, Enterobacter cloacae, Serratia marcescens, Salmonella enterica,* or *Salmonella typhimurium*.

In certain aspect, the photosensitizer can be a porphryin, including a porfimer sodium, hematoporphyrin IX, hematoporphyrin ester, dihematoporphyrin ester, synthetic diporphyrin, O-substituted tetraphenyl porphyrin, 3,1-meso tetrakis porphyrin, hydroporphyrin, benzoporphyrin derivative, benzoporphyrin monoacid derivative, monoacid ring derivative, tetracyanoethylene adduct of benzoporphyrin, dimethyl acetylenedicarboxylate adduct of benzoporphyrin, δ-aminolevulinic acid, benzonaphthoporphyrazine, naturally occurring porphyrin, ALA-induced protoporphyrin IX, synthetic dichlorin, bacteriochlorin tetra(hydroxyphenyl) porphyrin, purpurin, octaethylpurpurin derivative, etiopurpurin, tin-etio-purpurin, porphycene, chlorin, chlorin $e_6$, mono-1-aspartyl derivative of chlorin $e_6$, di-1-aspartyl derivative of chlorin $e_6$, tin(IV) chlorin $e_6$, meta-tetrahydroxyphenylchlorin, chlorin $e_6$ monoethylendiamine monamide, verdin, zinc methylpyroverdin, copro II verdin trimethyl ester, deuteroverdin methyl ester, pheophorbide derivative, pyropheophorbide, texaphyrin, lutetium (III) texaphyrin, or gadolinium(III) texaphyrin.

other aspects, the photosensitizer can be a photoactive dye, including a merocyanine, phthalocyanine, chloroaluminum phthalocyanine, sulfonated aluminum PC, ring-substituted cationic PC, sulfonated AlPc, disulfonated or tetrasulfonated derivative, sulfonated aluminum naphthalocyanine, naphthalocyanine, tetracyanoethylene adduct, crystal violet, azure β chloride, benzophenothiazinium, benzophenothiazinium chloride (EtNBS), phenothiazine derivative, rose Bengal, toluidine blue derivatives, toluidine blue O (TBO), methylene blue (MB), new methylene blue N (NMMB), new methylene blue BB, new methylene blue FR, 1,9-dimethyl-methylene blue chloride (DMMB), methylene blue derivatives, methylene green, methylene violet Bemthsen, methylene violet 3RAX, Nile blue, Nile blue derivatives, malachite green, Azure blue A, Azure blue B, Azure blue C, safranine O, neutral red, 5-ethylamino-9-diethylaminobenzo [a]phenothiazinium chloride, 5-ethylamino-9-diethylaminobenzo[a]phenoselenazinium chloride, thiopyronine, or thionine.

In one particular aspect, the photosensitizer composition includes two benzophenothiazinium chloride (EtNBS) photosensitizers conjugated to a cephalosporin linker or fragment thereof.

In certain other aspects, the methods of the invention include the step of quantitating the signal produced by the unquenched photosensitizer. The step of quantitating the signal can include measuring the amount of the signal with a detector.

In yet another aspect, the invention provides a kit for detecting a beta-lactamase activity in a sample comprising a photosensitizer composition of the invention and instructions for using the photosensitizer composition to detect a beta-lactamase activity in a sample.

The invention also provides, in another aspect, a kit for determining the substrate specificity of a beta-lactamase activity in a sample comprising the photosensitizer composition of the invention and instructions for using the photosensitizer composition to type a beta-lactamase activity in a sample.

In still another aspect, the invention provides a method of treating a bacterial infection in a subject in need, comprising administering a therapeutically effective amount of an antibiotic, wherein the antibiotic does not have the same structure as a cleavable linker detected by any of the methods of the invention.

The present invention provides, in one aspect, a photosensitizer composition comprising a plurality of photosensitizers that are conjugated to a linker, wherein the linker includes a cleavage site for a beta-lactamase and wherein the photosensitizers are in a quenched state. In one aspect, the linker includes a cephalosporin, a penicillin, a penem, a carbapenem, a monocyclic mobactem, a polypeptide cleavable by an enzyme of *Leishmania*, or a fragment thereof. In another aspect the linker comprises a beta-lactam ring or functional derivative thereof. In yet another aspect, the linker is conjugated to two photosensitizers.

According to several aspects of the invention, the cleavage site of the linker is a substrate of a beta-lactamase of a pathogen. The pathogen can be a Gram (−) bacterium or Gram (+) bacterium. In certain aspects, the pathogen can be *Staphylococcus, Enterococcus, Enterobacter, Escherichia, Haemophilus, Neisseria, Klebsiella, Pasteurella, Proteus, Pseudomonas, Streptophomonas, Burkholderia, Acinetobacter, Serratia,* or *Salmonella* spp. The pathogen can particularly be *Staphylococcus aureus, Staphylococcus epidermis, Enterococcus faecalis, Enterococcus faecium, Escherichia coli, Haemophilus influenzae, Neisseria gonorrhea, Klebsiella pneumoniae, Pasteurella multocida, Proteus mirabilis, Pseudomonas aeruginosa, Stenotrophomonas maltophilia, Burkholderia cepacia, Acinetobacter baumannii, Enterobacter aerogines, Enterobacter cloacae, Serratia marcescens, Salmonella enterica,* and *Salmonella typhimurium*.

The photosensitizers of the photosensitizer compositions of the invention, in certain aspects, can be a porphyrin, which can include porfimer sodium, hematoporphyrin IX, hematoporphyrin ester, dihematoporphyrin ester, synthetic diporphyrin, O-substituted tetraphenyl porphyrin, 3,1-meso tetrakis porphyrin, hydroporphyrin, benzoporphyrin derivative, benzoporphyrin monoacid derivative, monoacid ring derivative, tetracyanoethylene adduct of benzoporphyrin, dimethyl acetylenedicarboxylate adduct of benzoporphyrin, δ-aminolevulinic acid, benzonaphthoporphyrazine, naturally occurring porphyrin, ALA-induced protoporphyrin IX, synthetic dichlorin, bacteriochlorin tetra(hydroxyphenyl) porphyrin, purpurin, octaethylpurpurin derivative, etiopurpurin, tin-etio-purpurin, porphycene, chlorin, chlorin $e_6$, mono-1-aspartyl derivative of chlorin $e_6$, di-1-aspartyl derivative of chlorin $e_6$, tin(IV) chlorin $e_6$, meta-tetrahydroxyphenylchlorin, chlorin $e_6$ monoethylendiamine monamide, verdin, zinc methylpyroverdin, copro II verdin trimethyl ester, deuteroverdin methyl ester, pheophorbide derivative, pyropheophorbide, texaphyrin, lutetium (III) texaphyrin, or gadolinium(III) texaphyrin.

In other aspects, the photosensitizer can be a photoactive dye, such as, a merocyanine, phthalocyanine, chloroaluminum phthalocyanine, sulfonated aluminum PC, ring-substituted cationic PC, sulfonated AlPc, disulfonated or tetrasulfonated derivative, sulfonated aluminum naphthalocyanine, naphthalocyanine, tetracyanoethylene adduct, crystal violet, azure β chloride, benzophenothiazinium, benzophenothiazinium chloride (EtNBS), phenothiazine derivative, rose Bengal, toluidine blue derivatives, toluidine blue O (TBO), methylene blue (MB), new methylene blue N (NMMB), new methylene blue BB, new methylene blue FR, 1,9-dimethylmethylene blue chloride (DMMB), methylene blue derivatives, methylene green, methylene violet Bernthsen, methylene violet 3RAX, Nile blue, Nile blue derivatives, malachite green, Azure blue A, Azure blue B, Azure blue C, safranine O, neutral red, 5-ethylamino-9-diethylaminobenzo[a]phenothiazinium chloride, 5-ethylamino-9-diethylaminobenzo[a]phenoselenazinium chloride, thiopyronine, or thionine.

In still further aspects, the photosensitizer can be a Diels-Alder adduct, dimethyl acetylene dicarboxylate adduct, anthracenedione, anthrapyrazole, aminoanthraquinone, phenoxazine dye, chalcogenapyrylium dye, cationic selena, tellurapyrylium derivative, cationic imminium salt or tetracycline.

In a particular aspect, the photosensitizer compositions of the invention can include two benzophenothiazinium chloride (EtNBS) photosensitizers conjugated to a cephalosporin linker or fragment thereof.

In certain other aspects, the photosensitizer compositions herein described can include a targeting moiety, which can target a composition to a pathogen or a host cell infected with a pathogen, or to a liposome or to a protein (e.g., cell surface protein).

In additional aspects, the photosensitizer compositions herein described can include one or more binders, which are effective to quench photoactivation of the one or more photosensitizers of the invention. A binder, which can also be called a quencher, can be a fluorophore, another photosensitizer or like compound.

In certain other aspects, the photosensitizer compositions of the invention can include a backbone which is coupled to the one or more photosensitizers, one or more binders (if present), or one or more targeting moieties (if present). The backbone can be, for example, a polyamino acid or polylysine.

In another aspect, the present invention provides a photosensitizer composition according to formula I:

X-L-X', wherein L is a linker comprising a beta-lactamase cleavage site, X is a first photosensitizer and X' is a second photosensitizer, wherein the photosensitizers are in a quenched state.

In one aspect, the linker can be a cephalosporin, a penicillin, a penem, a carbapenem, a monocyclic mobactem, a polypeptide cleavable by an enzyme of *Leishmania*, or a fragment thereof, or a compound containing a beta-lactam ring.

The cleavage site of the linker can be a substrate of a beta-lactamase of a pathogen. The pathogen can be a Gram (−) bacterium or Gram (+) bacterium. The pathogen can also be *Staphylococcus, Enterococcus, Enterobacter, Escherichia, Haemophilus, Neisseria, Klebsiella, Pasteurella, Proteus, Pseudomonas, Streptophomonas, Burkholderia, Acinetobacter, Serratia,* or *Salmonella* spp, or more particularly, can be *Staphylococcus aureus, Staphylococcus epidermis, Enterococcus faecalis, Enterococcus faecium, Escherichia coli, Haemophilus influenzae, Neisseria gonorrhea, Klebsiella pneumoniae, Pasteurella multocida, Proteus mirabilis, Pseudomonas aeruginosa, Stenotrophomonas maltophilia, Burkholderia cepacia, Acinetobacter baumannii, Enterobacter aerogines, Enterobacter cloacae, Serratia marcescens, Salmonella enterica,* or *Salmonella typhimurium*.

In another aspect, one or both of the photosensitizers, X and X', can be a porphyrin. A porphyrin can be a porfimer sodium, hematoporphyrin IX, hematoporphyrin ester, dihematoporphyrin ester, synthetic diporphyrin, O-substituted tetraphenyl porphyrin, 3,1-meso tetrakis porphyrin, hydroporphyrin, benzoporphyrin derivative, benzoporphyrin monoacid derivative, monoacid ring derivative, tetracyanoethylene adduct of benzoporphyrin, dimethyl acetylenedicarboxylate adduct of benzoporphyrin, δ-aminolevulinic acid, benzonaphthoporphyrazine, naturally occurring porphyrin, ALA-induced protoporphyrin IX, synthetic dichlorin, bacteriochlorin tetra(hydroxyphenyl) porphyrin, purpurin, octaethylpurpurin derivative, etiopurpurin, tin-etio-purpurin, porphycene, chlorin, chlorin $e_6$, mono-1-aspartyl derivative of chlorin $e_6$, di-1-aspartyl derivative of chlorin $e_6$, tin(IV) chlorin $e_6$, meta-tetrahydroxyphenylchlorin, chlorin $e_6$ monoethylendiamine monamide, verdin, zinc methylpyroverdin, copro II verdin trimethyl ester, deuteroverdin methyl ester, pheophorbide derivative, pyropheophorbide, texaphyrin, lutetium (III) texaphyrin, or gadolinium(III) texaphyrin.

In another aspect, on or both of the photosensitizers, X and X', can be a photoactive dye, including merocyanine, phthalocyanine, chloroaluminum phthalocyanine, sulfonated aluminum PC, ring-substituted cationic PC, sulfonated AlPc, disulfonated or tetrasulfonated derivative, sulfonated aluminum naphthalocyanine, naphthalocyanine, tetracyanoethylene adduct, crystal violet, azure β chloride, benzophenothiazinium, benzophenothiazinium chloride (EtNBS), phenothiazine derivative, rose Bengal, toluidine blue derivatives, toluidine blue O (TBO); methylene blue (MB), new methylene blue N (NMMB), new methylene blue BB, new methylene blue FR, 1,9-dimethylmethylene blue chloride (DMMB), methylene blue derivatives, methylene green, methylene violet Bernthsen, methylene violet 3RAX, Nile blue, Nile blue derivatives, malachite green, Azure blue A, Azure blue B, Azure blue C, safranine O, neutral red, 5-ethylamino-9-diethylaminobenzo[a]phenothiazinium chloride, 5-ethylamino-9-diethylaminobenzo[a]phenoselenazinium chloride, thiopyronine, or thionine.

In a particular aspect, X and X' of formula I can be benzophenothiazinium chloride (EtNBS) and the linker (L) can be a cepahlosporin or a fragment thereof.

In yet another aspect, formula I can include a targeting moiety, which targets a cell or tissue, such as a pathogen or a host cell infected with a pathogen, or a macrophage, or a cell or tissue or bodily component, such as a liposome or peptide.

Formula I may further include a binder effective to quench photoactivation, such as a fluorophore or another photosensitizer.

In addition, certain aspects provide formula I with a backbone, which can be utilized to couple one or more photosensitizers, binders effective to quench photoactivation, and targeting moieties.

In another aspect, the present invention provides a method for detecting a beta-lactamase activity in a sample, comprising the steps of: contacting the sample with a photosensitizer composition comprising a plurality of photosensitizers that are conjugated to a linker, wherein the linker comprise a cleavage site for a beta-lactamase and wherein the photosensitizers are in a quenched state; cleaving the linker to dequench the photosensitizers; light-activating the composition to produce fluorescence signal; and detecting the fluorescence signal with a detector, thereby detecting a beta-lactamase activity.

The sample can be a biological sample isolated from an infection in a subject, such as from a mammal or human. In one aspect, the infection is caused by an antibiotic-resistant pathogen, such as any of those listed above.

The method for detecting a beta-lactamase activity in a sample can also include the step of quantifying the detected fluorescence signal.

The present invention also provides a method for typing beta-lactamase activity in a sample, comprising: performing a non-competitive reaction comprising the steps of (a) contacting the sample with a photosensitizer composition comprising a plurality of photosensitizers that are conjugated to a linker, wherein the linker comprise a cleavage site for a beta-lactamase and wherein the photosensitizers are in a quenched state; (b) cleaving the linker to dequench the photosensitizers; (c) light-activating the composition to produce a fluorescence signal; and (d) quantifying the fluorescence signal with a detector.

The present invention also provides a method for determining an appropriate antibiotic regimen to be administered to a subject in need thereof, comprising the steps of: typing a beta-lactamase activity of a sample according to the invention based on one or more competing beta-lactam substrates; and administering to the subject in need thereof an antibiotic regimen that excludes any antibiotic having a structure that is the same or is similar to the competing beta-lactam substrates that are shown to be cleavable by the beta-lactamase activity of the sample.

Methods of typing beta-lactamases and for detecting and/or quantitating beta-lactamase activities can be done on any suitable sample containing a beta-lactamase enzyme. In one aspect, the sample is obtained from infected cells or tissues of a subject having a bacterial infection, such as an infection by a Gram (−) or Gram (+) bacterial pathogen. Sample cells and/or tissues can be infected with or contain *Staphylococcus, Enterococcus, Enterobacter, Escherichia, Haemophilus, Neisseria, Klebsiella, Pasteurella, Proteus, Pseudomonas, Streptophomonas, Burkholderia, Acinetobacter, Serratia,* and *Salmonella* spp., as well as more particularly *Staphylococcus aureus, Staphylococcus epidermis, Enterococcus faecalis, Enterococcus faecium, Escherichia coli, Haemophilus influenzae, Neisseria gonorrhea, Klebsiella pneumoniae, Pasteurella multocida, Proteus mirabilis, Pseudomonas aeruginosa, Stenotrophomonas maltophilia, Burkholderia cepacia, Acinetobacter baumannii, Enterobacter aerogines, Enterobacter cloacae, Serratia marcescens, Salmonella enterica,* and *Salmonella typhimurium.*

The present invention also includes a kit for detecting a beta-lactamase activity in a sample containing a photosensitizer composition described herein and instructions for using the photosensitizer composition to detect a beta-lactamase activity in a sample.

The instant invention further provides a kit for typing a beta-lactamase activity in a sample comprising a photosensitizer composition described herein and instructions for using the photosensitizer composition to type a beta-lactamase activity in a sample.

Other aspects of the invention are described in the following disclosure, and are within the ambit of the invention.

BRIEF DESCRIPTION OF THE DRAWINGS

The following Detailed Description, given by way of example, but not intended to limit the invention to specific embodiments aspects described, may be understood in conjunction with the accompanying drawings, which incorporated herein by reference. Various features and aspects of the present invention will now be described by way of non-limiting examples and with reference to the accompanying drawings, in which:

FIG. 3 shows MS spectra obtained for (a) 7-[(2-phenylacetyl)amino] 3-hydrodxymethy cephalosporanic acid; and (b) cephalosporanic acid-toluidine blue O prodrug.

Figure 1:
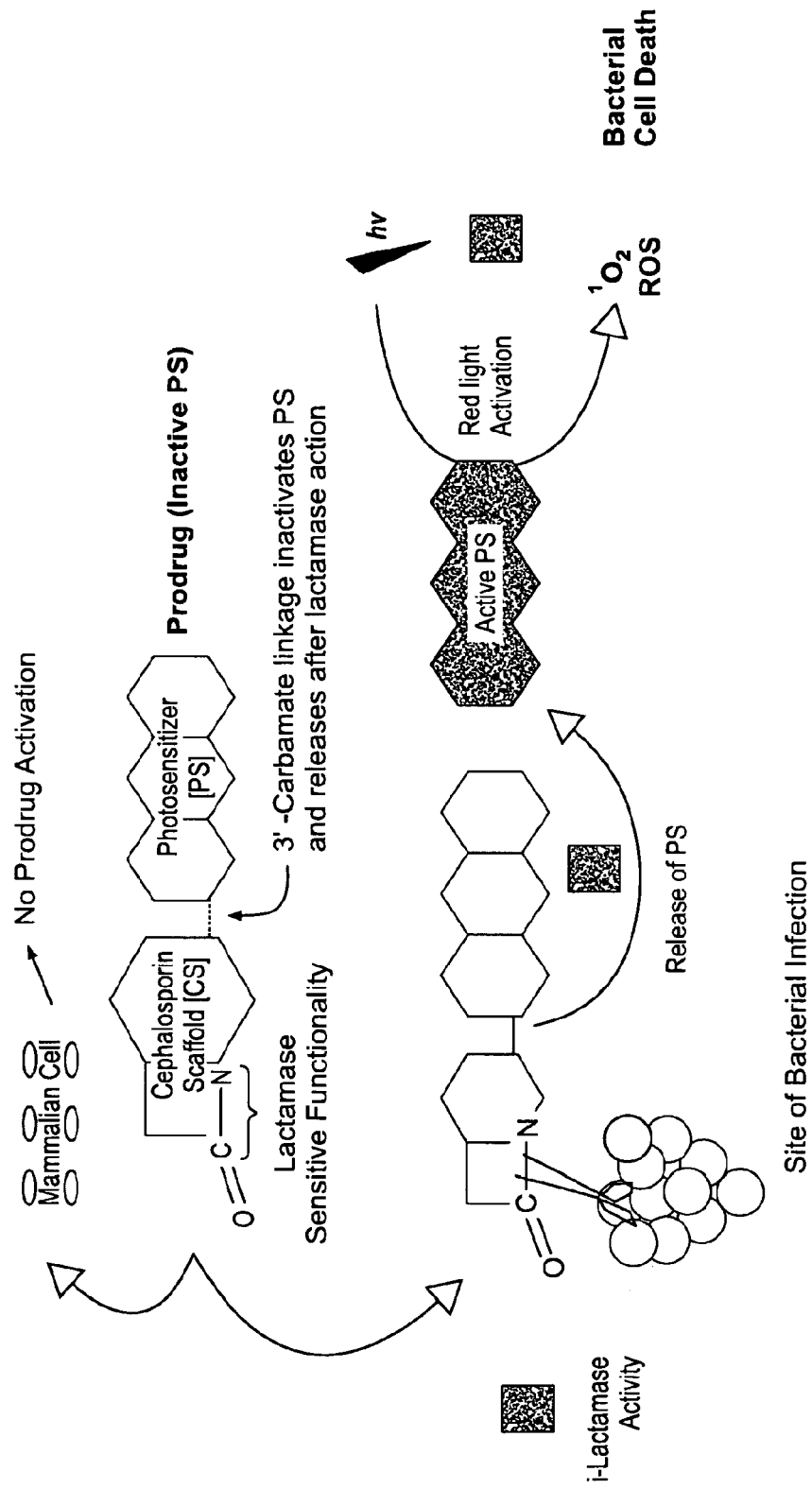
FIG. 1 schematically depicts the development of a carbamate-linked photosensitizer (PS) that is inactive (with or without light) while linked and is light-activatable only when released by the β-lactamase enzyme-mediated cleavage.

The term "photosensitizer" refers to an activatable compound that produces a signal when light activated. The photosensitizers of the invention can produce a photochemical or phototoxic effect on a cell when light activated, i.e., produce a reactive species when light activated. The photosensitizers of the invention can include photosensitizer fragments and/or derivatives of known photosensitizers, which have the same or substantially the same function as the known photosensitizers, which means that function which is at least about 50% of the function of an original photosensitizer, more preferably about 60% or 70%, or still more preferably about 80% or 90%, or even more preferably about 95% or 99% the function of the known photosensitizer compound.

The photosensitizers of the invention can include "photoactive dyes," which, as used herein, refers to those photosensitizers that produce a fluorescent signal when activated, but not necessarily a reactive species in phototoxic amounts (i.e., a phototoxic species). Signals that can be measured from a photoactive dye include: (i) phosphorescence, (ii) fluorescence, (iii) reactive molecular species. The first two are a component of light itself and the last one is a physic-chemical consequence of light absorption by the photoactive dye. The photoactive dyes of the invention may also be fragments and/or derivatives of a known photoactive dyes which have the same or substantially the same function as a known photoactive dye, which means a function that is at least about 50% of the function of a known photoactive dye, more preferably about 60% or 70%, or still more preferably about 80% or 90%, or even more preferably about 95% or 99% the function of a known photoactive dye.

Depending on the wavelength and power of light administered, a photosensitizer can be activated to fluoresce and, therefore, act as a photoactive dye, but not produce a phototoxic species. The wavelength and power of light can be adapted by methods known to those skilled in the art to bring about a phototoxic effect where desired.

The term "photosensitizer composition," as used herein, refers to chemical constructs having one or more photosensitizers (or fragments and/or derivatives thereof), as well as other materials, such as linkers, backbones, targeting moieties and binders, that may be couple thereto.

As used herein, the term "fluorescent dye" refers to dyes that are fluorescent when illuminated with light but do not produce reactive species that are phototoxic.

Any compound or moiety of the invention that is fluorescent in one or more states can contain one or more "fluorophores," which refers to a compound or portion thereof which exhibits fluorescence. The term "fluorogenic" refers to a compound or composition that becomes fluorescent or demonstrates a change in its fluorescence (such as an increase or decrease in fluorescence intensity or a change in its fluorescence spectrum) upon interacting with another substance, for example, upon binding to a biological compound or metal ion, upon reaction with another molecule or upon metabolism by an enzyme. Fluorophores may be substituted to alter their solubility, spectral properties and/or physical properties. Numerous fluorophores and fluorogenic compounds and compositions are known to those skilled in the art and include, but are not limited to, benzofurans, quinolines, quinazolines, quinazolinones, indoles, benzazoles, indodicarbocyanines, borapolyazaindacenes and xanthenes, with the latter including fluoresceins, rhodamines and rhodols as well as other fluorophores described in Haugland, Molecular Probes, Inc. Handbook of Fluorescent Probes and Research Chemicals, ($9^{th}$ ed., including the CD-ROM, September 2002), and include the photosensitizers, photoactive dyes, and fluorescent compounds and moieties of the invention.

The term "conjugated," as used herein, refers to the coupling or association of two or more molecules (e.g., a photosensitizer and a linker), usually by covalently bonding.

As used herein, the term "detectable" or "directly detectable," or the like, refers to the presence of a detectable signal generated from a compound of the invention, e.g., a photosensitizer, that is detectable by observation, instrumentation, or film without requiring chemical modifications or additional substances.

As used herein, the term "linker" refers to an agent capable of linking two or three components (e.g., compounds or moieties) of the photosensitizer composition together (e.g., a photosensitizer to another photosensitizer, a photosensitizer to a binder, a photosensitizer to a backbone, a binder to a backbone, a photosensitizer to a targeting moiety, or a binder to a targeting moiety). A linker is a relatively small moiety with only two or three conjugatable end groups to link between two or three molecules/targeting agents. The "linker" may be cleavable. Examples of linkers are described herein.

In addition to enzymatically cleavable groups, e.g., beta-lactam moieties, it is within the scope of the present invention to include one or more sites in a linker that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., Biochem. Biophys. Acta, 761: 152-162 (1983); Joshi et al., J. Biol. Chem., 265: 14518-14525 (1990); Zarling et al., J. Immunol, 124: 913-920 (1980); Bouizar et al., Eur. J. Biochem., 155: 141-147 (1986); Park et al., J. Biol. Chem., 261: 205-210 (1986); Browning et al., J. Immunol., 143: 1859-1867 (1989), each of which are incorporated by reference.

As used herein, the term "backbone" refers to an agent that functions to couple one or more components of a photosensitizer composition of the invention, such as, for example, a polyamino acid or like agent that is linked to one or more photosensitizers and/or one or more binders and/or one or more targeting moieties The backbone itself additionally can be a targeting moiety, e.g. polylysine. A "backbone" as used herein is as a moiety higher in molecular weight and capable of loading more photoactive molecules than a 'linker'. Backbone can be a polymeric structure which provides a base to add multiple units (more than three). Examples of backbones that can be used according to the invention, include, but are not limited to polyethylene glycol and polyproline.

The term "sample," as used herein, refers to any material that may contain a beta-lactamase or a nucleotide sequence coding for a beta-lactamase, or to a material to which a beta-lactamase or a nucleotide sequence coding for a beta-lactamase is added. Typically, the sample may be obtained from and/or contain a bodily tissue, cell, or fluid of a subject, and can comprise endogenous host cell proteins, nucleic acid polymers, nucleotides, oligonucleotides proteins or peptides isolated or obtained therefrom. The sample may be presented in any suitable physical form, such as, for example, a fluid dispersion, such as an aqueous solution, a cell culture (viable or otherwise) or immobilized on a solid or semi solid surface such as a polyacrylamide gel, membrane blot or microarray.

As used herein, the term "binder" refers to an agent that absorbs energy from an adjacent, activated photosensitizer or otherwise inactivates the photosensitizer, and, thus, quenches the photosensitizer. A "binder" may be used synonymously with the term "quencher," which may also refer to a compound or moiety that absorbs energy from an excited donor compound or moiety. A quencher may absorb the fluorescent photons emitted by a donor compound, thereby masking the donor compound's fluoroscence. A binder can participate in both static (ground state) and dynamic (excited state) quenching. That is, in the context of an EtNBS-linker-EtNBS configuration (an example of static quenching), either of the EtNBS moieties can be considered to be the binder, while the other EtNBS can be considered as the fluorophore. Alternatively, the invention contemplates an embodiment of a photoactivatable prodrug as disclosed herein where the prodrug has the configuration EtNBS-linker-binder. This configuration would represent an example of dynamic-type quenching in which the binder (e.g., fluoroscein) functions to quench the signal generated by EtNBS until the two moieties are separated by cleavage of the linker.

As used herein, the terms "peptide," "polypeptide," and "protein" are, unless specified otherwise, used interchangeably. Peptides, polypeptides, and proteins used in methods and compositions described herein can be recombinant, purified from natural sources, or chemically synthesized. For example, reference to the use of a bacterial protein or a protein from bacteria, includes the use of recombinantly produced molecules, molecules purified from natural sources, or chemically synthesized molecules.

The term "subject" is used herein to refer to a living animal, including a human. The subject can be infected with or carrying an unwanted organism, e.g., a bacterial infection.

As used herein, "pathogen" or "target organism" means an organism which causes or aggravates a disorder, such as an infection, granuloma, or other adverse immune response.

The term "obtaining," as in "obtaining" the "photosensitizer composition," "linker" or "binder," is intended to include purchasing, synthesizing or otherwise acquiring the elements of the invention.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Antibiotics, Resistance and Beta-Lactamase

While not intending to limit the present invention, the following general description of antibiotics, resistance and beta-lactamase is provided.

In general, antimicrobial chemotherapeutics are classified based on chemical structure and mode of action. In particular, antibiotics can be classified as (a) agents that inhibit the synthesis of bacterial cell walls, including the β-lactam class of antibiotics (e.g., penicillins, cephalosporins, or carbapenems) or other dissimilar agents such as vancomycin and bacitracin, (b) agents that act to permeabilize the cellular membrane causing a toxic release of intracellular material (e.g., detergents such as polymyxin), (c) agents that disrupt the function of 30S or 50S ribosomal subunits to interupt protein synthesis (e.g., chloramphenicol, tetracyclines, or erythromycine), (d) agents that inhibit or block bacterial nucleic acid synthesis or metabolism (e.g., rifampin, rifabutin, or quinolones), and (e) agents that block or inhibit bacterial metabolism (e.g., trimethoprim or sulfonamides). Regarding beta-lactam antibiotics, in particular, resistance to such compounds is due mainly to the ability of resistant bacteria to express beta-lactamase enzymes, which are released from the cell and which hydrolyze the beta-lactam rings of the antibiotics, thereby inactivating them.

The β-lactam class of antibiotics represent a large and important class of antibiotics whose overall effectiveness is threatened by the emergence of resistance, which is in particular, caused by the continued appearance of beta-lactamase enzymes in various bacteria. Beta-lactamases represent an efficient mechanism devised by bacteria to escape the lethal action of beta-lactam antibiotics. They can be chromosomal or plasmid encoded, produced in a constitutive or inducible manner, and can be secreted into the periplasmic space of Gram negative strains or into the outer medium by their Gram positive counterparts. The ubiquitous occurrence of beta-lactamases in bacteria and their association with clinical resistance has sustained a strong interest in these enzymes. Just a few years after the clinical debut of penicillin in 1944, the first reports of resistance to the beta-lactam antibiotisc had emerged. Currently, there are over 500 known different beta-lactamases, of which 200 of them are extended-spectrum-beta-lactamases (ESBLs) (Paterson et al., Clin. Microbio. Rev. 2005, 18:657-686).

As briefly mentioned above, β-lactamases are organized under one classification scheme into four molecular classes (A, B, C and D) based on their amino acid sequences. Class A enzymes have a molecular weight of about 29 kDa and preferentially hydrolyze penicillins. Examples of class A enzymes include the β-lactamase of *Staphylococcus aureus*. Class B enzymes include metalloenzymes that have a broader substrate profile than the other classes of β-lactamases. Class C enzymes have molecular weights of approximately 39 kDa and include the chromosomal cephalosporinases of gram-negative bacteria, which are responsible for the resistance of gram-negative bacteria to a variety of both traditional and newly designed antibiotics. In addition, class C enzymes also include the lactamase of P99 *Enterobacter cloacae*, which is responsible for making this *Enterobacter* species one of the most widely spread bacterial agents in United States hospitals. The recently recognized class D enzymes are serine hydrolases, which exhibit a unique substrate profile.

The four classes of A, B, C and D beta-lactamases can be further categorized into functional clusters through the Bush-Jacoby-Medeiros classification system (Philippon et al., 1998). In considering two of the four classes, A and C, one can demonstrate that there is a high level of ambiguity in the relationship between the primary amino acid sequence of the enzymes and the functional phenotypes that their expression confers. The class C beta-lactamases include both chromosomal and plasmid borne members whose activity is highly similar, with conserved motifs, but whose total sequence identity can vary as much as 40% (Philippon et al., 1998). The functional phenotype associated with their expression is characterized by resistance to amino penicillins, first-generation cephalosporins, cefoxitin, and to amoxicillin/clavulanate combinatorial therapy (Philippon et al., 1998). Conversely, the class A beta-lactamases, encompassing the ESBLs, can share a high degree of sequence identity, but are the most functionally diverse of the four Amber classes. The range of phenotypes within class A includes resistance to penicillins only, to penicillins and some cephalosporins, to cephalosporins and cefuroxime, to third generation cephalosporins, to beta-lactamase inactivators, or to imipenem (Philippon et al., 1998). Some class A enzymes, although 97% similar in primary structure, exhibit great differences in kinetics for various substrates. This relationship is exemplified by the enzymes TEM1 and TEM12 (ESBL) where a single amino acid difference in a primary sequence of 286 amino acids changes the resistance phenotype from that of resistance to broad-spectrum cephalosporins to that of resistance to third-generation extended spectrum cephalosporins (Philippon et al., 1998).

Other details regarding the nature of antibiotics, resistance mechanisms and beta-lactamase enzymes will be well appreciated by those having ordinary skill in the art.

Compositions of the Invention
Photosensitizer Compositions of the Invention

The present invention provides, in one aspect, a photosensitizer composition comprising one or more photosensitizers that are conjugated to a linker, wherein the linker comprises a cleavage site (e.g., a beta-lactamase enzyme cleavage site) and wherein the one or more photosensitizers, when coupled together by a linker, are in a quenched state. Upon cleavage of the linker (e.g., by an enzyme capable of cleaving the cleavage site), the one or more photosensitizers become unquenched and photoactivatable. The unquenched photosensitizers can then be activated to produce a signal (e.g., light emission), which can then be detected by a detection means (e.g., a fluorimeter). The linker of the invention can comprise one or more beta-lactamase cleavage sites, each site comprising at least one beta-lactam moiety or functional derivative thereof.

Any suitable physical arrangement of the one or more photosensitizers and the linker is contemplated by the present invention, so long as the cleavage of the linker results in, either directly or indirectly, the unquenching of the one or more photosensitizers. It will be appreciated by those having ordinary skill in the art that quenching is a reduction in intensity of the excited state of a photosensitizer. Quenching can be attained in many different ways. For example, two mechanisms include: (i) static quenching caused by dimerization in ground state and (ii) dynamic quenching caused by FRET (fluorescence resonance energy transfer), that represents energy transfer between an excited donor and a ground-state acceptor molecule. Quenching may also be attained by other methods, including, for example, photoinduced electron transfer, paramagnetic enhancement of intersystem crossing, Dexter exchange coupling, and exciton coupling such as the formation of dark complexes. Quenched state depends on the distance between two photoactive molecules. This distance can be defined by the choice of linker molecule. For example, a flexible linker can be used to alter the distance between two molecules with respect to temperature and solvent conditions and analyze the best distance for quenching. Otherwise, a rigid linker can be employed to observe quenching efficiency at a fixed distance. Quenching refers to any process that decreases the fluorescence intensity of a sample and includes excited-state reactions, molecular rearrangements, energy transfer, ground-state complex formation, and collisional quenching.

In a particular aspect, the photosensitizer composition of the present invention is represented by the general formula I:

X-L-X', wherein at least one of X or X' is a photosensitizer in accordance with the invention and wherein L represents an uncleaved linker. In another aspect, X and X' can be the same or different photosensitizers. In yet another aspect, X can be a photosensitizer and X' can be a binder or quencher which quenches the photosensitizer. In certain other aspects, X and/or X' can be a photoactive dye, such as, for example, a phenothiazine (e.g., benzophenothiazinium chloride (EtNBS)) or functional derivative or fragment thereof. The linker (L) can be any suitable linker disclosed herein, which at a minimum contains at least one enzyme-cleavable site (e.g., a beta-lactam moiety).

In a particular aspect, X and X' are each benzophenothiazinium chloride (EtNBS) and L comprises a beta-lactam moiety or derivative thereof, such as, for example a penicillin or a cephalosporin, or derivative thereof. X and X' can be benzophenothiazinium chloride (EtNBS) and L can comprise a cephalosporin.

In other aspects, the photosensitizer compositions of the invention can include one or more targeting moieties, which can be coupled to the linker (L) or to one or more of the photosensitizers X or X'. The photosensitizer compositions in other embodiments can also be coupled to a backbone. Targeting moieties useful in the present invention include antibodies, aptamers, proteins, and peptides. Targeting moieties include biological macromolecules; proteins, nucleic acids, lipids, and carbohydrates, as well as small molecules and chemical functional groups.

The following description provides further guidance regarding the nature of the components of the photosensitizer compositions of the invention.

Photosensitizers

Any suitable photosensitizer or combination of photosensitizers can be joined to any suitable linker to form the photosensitizer compositions of the invention, provided that the photosensitizers are quenched when the linker is uncleaved, but become unquenched when the linker is cleaved. Photosensitizers of the invention can have the following general characterisitics: Reasonable fluorescence quantum yield for diagnostics, significant phototoxicity for therapy, minimum dark toxicity, absorption in light region of spectrum (400-800 nm), and a Fortser radius between FRET pairs of 2-8 nm.

The photosensitizers of the invention can be amphiphilic, meaning that they share the opposing properties of being water-soluble, yet hydrophobic. The photosensitizer should be water-soluble in order to pass through the bloodstream systemically, however, it should also be hydrophobic enough to pass across cell membranes. Modifications, such as attaching polar residues (amino acids, sugars, and nucleosides) to the hydrophobic porphyrin ring, can alter polarity and partition coefficients to desired levels. Such methods of modification are well known in the art.

In specific embodiments, photosensitizers of the present invention absorb light at a relatively long wavelength, thereby absorbing at low energy. Low-energy light can travel further through tissue than high-energy light, which becomes scattered. Optimal tissue penetration by light occurs between about 650 and about 800 nm. Porphyrins found in red blood cells typically absorb at about 630 nm, and new, modified porphyrins have optical spectra that have been "red-shifted", in other words, absorbs lower energy light. Other naturally occurring compounds have optical spectra that is red-shifted with respect to porphyrin, such as chlorins found in chlorophyll (about 640 to about 670 nm) or bacteriochlorins found in photosynthetic bacteria (about 750 to about 820 nm).

In certain embodiments, the photosensitizers of the invention can include porphyrins and/or hydroporphyrins. Porphyrins and hydroporphyrins can include, but are not limited to, Photoformn® (porfimer sodium), hematoporphyrin IX, hematoporphyrin esters, dihematoporphyrin ester, synthetic diporphyrins, O-substituted tetraphenyl porphyrins (picket fence porphyrins), 3,1-meso tetrakis (o-propionamido phenyl) porphyrin, hydroporphyrins, benzoporphyrin derivatives, benzoporphyrin monoacid derivatives (BPD-MA), monoacid ring "a" derivatives, tetracyanoethylene adducts of benzoporphyrin, dimethyl acetylenedicarboxylate adducts of benzoporphyrin, endogenous metabolic precursors, δ-aminolevulinic acid, benzonaphthoporphyrazines, naturally occurring porphyrins, ALA-induced protoporphyrin IX, synthetic dichlorins, bacteriochlorins of the tetra (hydroxyphenyl) porphyrin series, purpurins, tin and zinc derivatives of octaethylpurpurin, etiopurpurin, tin-etio-purpurin, porphycenes, chlorins, chlorin $e_6$, mono-1-aspartyl derivative of chlorin $e_6$, di-1-aspartyl derivative of chlorin $e_6$, tin(IV) chlorin $e_6$, meta-tetrahydroxyphenylchlorin, chlorin $e_6$ monoethylendiamine monamide, verdins such as, but not limited to zinc methylpyroverdin (ZNMPV), copro II verdin trimethyl ester (CVTME) and deuteroverdin methyl ester (DVME), pheophorbide derivatives, and pyropheophorbide compounds, texaphyrins with or without substituted lanthanides or metals, lutetium (III) texaphyrin, and gadolinium(III) texaphyrin, or a functional derivative or fragment thereof, i.e., compounds that are chemically similar and/or are small portions of the original compound which perform the same or substantially the same function. Where any moiety, fragment or derivative of a compound of the invention performs "substantially the same function" as the original compound, that moiety, fragment or derivative performs at least about 50% of the activity of the original compound, more preferably about 60% or 70%, or still more preferably about 80% or 90%, or even more preferably about 95% or 99% the activity of the original compound.

Porphyrins, hydroporphyrins, benzoporphyrins, and derivatives are all related in structure to hematoporphyrin, a molecule that is a biosynthetic precursor of heme, which is the primary constituent of hemoglobin, found in erythrocytes. First-generation and naturally occurring porphyrins are excited at about 630 nm and have an overall low fluorescent quantum yield and low efficiency in generating reactive oxygen species. Light at about 630 nm can only penetrate tissues to a depth of about 3 mm, however there are derivatives that have been 'red-shifted' to absorb at longer wavelengths, such as the benzoporphyrins BPD-MA (Verteporfin). Thus, these 'red-shifted' derivatives show less collateral toxicity compared to first-generation porphyrins.

Porphyrin derivatives also include chlorins and bacteriochlorins, however these have the unique property of hydrogenated exo-pyrrole double bonds on the porphyrin ring backbone, which allows for absorption at wavelengths greater than about 650 nm. Chlorins are derived from chlorophyll, and modified chlorins such as meta-tetra hydroxyphenylchlorin (mTHPC) have functional groups to increase solubility. Bacteriochlorins are derived from photosynthetic bacteria and are further red-shifted to about 740 nm. A specific embodiment of the invention uses chlorin$_{e6}$.

Porphryin derivatives also include purpurins, porphycenes, and verdins, which have efficacies similar to or exceeding hematoporphyrin. Purpurins contain the basic porphyrin macrocycle, but are red-shifted to about 715 nm. Porphycenes have similar activation wavelengths to hematoporphyrin (about 635 nm), but have higher fluorescence quantum yields. Verdins contain a cyclohexanone ring fused to one of the pyrroles of the porphyrin ring. Phorbides and pheophorbides are derived from chlorophylls and have 20 times the effectiveness of hematoporphyrin. Texaphyrins are new metal-coordinating expanded porphyrins. The unique feature of texaphyrins is the presence of five, instead of four, coordinating nitrogens within the pyrrole rings. This allows for coordination of larger metal cations, such as trivalent lanthanides. Gadolinium and lutetium are used as the coordinating metals. In a specific embodiment, the photosensitizer can be Antrin®, otherwise known as motexafin lutetium.

5-aminolevulinic acid (ALA) is a precursor in the heme biosynthetic pathway, and exogenous administration of this compound causes a shift in equilibrium of downstream reactions in the pathway. In other words, the formation of the immediate precursor to heme, protoporphyrin IX, is dependent on the rate of 5-aminolevulinic acid synthesis, governed in a negative-feedback manner by concentration of free heme. Conversion of protoporphyrin IX is slow, and where desired, administration of exogenous ALA can bypass the negative-feedback mechanism and result in accumulation of phototoxic levels of ALA-induced protoporphyrin IX. ALA is rapidly cleared from the body, but like hematoporphyrin, has an absorption wavelength of about 630 nm.

First-generation photosensitizers are exemplified by the porphyrin derivative Photofrin®, also known as porfimer sodium. Photofrin® is derived from hematoporphyrin-IX by acid treatment and has been approved by the Food and Drug Administration for use in PDT. Photofrin® is characterized as a complex and inseparable mixture of monomers, dimers, and higher oligomers. There has been substantial effort in the field to develop pure substances that can be used as successful photosensitizers. Thus, in a specific embodiment, the photosensitizer is a benzoporphyrin derivative ("BPD"), such as BPD-MA, also commercially known as Verteporfin. U.S. Pat. No. 4,883,790 describes BPDs. Verteporfin has been thoroughly characterized (Richter et al., 1987; Aveline et al., 1994; Levy, 1994) and it has been found to be a highly potent photosensitizer for PDT. Verteporfin has been used in PDT treatment of certain types of macular degeneration, and is thought to specifically target sites of new blood vessel growth, or angiogenesis, such as those observed in "wet" macular degeneration. Verteporfin is typically administered intravenously, with an optimal incubation time range from 1.5 to 6 hours. Verteporfin absorbs at 690 nm, and is activated with commonly available light sources. One tetrapyrrole-based photosensitizer having recent success in the clinic is MV0633 (Miravant).

The photosensitizers can have a chemical structure that includes multiple conjugated rings that allow for light absorption and photoactivation. Such specific compounds include motexafin lutetium (Antrin®) and chlorin$_{e6}$.

The photosensitizers of the present invention also include cyanines and other photoactive dyes. Cyanine and other dyes include but are not limited to a merocyanine, phthalocyanine, chloroaluminum phthalocyanine, sulfonated aluminum PC, ring-substituted cationic PC, sulfonated AlPc, disulfonated or tetrasulfonated derivative, sulfonated aluminum naphthalocyanine, naphthalocyanine, tetracyanoethylene adduct, crystal violet, azure β chloride, benzophenothiazinium, benzophenothiazinium chloride (EtNBS), phenothiazine derivative, phenothiaziniums such as rose Bengal, toluidine blue derviatives, toluidine blue 0 (TBO), methylene blue (MB), new methylene blue N (NMMB), new methylene blue BB, new methylene blue FR, 1,9-dimethyl-methylene blue chloride (DMMB), methylene blue derivatives, methylene green, methylene violet Bernthsen, methylene violet 3RAX, Nile blue, Nile blue derivatives, malachite green, Azure blue A, Azure blue B, Azure blue C, safranine O, neutral red, 5-ethylamino-9-diethylaminobenzo[a]phenothiazinium chloride, 5-ethylamino-9-diethylaminobenzo[a]phenoselenazinium chloride, thiopyronine, or thionine.

Cyanines are deep blue or purple compounds that are similar in structure to porphyrins. However, these dyes are much more stable to heat, light, and strong acids and bases than porphyrin molecules. Cyanines, phthalocyanines, and naphthalocyanines are chemically pure compounds that absorb light of longer wavelengths than hematoporphyrin derivatives with absorption maxima at about 680 nm. Phthalocyanines, belonging to a new generation of substances for PDT are chelated with a variety of diamagnetic metals, chiefly aluminum and zinc, which enhance their phototoxicity. A ring substitution of the phthalocyanines with sulfonated groups will increase solubility and affect the cellular uptake. Less sulfonated compounds, which are more lipophilic, show the best membrane-penetrating properties and highest biological activity. The kinetics are much more rapid than those of HPD, where, for example, high tumor to tissue ratios (8:1) were observed after 1-3 hours. The cyanines are eliminated rapidly and almost no fluorescence can be seen in the tissue of interest after 24 hours.

Other photoactive dyes such as methylene blue and rose bengal, are also used for photodynamic therapy. Methylene blue is a phenothiazine cationic dye that is exemplified by its ability to specifically target mitochondrial membrane potential. Rose-bengal and fluorescein are xanthene dyes that are well documented in the art for use in photodynamic therapy. Rose bengal diacetate is an efficient, cell-permeant generator of singlet oxygen. It is an iodinated xanthene derivative that has been chemically modified by the introduction of acetate groups. These modifications inactivate both its fluorescence and photosensitization properties, while increasing its ability to cross cell membranes. Once inside the cell, esterases remove the acetate groups and restore rose bengal to its native structure. This intracellular localization allows rose bengal diacetate to be a very effective photosensitizer.

In other aspects, the photosensitizers can be Diels-Alder adducts, dimethyl acetylene dicarboxylate adducts, anthracenediones, anthrapyrazoles, aminoanthraquinone, phenoxazine dyes, chalcogenapyrylium dyes such as cationic selena and tellurapyrylium derivatives, cationic imminium salts, and tetracyclines are other compounds that also exhibit photoactive properties and can be used advantageously in photodynamic therapy. Other photosensitizers that do not fall in either of the aforementioned categories have other uses besides photodynamic therapy, but are also photoactive. For example, anthracenediones, anthrapyrazoles, aminoanthraquinone compounds are often used as anticancer therapies (i.e. mitoxantrone, doxorubicin). Chalcogenapyrylium dyes such as cationic selena- and tellurapyrylium derivatives have also been found to exhibit photoactive properties in the range of about 600 to about 900 nm range, more preferably from about 775 to about 850 nm. In addition, antibiotics such as tetracyclines and fluoroquinolone compounds have demonstrated photoactive properties.

Linkers/Enzyme Cleavage Site

Linkers of the invention are capable of linking two or more components of the photosensitizer composition together (e.g., a photosensitizer to another photosensitizer, a photosensitizer to a binder, a photosensitizer to a backbone, a binder to a backbone, a photosensitizer to a targeting moiety, or a binder to a targeting moiety). Any bond which is capable of linking the components such that they are stable under physiological conditions for the time needed for administration and treatment is suitable, but covalent linkages are advantageous. The link between two components may be direct, e.g., where a photosensitizer is linked directly to another photosensitizer, or indirect, e.g., where a photosensitizer is linked to an intermediate, e.g., linked to a backbone, and that intermediate is linked to another photosensitizer. A linker should function under conditions of temperature, pH, salt, solvent system, and other reactants that substantially retain the chemical stability of the photosensitizer, the backbone (if present), and the targeting moiety.

Linkers can comprise an enzyme cleavage site for a bacterial enzyme. In one aspect of the invention, linker cleavage by a pathogen enzyme causes reduction of the quenching that results from the conformation adopted by the multiple photosensitizers linked to one another. In another aspect, linker cleavage by a pathogen enzyme causes reduction of the quenching that results from inclusion of a binder (e.g., a quencher, see above). Without being bound by theory, target cells cause reduction of quenching by the endogenous production of an enzyme which cleaves the linker. The linker enzyme cleavage site can be a beta-lactamase cleavage site comprising one or more beta lactam ring moieties. In a further embodiment, the linker comprises a penicillin or cephalosporin or functional derivative or fragment thereof.

One of the mechanisms utilized by bacteria to become resistant to an antibiotic involves the production of an enzyme that inactivates the antibiotic. An example of this type of resistance constitutes the beta-lactamase enzymes, as described above. The beta-lactamase enzymes cleave the four-membered (three carbon, one nitrogen) β-lactam (2-azetidinone) ring that constitutes the unique structural feature shared by the β-lactam antibiotics. This family of antibiotics includes the penicillins, cephalosporins, penems, carbapenems, and monocyclic monobactams, among others. Accordingly, in specific embodiments, the linker comprises a penicillin, a cephalosporin, a carbapenem, or a monocyclic monobactam or a fragment thereof (e.g., comprising a beta-lactam ring). Such linkers can include derivatives of cephalosporin or other antibiotics, wherein such a derivative is cleaved by beta-lactamase to the same or similar extent as the parent linker. Examples of derivatives of linkers include a linker as described herein, such as cephalosporin, which is conjugated to an additional moiety, such as, for example, cephalosporin conjugated to aminothiophenol.

Another example of this type of resistance constitutes VanX, a dipeptidase that cleaves D-Ala-D-Ala and catalyzes hydrolysis of the D-alanyl-D-alanine dipeptide normally used in wild-type peptidoglycan biosynthesis. VanX-related proteins are involved in the production of a variant peptidoglycan (D-alanine-D-lactate) that results in resistance of pathogenic bacteria to the antibiotic vancomycin. D-ala-D-ala peptidase has been found to be contained in the operon that encodes vancomycin resistance in *Enterococcus faecalis* and *Enterococcus faecium*.

Linkers can also be cross-linking agents that are homo- or hetero-bifunctional.

Many linkers react with an amine and a carboxylate, to form an amide, or an alcohol and a carboxylate to form an ester. Linkers are known in the art, see, e.g., M. Bodansky, "Principles of Peptide Synthesis", 2nd ed., referenced herein, and T. Greene and P. Wuts, "Protective Groups in Organic Synthesis," 2nd Ed, 1991, John Wiley, NY. Linkers should link component moieties stably, but such that there is only minimal or no denaturation or deactivation of the photosensitizer or other linked component.

The photosensitizer compositions of the invention can be prepared by linking the photosensitizers to one another or to other components using methods known in the art. A variety of linkers, including cross-linking agents, can be used for covalent conjugation. Examples of cross-linking agents include N,N'-dicyclohexylcarbodiimide (DCC), N-succinimidyl-5-acetyl-thioacetate (SATA), N-succinimidyl-3-(2-pyridyldithio)propionate (SPDP), ortho-phenylenedimaleimide (o-PDM), and sulfosuccinimidyl 4-(N-maleimidomethyl)cyclohexane-1-carboxylate (sulfo-SMCC) (Karpovsky et al. (1984) J. Exp. Med. 160:1686; Liu, M A et al. (1985) Proc. Natl. Acad. Sci. USA 82:8648): Other methods include those described by Paulus and Behring (1985) Ins. Mitt., 78:118-132; Brennan et al. (1985) Science 229:81-83 and Glennie et al., (1987) J. Immunol, 139:2367-2375. A large number of linkers for peptides and proteins, along with buffers, solvents, and methods of use, are described in the Pierce Chemical Co. catalog, pages T-155 to T-200, 1994 (3747 N. Meridian Rd., Rockford Ill., 61105, U.S.A.; Pierce Europe B.V., P.O. Box 1512, 3260 BA Oud Beijerland, The Netherlands), the contents of which are hereby incorporated by reference.

DCC is a useful linker (Pierce #20320; Rockland, Ill.). DCC(N,N'-dicyclohexylcarbodiimide) is a carboxy-reactive cross-linker commonly used as a linker in peptide synthesis. Another useful cross-linking agent is SPDP (Pierce #21557), a heterobifunctional cross-linker for use with primary amines and sulfhydryl groups. SPDP produces cleavable cross-linking such that, upon further reaction, the agent is eliminated, so the photosensitizer can be linked directly to a backbone or molecular carrier. Other useful linking agents are SATA (Pierce #26102), for introduction of blocked SH groups for two-step cross-linking (Pierce #26103), and sulfo-SMCC (Pierce #22322), reactive towards amines and sulfhydryls. Other cross-linking and coupling agents are also available from Pierce Chemical Co. (Rockford, Ill.).

Additional useful linking agents are hydrazines or hydrazine derivatives, compounds that are very soluble in water and soluble in alcohol. Hydrazines are corrosive and strong reducing agents, though they constitute weaker bases than ammonia. Hydrazines are dibasic and form many salts, e.g., mono- and di-hydrochlorides, mono- and di-nitrates, and two sulfates. The hydrazine resin has been found to be a novel and highly useful platform for polyamide synthesis. The hydrazine resin is stable to elevated coupling temperatures, yet is cleaved rapidly at moderate temperatures by a wide range of nucleophiles following a mild and selective oxidation protocol.

Additional compounds and processes, particularly those involving a Schiff base as an intermediate, for conjugation of proteins to other proteins or to other compositions, for example, to reporter groups or to chelators for metal ion labeling of a protein, are disclosed in EP 243,929 A2 (published Nov. 4, 1987).

Photosensitizers which contain carboxyl groups can be joined to lysine s-amino groups in target polypeptides either by preformed reactive esters (such as N-hydroxy succinimide ester) or esters conjugated in situ by a carbodiimide-mediated reaction. The same applies to photosensitizers that contain sulfonic acid groups, which can be transformed to sulfonyl chlorides, which react with amino groups. Photosensitizers that have carboxyl groups can be joined to amino groups on the polypeptide by an in situ carbodiimide method or by hydrazine or hydrazine derivatives. Photosensitizers can also be attached to hydroxyl groups, of serine or threonine residues or to sulfhydryl groups, of serine or threonine residues or to sulfhydryl groups of cysteine residues.

Methods of joining components of a composition can use heterobifunctional cross linking reagents. These agents bind a functional group in one chain and a different functional group in a second chain. These functional groups typically are amino, carboxyl, sulfhydryl, and aldehyde. There are many permutations of appropriate moieties that will react with these groups and with differently formulated structures, to join them together (described in the Pierce Catalog and Merrifield et al. (1994) Ciba Found Symp. 186:5-20).

Generally, the photosensitizer compositions of the invention can be prepared by linking the photosensitizer to another photosensitizer, a binder, a targeting moiety, and/or a backbone using methods described in the following Examples or by methods known in the art. A variety of linkers can be used for covalent conjugation.

Yield from linking reactions can be assessed by spectroscopy of product eluting from a chromatographic fractionation in the final step of purification using known methods. The presence of unlinked photosensitizer and reaction products containing the photosensitizer can be followed by the physical property that the photosensitizer absorbs light at a characteristic wavelength and extinction coefficient, so incorporation into products can be monitored by absorbance at that wavelength or a similar wavelength. Linking of one or more photosensitizer molecules to another photosensitizer, a binder, a targeting moiety or a backbone, shifts the peak of absorbance in the elution profile in fractions eluted using sizing gel chromatography, e.g., with the appropriate choice of Sephadex G50, G100, or G200 or other such matrices (Pharmacia-Biotech, Piscataway N.J.). Choice of appropriate sizing gel, for example Sephadex gel, can be determined by that gel in which the photosensitizer elutes in a fraction beyond the excluded volume of material too large to interact with the bead, i.e., the uncoupled starting photosensitizer composition interacts to some extent with the fractionation bead and is concomitantly retarded to some extent.

Determining which gel to use can be predicted from the molecular weight of the uncoupled photosensitizer. The successful reaction products of photosensitizer compositions coupled to additional moieties generally have characteristic higher molecular weights, causing them to interact with the chromatographic bead to a lesser extent, and thus appear in fractions eluting earlier than fractions containing the uncoupled photosensitizer substrate. Unreacted photosensitizer substrate generally appears in fractions characteristic of the starting material, and the yield from each reaction can thus be assessed both from size of the peak of larger molecular weight material, and the decrease in the peak of characteristic starting material. The area under the peak of the product fractions is converted to the size of the yield using the molar extinction coefficient.

The product can be analyzed using NMR, integrating areas of appropriate product peaks, to determine relative yields with different linkers. A red shift in absorption of a photosensitizer of several nm has often been observed following coupling to a polyamino acid. Linking to a larger moiety such as a protein might produces a comparable shift, as linking to an antibody resulted in a shift of about 3-5 nm in that direction compared to absorption of the free photosensitizer. Relevant absorption maxima and extinction coefficients in 0.1M NaOH/1% SDS are, for chlorin e6, 400 nm and 150,000 $M^{-1}$, $cm^{-1}$, and for benzoporphyrin derivative, 430 nm and 61,000 $M^{-1}$, $cm^{-1}$.

The linker (L) can comprise at least one beta-lactam ring moiety or a fragment or derivative thereof which forms a beta-lactamase cleavable site.

In particular aspects, the linker (L) comprises a beta-lactam antibiotic, or functional derivative or fragment thereof which is cleavable by a beta-lactamase enzyme or fragment thereof. The beta-lactam antibiotic (or functional derivative or fragment thereof) can be any suitable beta-lactam antibiotic which is obtained from any natural, commercial or synthetic source.

In one aspect, the linker (L) comprises a penicillin or fragment thereof having the general known core nucleus structure:

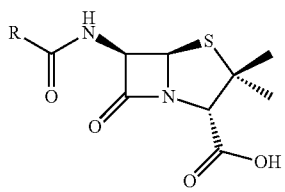

and which is selected from: a narrow spectrum penicillin, such as, benzathine penicillin, benzylpenicillin (penicillin G), phenoxymethylpenicillin (penicillin V), procaine penicillin, and oxacillin; a narrow spectrum penicillinase-resistant penicillin, such as, methicillin, dicloxacillin, and flucloxacillin; a narrow spectrum beta-lactamase-resistant penicillin, such as, temocillin; a moderate spectrum penicillin, such as, amoxicillin and ampicillin; a broad spectrum penicillin, such as, co-amoxiclav; and an extended spectrum penicillin, such as, carboxypenicillins, ureidopenicillins, azlocillin, carbenicillin, ticarcillin, mezlocillin and piperacillin, or any fragment or derivative of a penicillin, and wherein R corresponds to the different moieties of the above indicated penicillins.

In another aspect, the linker (L) comprises a cephalosporin having the general known core nucleus structure:

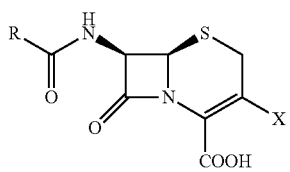

and which is selected from: a first generation cephalosporin, such as, Cefacetrile (cephacetrile), Cefadroxil (cefadroxyl; Duricef®), Cefalexin (cephalexin; Keflex®), Cephaloglycin, Cefalonium (cephalonium), Cefaloridine (cephaloradine), Cefalotin (cephalothin; Keflin®), Cefapirin (cephapirin; Cefadryl®), Cefatrizine, Cefazaflur, Cefazedone, Cefazolin (cephazolin; Ancef®, Kefzol®), Cefradine (cephradine; Velosef®), Cefroxadine, Ceftezole; a second generation cephalosporin, such as, Cefaclor (e.g., Ceclor®, Distaclor®, Keflor®, Raniclor®), Cefonicid (e.g, Monocid®), Cefprozil (e.g., cefproxil; Cefzil®), Cefuroxime (e.g., Zinnat®, Zinacef®, Ceftin®, Biofuroksym®), Cefuzonam, Cefmetazole, Cefotetan, Cefoxitin, Carbacephems (e.g., loracarbef (Lorabid®)), Cephamycins (e.g., cefbuperazone, cefmetazole (Zefazone®), cefminox, cefotetan (Cefotan®), cefoxitin (Mefoxin®)); a second generation cephamycin, such as, cefotetan or cefoxitin; a third generation cephalosporin, such as, Cefcapene, Cefdaloxime, Cefdinir (Omnicef®), Cefditoren, Cefetamet, Cefixime (Suprax®), Cefmenoxime, Cefodizime, Cefotaxime (Claforan®), Cefpimizole, Cefpodoxime (Vantin®, PECEF), Cefteram, Ceftibuten (Cedax), Ceftiofur, Ceftiolene, Ceftizoxime (Cefizax®), Ceftriaxone (Rocephin®), Cefoperazone (Cefobid), Ceftazidime (Fortum®, Fortaz®), or Oxacephems (e.g. latamoxef); or a fourth generation cephalosporin, such as, cefepime (Maxipime®), cefclidine, cefluprenam, cefoselis, cefozopran, cefpirome, or cefquinome, or cefpirome, or any fragment or derivative of a cephalosporin, wherein the R and X correspond to the different moieties of the above indicated cephalosporins.

In another aspect, the linker (L) can also be a carbapenem, such as, imipenem, meropenem, ertapenem, faropenem, or doripenem, or any fragment or derivative of a carbapenem.

In a particular aspect, the linker (L) of the invention comprises a cephalosporin, or fragment or derivative thereof. The photosensitizer compositions of the invention can comprise a cephalosporin linker (or fragment and/or derivative thereof) coupling two photosensitizers in accordance with the following structure:

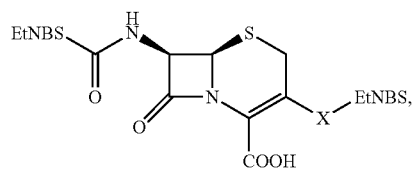

wherein X can be any known cephalosporin substituent or derivative thereof, and wherein EtNBS is benzophenothiazinium chloride.

In another particular embodiment, the present invention provides a photosensitizer composition comprising a cephalosporin linker (or fragment and/or derivative thereof) coupling two benzophenothiazinium chloride (EtBNBS) photosensitizers in accordance with the following structure:

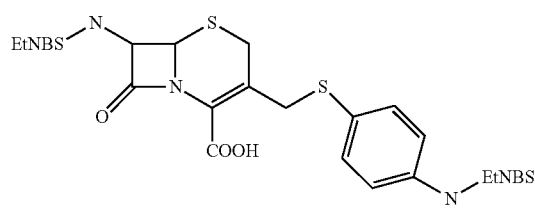

The cephalosporin linker may be any cephalosporin known in the art, such as those listed above, or any functional derivative or fragment thereof. One of ordinary skill in the art will appreciate that there are numerous known methods and chemical approaches for preparing and obtaining fragments and derivatives of cephalosporins, some of which are disclosed in U.S. Pat. No. 6,599,893 (to Glinka), U.S. Pat. No. 6,093,712 (to Matiskella), U.S. Pat. No. 5,827,845 (to Shiokawa et al.) and U.S. Pat. No. 6,329,363 (to Dahnke), each of which are incorporated in their entireties herein by reference.

Specific combinations of linker and photosensitizer contemplated according to the invention include, but are not limited to cephalosporin with two EtNBS photosensitizers; cephalosporin with EtBNS and a black hole quencher (e.g., such as BHQ-3); cephalosporin with Cy3 and Cy5; cephalosporin with Cy5 and a black hole quencher; and cephalosporin with Oregon Green and Texas Red. These specific combination of photosensitizer and linker can be readily made by one of skill in the art according to the methods described herein.

Binders

The photosensitizer compositions of the invention can also include one or more binders. The binder, without limitation, may be a peptide, a cyclic peptide, a polypeptide, a peptidomimetic, a protein, a fusion protein, a hybrid molecule, another photosensitizer or a dimer, multimer, or a conjugate of the above that binds or quenches, and, thus, may inhibit, suppress, neutralize, or decrease activity of, the photosensitizer. The binder may also include, without limitation, a naturally occurring inhibitor, a receptor, a soluble receptor, an antibody, a polyclonal antibody, a monoclonal antibody, a bispecific antibody, an antibody fragment, a single chain antibody, anti-idiotype antibodies, a peptabody, a peptide, an oligopeptides, an oligonucleotide, a cyclic peptide (i.e., a peptide that is circular in nature), a peptide-lipid conjugate, a hormone, an antigen, an epitope, a receptor, a chemokine, a nucleic acid, a ligand or a dimer, multimer, or a conjugate of the above. Naturally occurring binders are binders that quench the photosensitizer and are found in nature.

In one aspect, the binder comprises a fluorophore. The property that renders a fluorophore (or any other binder) a suitable quencher is the capability of absorbing energy from the activated or activatable photosensitizer.

Fluorophores of the present invention can be any known in the art, including photosensitizers, fluorescent dyes, and photoactive dyes.

Photosensitizer binders can be any known in the art, as previously described. For example, hematoporphyrin derivatives have been used as fluorescent probes to investigate the development of human atherosclerotic plaques (Spokojny (1986) J. Am. Coll. Cardiol. 8:1387-1392). A photosensitizer acting as a binder can have a different excitation wavelength than a photosensitizer acting to produce a cytotoxic effect on a pathogen or host cell infected with a pathogen.

Fluorescent dyes, which can be used as photosensitizers or binders of the invention, can be any known in the art, including, but not limited to 6-carboxy-4',5'-dichloro-2',7'-dimethoxyfluorescein succinimidyl ester; 5-(and -6)-carboxyeosin; 5-carboxyfluorescein; 6-carboxyfluorescein; 5-(and -6)-carboxyfluorescein; 5-carboxyfluorescein-bis-(5-carboxymethoxy-2-nitrobenzyl)ether, -alanine-carboxamide, or succinimidyl ester; 5-carboxyfluorescein succinimidyl ester; 6-carboxyfluorescein succinimidyl ester; 5-(and -6)-carboxyfluorescein succinimidyl ester; 5-(4,6-dichloro-triazinyl)aminofluorescein; 2',7'-difluorofluorescein; eosin-5-isothiocyanate; erythrosin-5-isothiocyanate; 6-(fluorescein-5-carboxamido) hexanoic acid or succinimidyl ester; 6-(fluorescein-5-(and -6)-carboxamido) hexanoic acid or succinimidyl ester; fluorescein-5-EX succinimidyl ester; fluorescein-5-isothiocyanate; fluorescein-6-isothiocyanate; Oregon Green® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidyl ester or triethylammonium salt; Oregon Green® 514 carboxylic acid; Oregon Green® 514 carboxylic acid or succinimidyl ester; Rhodamine Green™ carboxylic acid, succinimidyl ester or hydrochloride; Rhodamine Green™ carboxylic acid, trifluoroacetamide or succinimidyl ester; Rhodamine Green™-X succinimidyl ester or hydrochloride; Rhodol Green™ carboxylic acid, N,O-bis-(trifluoroacetyl) or succinimidyl ester; bis-(4-carboxypiperidinyl) sulfonerhodamine or di(succinimidyl ester); 5-(and -6)-carboxynaphthofluorescein, 5-(and -6)-carboxynaphthofluorescein succinimidyl ester; 5-carboxyrhodamine 6G hydrochloride; 6-carboxyrhodamine 6G hydrochloride, 5-carboxyrhodamine 6G succinimidyl ester; 6-carboxyrhodamine 6G succinimidyl ester; 5-(and -6)-carboxyrhodamine 6G succinimidyl ester; 5-carboxy-2',4',5',7'-tetrabromosulfonefluorescein succinimidyl ester or bis-(diisopropylethylammonium) salt; 5-carboxytetramethylrhodamine; 6-carboxytetramethylrhodamine; 5-(and -6)-carboxytetramethylrhodamine; 5-carboxytetramethylrhodamine succinimidyl ester; 6-carboxytetramethylrhodamine succinimidyl ester; 5-(and -6)-carboxytetramethylrhodamine succinimidyl ester; 6-carboxy-X-rhodamine; 5-carboxy-X-rhodamine succinimidyl ester; 6-carboxy-X-rhodamine succinimidyl ester; 5-(and -6)-carboxy-X-rhodamine succinimidyl ester; 5-carboxy-X-rhodamine triethylammonium salt; Lissamine™ rhodamine B sulfonyl chloride; malachite green isothiocyanate; NANOGOLD® mono(sulfosuccinimidyl ester); QSY® 21 carboxylic acid or succinimidyl ester; QSY® 7 carboxylic acid or succinimidyl ester; Rhodamine Red™-X succinimidyl ester; 6-(tetramethylrhodamine-5-(and -6)-carboxamido)hexanoic acid succinimidyl ester; tetramethylrhodamine-5-isothiocyanate; tetramethylrhodamine-6-isothiocyanate; tetramethylrhodamine-5-(and -6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; or X-rhodamine-5-(and -6)-isothiocyanate.

Fluorescent dyes can also include, for example, bodipy dyes commercially available from Molecular Probes, including, but not limited to BODIPY® FL (4,4-difluoro-5,7-dimethyl-4-bora-3a,4a-diaza-s-indacene-3-propionic acid, succinimidyl ester); BODIPY® TMR STP ester; BODIPY® TR-X STP ester; BODIPY® 630/650-X STP ester; BODIPY® 650/665-X STP ester (6-(((4,4-difluoro-5-(2-pyrrolyl)-4-bora-3a,4a-diaza-s-indacene-3-yl)styryloxy) acetyl)aminohexanoic acid, succinimidyl ester); 6-dibromo-4,4-difluoro-5, 7-dimethyl-4-bora-3a,4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoic acid; 4,4-difluoro-5,7-dimethyl-4-bora-3a,4a-diaza-s-indacene-3-pentanoic acid succinimidyl ester; 4,4-difluoro-5,7-dimethyl-4-bora-3a,4a-diaza-s-indacene-3-propionic acid; 4,4-difluoro-5,7-dimethyl-4-bora-3a,4a-diaza-s-indacene-3-propionic acid succinimidyl ester; 4,4-difluoro-5,7-dimethyl-4-bora-3a,4a-diaza-s-indacene-3-propionic acid sulfosuccinimidyl ester or sodium salt; 6-((4,4-difluoro-5,7-dimethyl-4-bora-3a,4a-diaza-s-indacene-3-propionyl) amino)hexanoic acid; 6-((4,4-difluoro-5,7-dimethyl-4-bora-3a,4a-diaza-s-indacene-3-propionyl)amino)hexanoic acid or succinimidyl ester; N-(4,4-difluoro-5,7-dimethyl-4-bora-3a,4a-diaza-s-indacene-3-propionyl)cysteic acid, succinimidyl ester or triethylammonium salt; 6-4,4-difluoro-1,3-dimethyl-5-(4-methoxyphenyl)-4-bora-3a,4a 4,4-difluoro-5,7-diphenyl-4-bora-3a,4a-diaza-s-indacene-3-propionic acid; 4,4-difluoro-5,7-diphenyl-4-bora-3a,4a-diaza-s-indacene-3-propionic acid succinimidyl ester; 4,4-difluoro-5-phenyl-4-bora-3a,4a-diaza-s-indacene-3-propionic acid succinimidyl ester; 6-((4,4-difluoro-5-phenyl-4-bora-3a,4a-diaza-s-indacene-3-propionyl)amino)hexanoic acid or succinimidyl ester; 4,4-difluoro-5-(4-phenyl-1, 3-butadienyl)-4-bora-3a,4a-diaza-s-indacene-3-propionic acid succinimidyl ester; 4,4-difluoro-5-(2-pyrrolyl)-4-bora-3a,4a-diaza-s-indacene- 3-propionic acid succinimidyl ester; 6-(((4,4-difluoro-5-(2-pyrrolyl)-4-bora-3a,4a-diaza-s-indacene-3-yl)styryloxy) acetyl)aminohexanoic acid or succinimidyl ester; 4,4-difluoro-5-styryl-4-bora-3a,4a-diaza-s-indacene-3-propionic acid; 4,4-difluoro-5-styryl-4-bora-3a,4a-diaza-s-indacene-3-propionic acid succinimidyl ester; 4,4-difluoro-1,3,5,7-tetramethyl-4-bora-3a,4a-diaza-s-indacene-8-propionic acid; 4,4-difluoro-1,3,5,7-tetramethyl-4-bora-3a, 4a-diaza-s-indacene-8-propionic acid succinimidyl ester; 4,4-difluoro-5-(2-thienyl)-4-bora-3a,4a-diaza-s-indacene-3-propionic acid succinimidyl ester; 6-(((4-(4,4-difluoro-5-(2-thienyl)-4-bora-3a,4a-diaza s-indacene-3-yl)phenoxy) acetyl) amino)hexanoic acid or succinimidyl ester; and 6-(((4,4-difluoro-5-(2-thienyl)-4-bora-3a,4a-diaza-s-indacene-3-yl)styryloxy)acetyl)aminohexanoic acid or succinimidyl ester.

Fluorescent dyes of the present invention can also be, for example, alexa fluor dyes commercially available from Molecular Probes, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 647 carboxylic acid; Alexa Fluor® 660 carboxylic acid; or Alexa Fluor® 680 carboxylic acid.

Fluorescent dyes of the present invention can also be, for example, cy dyes commercially available from Amersham-Pharmacia Biotech, including, but not limited to Cy3 NHS ester; Cy 5 NHS ester; Cy5.5 NHS ester; and Cy 7 NHS ester.

Photoactive dyes, which can also be used as binders or photosensitizers of the invention, can be any photosensitizer known in the art which will fluoresce but will not necessarily produce a reactive species in phototoxic amounts when illuminated. Depending on the wavelength and power of light administered, a photosensitizer can be activated to fluoresce and, therefore, act as a photoactive dye, but not produce a phototoxic effect unless, in some cases, the wavelength and power of light is suitably adapted to induce a phototoxic effect.

Throughout this specification, any reference to a binder should be construed to refer to each of the binders identified and contemplated herein and to each biologically equivalent molecule. "Biologically equivalent" means compositions of the present invention which are capable of preventing action of the photosensitizer in a similar fashion, but not necessarily to the same degree.

Targeting Moieties

The inventive photosensitizer compositions of the invention also contemplate being coupled to one or more targeting moieties, which increase the specificity of the photosensitizer composition for its target, and can be used for a variety of purposes, including, for example, targeting the photosensitizer composition of the invention to reach a closer proximity to the target cells or enzymes (e.g., beta-lactamase) which are of interest to be assayed or measured. Targeting moieties include antibody and antibody fragments, peptides, and hormones. In one aspect of the invention, the targeting moiety can be a polypeptide (e.g., a human polypeptide such as poly-lysine or serum albumin). Alternatively, the targeting moiety can be a small anti-microbial peptide (SAMPs) (i.e., a peptide containing less than 60 amino acid residues), such as, for example, histatins, defensins, cecropins, magainins, Gram positive bacteriocins, and peptide antibiotics. Many SAMP's are in the range of 20-40 amino acid residues in length. SAMP's are naturally occurring peptides, and are made by a wide variety of organisms. Many SAMP's have a broad spectrum of antimicrobial activity, and, e.g., can kill more than one species, and in some cases can kill distantly related species, e.g. Gram negative and Gram positive bacterial species.

The targeting moiety can bind to a defined population of cells. In various aspects, it can bind a receptor, an oligonucleotide, an enzymatic substrate, an antigenic determinant, or other binding site present on or in the target cell population. Accordingly, the targeting moiety can be a molecule or a macromolecular structure that targets specific cells, for example, macrophages, or that interacts with a pathogen. Some photosensitizers target macrophages directly (see, e.g., Korbelik et al., Cancer Res. 51:2251-2255, 1991).

Moieties, either alone or when incorporated into a conjugate, as in a supramolecular structure (e.g., a liposome, a micelle, a lipid vesicle, or the like), can be used to specifically target macrophages by certain receptors. Thus, a ligand for such receptors can be used as a targeting moiety. For example, the following receptors can be used to target macrophages: the complement receptor (Rieu et al., J. Cell Biol. 127:2081-2091, 1994), the scavenger receptor (Brasseur et al., Photochem. Photobiol. 69:345-352, 1999; Suzuki et al., Nature 386:292-296, 1997; Sarkar et al., Mol. Cell. Biochem. 156:109-116, 1996), the transferrin receptor (Dreier et al., Bioconjug. Chem. 9:482-489, 1998; Hamblin et al., J. Photochem. Photobiol. 26:4556, 1994; Clemens et al., J. Exp. Med. 184:1349-1355, 1996), the Fc receptor (Rojanasakul et al., Pharm. Res. 11:1731-1733, 1994; Harrison et al., Pharm Res. 11:1110-4, 1994). The mannose receptor is particularly important for macrophage recognition of foreign material and has been used successfully to target molecules to macrophages (Frankel et al., Carbohydr. Res. 300:251-258, 1997; Chakrabarty et al., J. Protozool. 37:358-364, 1990; Mistry et al., Lancet 348:1555-1559, 1996; Liang et al., Biochim. Biopys. Acta 1279:227-234, 1996; Sarkar et al., Mol. Cell. Biochem. 156:109-116, 1996). Toll or toll-like receptors are also present on macrophages and are useful targets (Brightbill et al., Science 285:732-736, 1999).

The photosensitizer compositions of the invention can comprise targeting moieties which target the former to macrophages. Such targeting moieties can include low density lipoproteins (Mankertz et al., Biochem. Biophys. Res. Commun. 240:112-115, 1997; von Baeyer et al., Int. J. Clin. Pharmacol. Ther. Toxicol. 31:382-386, 1993), very low density lipoproteins (Tabas et al., J. Cell Biol. 115:1547-1560, 1991), mannose residues (as mentioned above) and other carbohydrate moieties (Pittet et al., Nucl. Med. Biol. 22:355-365, 1995), poly-cationic molecules (e.g., poly-Llysine; Hamblin et al., J. Photochem. Photobiol. 26:45-56, 1994), emulsions (Khopade et al., Pharmazie 51:558-562, 1996), aggregated albumin (Hamblin et al., J. Photochem. Photobiol. 26:45-56, 1994), biodegradable microspheres (Oettinger et al., J. Interferon Cytokine Res. 19:33-40, 1999), non-biodegradable microspheres (Schroder, Methods Enzymol 112:116-128, 1985), nanoparticles (Lobenberg et al., AIDS Res. Hum. Retroviruses 12:1709-1715, 1996); Venier-Julienne et al., J. Drug Target. 3:23-29, 1995; Schafer et al., J. Microencapsul. 11:261-269, 1994; Gaspar et al., Ann. Trop. Med. Parasitol 86:41-49, 1992), liposomes (Bakker-Woudenberg et al. J. Drug Target. 2:363-371, 1994; Meyers et al., Exp. Lung Res. 19:1-19, 1993; Betageri et al., J. Pharm. Pharmacol. 45:48-53, 1993; Muller et al., Biochim. Biophys. Acta. 986:97-105, 1989; Kole et al., J. Infect.

Dis. 180:811-820, 1999), macrophage-specific cytokines (Biragyn et al., Nat. Biotechnol. 17:253-258, 1999; Chan et al., Blood 86:2732-2740, 1995), erythrocytes (Magnani et al., J. Leukoc. Biol. 185:717-730, 1997), antibodies recognizing components of the tuberculous phagosome like Nrampl (Gruenheid et al., J. Exp. Med. 185:717-730, 1997), a 2-macroglobulin (Chu et al., J. Immunol. 152:1538-1545, 1994).

A targeting moiety can be directed to a pathogen. In addition, certain structural features of enzymes can be targeted, such as the hydrophobic pocket of the *Mycobacterium tuberculosis* enzyme inhA (Dessen, et al. (1995) Science 267:1638-1641). Alternatively, host molecules that target the bacteria, such as anti-microbial peptides (e.g., granulysin), can be used in photosensitizer compositions of the invention (Stenger et al., Science 282:121-125, 1998).

A targeting moiety can be used alone or in combination, particularly to target both macrophages and the intracellular pathogen. Manipulations of the host cell can also complement the photosensitizer (Collins et al., J. Cell Sci. 110:191-200, 1997; Korbelik et al., Br. J. Cancer 75:202-207, 1997; Krosl et al., Cancer Res. 56:3281-3286, 1996).

The targeting moiety can be a polypeptide. The polypeptide may be linear, branched, or cyclic. The targeting moiety can include a polypeptide having an affinity for a polysaccharide target, for example, a lectin (such as a seed, bean, root, bark, seaweed, fungal, bacterial, or invertebrate lectin). Particularly useful lectins include concanavalin A, which is obtained from jack beans, and lectins obtained from the lentil, *Lens culinaris*.

Desirable characteristics for the targeting moieties include: specificity for one or more unwanted target organisms or components thereof (e.g. cell surface receptors), affinity and avidity for such organisms, and stability with respect to conditions of coupling reactions and the physiology of the organ or tissue of use. Specificity need not be narrowly defined, e.g., it may be desirable for a targeting molecule to have affinity for a broad range of target organisms, such as all Gram negative bacteria. The targeting moiety, when incorporated into a composition of the invention, should be nontoxic to the cells of the subject.

Targeting moieties can be selected from the sequences of naturally occurring proteins and peptides, from variants of these peptides, and from biologically or chemically synthesized peptides. Naturally occurring peptides which have affinity for one or more target organism can provide sequences from which additional peptides with desired properties, e.g., increased affinity or specificity, can be synthesized individually or as members of a library of related peptides. Such peptides can be selected on the basis of affinity for the target organism.

Naturally occurring peptides with affinity for target organisms useful in methods and compounds of the invention include, aptomers, salivary proteins, e.g., histatins, microbially-elaborated proteins, e.g., bacteriocins, peptides that bind and/or kill species that are closely related to the producing strains; and proteins produced by animal species, such as defensins, which are produced by mammals, and the cecropins and magainins, produced by moths and amphibia, respectively.

As mentioned briefly above, histatins, defensins, cecropins and magainins are examples of a class of polypeptides found widely in nature, which share the characteristics of small size (generally approximately 30 amino acid residues, and between 10 residues and 50 residues), broad specificity of anti-microbial activity, and low affinity for target organisms.

Histatins are a family of histidine-rich cationic polypeptides which have bactericidal and candidacidal properties and are constituents of normal human saliva (Oppenheim, G. G. et al., J. Biol. chem. 263:7472-747, 1988). Their mechanism of action is thought to involve a combination of alpha-helical conformation and cationic charge leading them to insert between the polar head groups in the bacterial cell wall (Raj, P. A. et al., J. Biol. Chem. 269:9610-9619, 1994).

Bacteriocins, which are proteins produced by bacteria and which kill other strains and species of bacteria (Jack, R. W. et al., Microbiol. Rev. 59:171-200, 1995) can be used as targeting moieties. An exemplary Gram positive bacteriocin is nisin, produced by *Lactococcus* lactis and accorded GRAS status (generally regarded as safe) by the Food and Drug Administration for application to food preservation.

The bacteriocins, nisin, subtilin, epidermin, gallidermin, salivarin, and lacticin exemplify the "lantibiotic" class of Gram positive bacteriocins, which is defined as those bacteriocins in which one or more cysteine residues are linked to a dehydrated serine or threonine to form a thioether-linked residue known as lanthionine (Lan) or threo-β-methyllanthionine (MeLan). These are post-translational modifications found in these anti-microbial peptides by the producing cell. Lantibiotics contain leader peptide sequences of 18-24 residues, which are cleaved to yield an active antimicrobial peptide of about 22-35 residues. Growth of the producing bacterial species, and preparation and purification of bacteriocins are performed by published procedures and techniques which can be carried out by one of skill in the art. For example, Yang, R. et al., Appl. and Env. Microbiol 58: 3355-3359, 1992, describe purification of bacteriocins from each of 4 genera of lactic acid bacteria, by optimizing absorption onto the producing cells, followed by use of low pH for selective elution of greatly enriched bacteriocin fractions. Mutant forms of each of the bacteriocins, nisin, produced by *Lactococcus* lactis, and subtilin, produced by *Bacillus subtilis* have more desirable properties than the parental wild-type forms (Liu, W. and N. Hansen, J. Biol. Chem. 267:25,078-25,085, 1992). Procedures for isolation of appropriate genes and for mutagenesis and selection of strains carrying desirable mutations are found in Maniatis, T. et al, 1982, Molecular Cloning: a Laboratory Manual, Cold Spring Harbor Press, Cold Spring Harbor, N.Y., and in the subsequent second edition, Sambrook, J. et al., 1989.

Anti-microbial peptides are produced by a variety of animals (Saberwal, G. and R. Nagaraj, Biochim. Biophys. Act. 1197:109-131, 1994). An example is a peptide of the cecropin family produced by Cecropia moths. Several cecropins contain 37 residues, of which 6 are lysine. Cecropins are active against both Gram positive and Gram negative bacteria. Other insect-produced peptides include apidaecin (from honeybees), andropin (from fruit flies), and cecropin family members from bumble bees, fruit flies, and other insects.

The defensins are produced by mammals, including humans, and are generally about 29-34 residues in length, and the magainins (about 23 residues) are produced by amphibia such as *Xenopus laevis*. Defensins from human (HNP-1, -2, -3 and 4), guinea pig (GPNP), rabbit (NP-1, -2, -3A, -3B, -4 and -5) and rat (NP-1, -2, -3 and -4) share a significant number of regions of homology. Defensins can have antimicrobial activity against Gram positive bacteria or Gram negative bacteria and fungi, with minimal inhibitory concentrations in the mM range. Rabbit NP-1 and NP-2 are more potent antibacterial agents than others in this family. Other mammalian anti-microbial peptides include murine cryptdin, bovine granulocyte bactenecin and indolicidin, and seminal-plasmin from bovine semen. Additional amphibial anti-microbials include PGLA, XPF, LPF, CPG, PGQ, bombinin from Bombina variegata, the bombinin-like peptides BLP-1, -2, -3 and -4 from *B. orientalis*, and brevinins from Rana esculenta. Invertebrates such as the horseshoe crab can be a source of anti-microbial peptides such as the tachyplesins (I, II and III) and the polyphemusins (I and II).

Peptides in these families of antimicrobial agents are generally cationic, and can have a broad antimicrobial spectrum, including both antibacterial and antifungal activities. The addition of positively charged residues can enhance antimicrobial specific activity several fold. The positive charges are thought to assist in the insertion of the peptides into the membranes of the susceptible organisms, in which context the peptide molecules can form pores and cause efflux of ions and other metabolites. Structural studies of the Moses sole fish neurotoxin 33 residue peptide pardaxin, for example, reveals that succinylated pardaxin inserts into erythrocyte and model membranes more slowly than unmodified pardaxin. (Shai, Y et al., J. Biol. Chem. 265: 20, 202-20, 209, 1990). The positively charged magainin molecule can disrupt both the metabolism of *E. coli* and the electric potential of the mitochondrion (Westerhoff, H. V., et al., Proc. Natl. Acad. Sci. 86:6597-6601, 1989).

Novel peptides, for example, a cecropin-melittin hybrid, and synthetic Denantiomers, have antimicrobial activity (Merrifield, R. B. et al., "Antimicrobial peptides," Ciba Foundation Symp. 186, John Wiley, Chichester, pp. 5-26, 1994). One such synthetic cecropin-melittin peptide is 5-fold more active against *Mycobacterium smegmatis* than rifampin.

Targeting moieties can be plant proteins with affinities for particular target organisms, for example, a member of the lectin protein family with affinity for polysaccharides. Targeting moieties can be synthetic peptides, such as polylysine, polyarginine, polyomithine, and synthetic heteropolypeptides that comprise substantial proportions of such positively charged amino acid residues. Such peptides can be chemically synthesized or produced biologically in recombinant organisms, in which case the targeting moiety peptide can be produced as part of a larger protein, for example, as the N-terminus residues, and cleaved from that larger protein. Polypeptides suitable as "backbone" moieties are also suitable as target moieties, if they have sufficient affinity for the target organism. Considerations described are thus appropriate to the general consideration of a targeting moieties.

Targeting moieties need not be limited to peptide compositions, but can be lectins, polysaccharides, steroids, and metalloorganic compositions. Targeting moieties can be comprised of compositions that are composed both of amino acids and sugars, such as mucopolysaccharides. A useful targeting moiety can be partially lipid and partially peptide in nature, such as low density lipoprotein. Serum lipoproteins especially high density and low density lipoproteins (HDL and LDL) can bind to bacterial surface proteins (Emancipator, K. et al., Infect. Immun. 60:596-601, 1992). HDL, and especially reconstituted HDL, neutralizes bacterial lipopolysaccharide both in vitro and in vivo (Wurfel M M et al., J. Exp. Med. 181:1743-1754, 1995). Endogenous LDL can protect against the lethal effects of endotoxin and Gram negative infection (Netea, M., et al., J. Clin. Invest. 97:1366-1372, 1996). The appropriate binding features of the lipoproteins to bacterial surface components can be identified by methods of molecular biology known in the art, and the binding feature of lipoproteins can be used as the targeting moiety in photosensitizer compositions of the present invention.

Molecules, e.g., peptides, other than antibodies and members of a high affinity ligand pairs, can be used to target a photosensitizer composition according to the invention to a target organism. Targeting moieties can be modified or refined. Once an example of a targeting moiety of reasonable affinity has been provided, one skilled in the art can alter the disclosed structure (of a polylysine polypeptide, for example), by producing fragments or analogs, and testing the newly produced structures for modification of affinity or specificity. Examples of methods which allow the production and testing of fragments and analogs are discussed in U.S. Pat. No. 6,462,070.

In aspects pertaining to diagnostic methods, the skilled artisan will appreciate that the targeting moieties described herein can be configured such that they do not interfere with the activation or dequenching of the photosensitizers associated with linker cleavage.

Backbones

Photosensitizer compositions according to the invention include those in which a "backbone" moiety, such as a polyamino acid, is linked to a photosensitizer and/or to a binder and/or to a targeting moiety. Additionally, the backbone can itself be a targeting moiety, e.g. polylysine.

Inclusion of a backbone in a composition with a photosensitizer and/or binder and/or targeting moiety can provide a number of advantages, including the provision of greater stoichiometric ranges of photosensitizers and/or binders and/or targeting moieties coupled per backbone. If the backbone possesses intrinsic affinity for a target organism, the affinity of the composition can be enhanced by coupling to the backbone. Furthermore, the specific range of organisms that can be targeted with one composition can be expanded by coupling two or more different targeting moieties to a single photosensitizer-backbone composition. However, it will be appreciated that in embodiments pertaining to diagnostic methods, the backbone should be configured such that it does not interfere with the activation or dequenching of the photosensitizers following linker cleavage.

Peptides useful in the methods and compounds of the invention for design and characterization of backbone moieties include poly-amino acids which can be homo- and hetero-polymers of L-, D-, racemic DL- or mixed L- and D-amino acid composition, and which can be of defined or random mixed composition and sequence. Examples of naturally-occurring peptides with mixed D and L amino acid residues include bacitracin and tyrocidin. These peptides may be modeled after particular natural peptides, and optimized by the technique of phage display and selection for enhanced binding to a chosen target, so that the selected peptide of highest affinity is characterized and then produced synthetically.

Further modifications of functional groups can be introduced for purposes, for example, of increased solubility, decreased aggregation, and altered extent of hydrophobicity. Examples of non-peptide backbones include nucleic acids and derivatives of nucleic acids, such as: DNA, RNA and peptide nucleic acids; polysaccharides and derivatives such as starch, pectin, chitins, celluloses and hemi-methylated celluloses; lipids such as triglyceride derivatives and cerebrosides; synthetic polymers such as polyethylene glycols (PEGs) and PEG star polymers; dextran derivatives, polyvinyl alcohols, N-(2-hydroxypropyl)-methacrylamide copolymers, poly (DL-glycolic acid-lactic acid); and compositions containing elements of any of these classes of compounds.

Administration of the Photosensitizer Compositions of the Invention

In certain aspects, the photosenstizer compositions of the invention can be used therapeutically, i.e., for photodynamic therapy of bacterial infections. The photosensitizer compositions of the invention can be delivered to a subject in a free form, i.e., in solution. Alternatively the compositions can be delivered in various formulations including, but not limited to, liposome, peptide-bound, polymer-bound, or detergent-containing formulations. Those of ordinary skill in the art are well able to generate and administer such formulations. The composition should be soluble under physiological conditions, in aqueous solvents containing appropriate carriers or excipients, or in other systems, such as liposomes, that may be used to administer the conjugate to a subject.

Photosensitizer compositions that are somewhat insoluble in an aqueous solvent can be applied in a liposome, or a time release fashion, such that illumination can be applied intermittently using a regimen of periods of illumination alternating with periods of non-illumination. Other regimens contemplated are continuous periods of lower level illumination, for which a time-release formulation is suitable.

A composition of the present invention can be administered in a therapeutically effective amount by a variety of methods known in the art, including orally and topically. In one aspect, a photosensitizer composition of the invention may be administered parenterally. The phrase "administered parenterally" as used herein means modes of administration other than oral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and infrasternal injection and infusion. As used herein, a "therapeutically effective amount" refers to that amount of a photosensitizer composition that, when administered to a subject, is sufficient to decrease the activity of a pathogen such that an infection is reduced or alleviated.

As will be appreciated by the skilled artisan, the route and/or mode of administration will vary depending upon the desired results. A photosensitizer composition according to the invention can be contained in a pharmaceutically acceptable excipient or carrier. Included, without limitation, are any and all solvents, dispersion media, coatings, antibacterial and antifungal agents, isotonic and absorption delaying agents, and the like that are physiologically compatible. The use of such media and agents for pharmaceutically active substances is well known in the art. Advantageously, the carrier is suitable for oral, intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

In one aspect, the carrier may protect the compound against rapid release, for example, a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In another aspect of the invention, the photosensitizer compositions can be administered by combination therapy, i.e., combined with other agents. For example, the combination therapy can include a composition of the present invention with at least one other photosensitizer, at least one antibiotic, or other conventional therapy.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

One of ordinary skill in the art can determine and prescribe the effective amount of the pharmaceutical composition as needed. For example, one could start doses of the known or novel photosensitizer composition levels lower than that indicated in order to achieve the desired therapeutic effect and gradually increase the dosage until the desired effect is achieved. For example, the dosage may range from 0.1 mg/kg to 10 mg/kg depending on the therapeutic agent used.

The iterations delineated above are not intended as limiting with respect to the nature of the conjugate photosensitizer compositions of the invention, or to a particular route of the administration.

Photoactivation/Illumination

The photosensitizer compositions of the invention are photoactivated in both therapeutic and diagnostic uses according to the invention. For therapeutic uses, administration of a photosensitizer composition according to the invention is typically followed by a sufficient period of time to allow accumulation thereof at the target site. Upon encountering the target pathogen and/or infected host cell to be treated or evaluated diagnostically, the enzyme cleavage site of the linker is cleaved by enzymes produced by the pathogen. Of note, the enzymes can be secreted by, can be internal to, or can reside on the surface, or within the cell wall space of a pathogen. Once the linker is cleaved, the photosensitizers are rendered in an unquenched state. The photosensitizers can, subsequently, be activated by irradiation. This is accomplished by applying light of a suitable wavelength and intensity, for an effective length of time, at the site of the infection for therapeutic uses, or at the site of reaction for diagnostic uses, e.g., reaction vessel. As used herein, "irradiation" refers to the use of light to induced a chemical reaction of a photosensitizer.

Photoactivating dosages depend on various factors, including the amount of the photosensitizer administered, the wavelength of the photoactivating light, the intensity of the photoactivating light, and the duration of illumination by the photoactivating light. Thus, the dose can be adjusted to a therapeutically effective dose or to a dose suitable for diagnostics by adjusting one or more of these factors. Such adjustments are within the level of ordinary skill in the art.

Irradiation of the appropriate wavelength for a given compound may be administered by a variety of methods. Methods for irradiation include, but are not limited to, the administration of laser, nonlaser, or broad band light. Irradiation can be produced by extracorporeal or intraarticular generation of light of the appropriate wavelength. Light used in the invention may be administered using any device capable of delivering the requisite power of light including, but not limited to, fiber optic instruments, arthroscopic instruments, or instruments that provide transillumination.

With therapeutic embodiments, delivery of the light to a recessed, or otherwise inaccessible physiological location can be facilitated by flexible fiber optics (implicit in this statement is the idea that one can irradiate either a broad field, such as the lung or a lobe of the lung, or a narrow field where bacterial cells may have localized).

The photosensitizer compositions of the invention, in some aspects, can be stable during the course of at least a single round of treatment or diagnostic use (e.g., detection of and/or quantitation of beta-lactamase activity) by continued or pulsed irradiation, during which the photosensitizer within the composition would, advantageously, be repeatedly excited to the energized state, undergoing multiple rounds of generation of singlet oxygen.

The suitable wavelength, or range of wavelengths, will depend on the particular photosensitizer(s) used, and can range from about 350 nm to about 550 nm, from about 550 nm to about 650 nm, from about 650 nm to about 750 nm, from about 750 nm to about 850 nm and from about 850 nm to about 950 nm.

In some aspects, target tissues are illuminated with red light. Given that red and/or near infrared light best penetrates mammalian tissues, photosensitizers with strong absorbances in the range of about 600 nm to about 900 nm can be suitable for activation of administered photosensitizers of the invention. For photoactivation, the wavelength of light is matched to the electronic absorption spectrum of the photosensitizer so that the photosensitizer absorbs photons and the desired photochemistry can occur. Wavelength specificity for photoactivation generally depends on the molecular structure of the photosensitizer. Photoactivation can also occur with sub-ablative light doses. Determination of suitable wavelength, light intensity, and duration of illumination is within ordinary skill in the art.

With therapeutic uses, the effective penetration depth, $\delta_{eff}$, of a given wavelength of light is a function of the optical properties of the tissue, such as absorption and scatter. The fluence (light dose) in a tissue is related to the depth, d, as: $e^{-d/\delta_{eff}}$. Typically, the effective penetration depth is about 2 to 3 mm at 630 nm and increases to about 5 to 6 nm at longer wavelengths (about 700 to about 800 nm) (Svaasand and Ellingsen, (1983) Photochem Photobiol. 38:293-299). Altering the biologic interactions and physical characteristics of the photosensitizer can alter these values. In general, photosensitizers with longer absorbing wavelengths and higher molar absorption coefficients at these wavelengths are more effective photodynamic agents.

The light for photoactivation can be produced and delivered to the site of infection or to a diagnostic reaction by any suitable means known in the art. Photoactivating light can be delivered from a light source, such as a laser or optical fiber. Optical fiber devices that directly illuminate the site of inflammation or a diagnostic reaction can deliver the photoactivating light. For example, for therapeutic uses, the light can be delivered by optical fibers threaded through small gauge hypodermic needles. Light can be delivered by an appropriate intravascular catheter, such as those described in U.S. Pat. Nos. 6,246,901 and 6,096,289, which can contain an optical fiber. Optical fibers can also be passed through arthroscopes. In addition, light can be transmitted by percutaneous instrumentation using optical fibers or cannulated waveguides. For open surgical sites, suitable light sources include broadband conventional light sources, broad arrays of light-emitting diodes (LEDs), and defocused laser beams.

Delivery can be by all methods known in the art, including transillumination. Some photosensitizers can be activated by near infrared light, which penetrates more deeply into biological tissue than other wavelengths. Thus, near infrared light is advantageous for transillumination. Transillumination can be performed using a variety of devices. The devices can utilize laser or non-laser sources, (e.g., lightboxes or convergent light beams).

In aspects where treatment is desired, the dosage of photosensitizer composition, and light activating the photosensitizer composition, is administered in an amount sufficient to produce a phototoxic species. For example, where the photosensitizer is chlorin$_{e6}$, administration to humans is in a dosage range of about 0.1 to about 10 mg/kg, preferably about 1 to about 5 mg/kg more preferably about 2 to about 4 mg/kg and the light delivery time is spaced in intervals of about 30 minutes to about 3 days, preferably about 12 hours to about 48 hours, and more preferably about 24 hours. The light dose administered is in the range of about 2-500 J/cm$^2$, preferably about 5 to about 50 J/cm$^2$, and more preferably about 5 to about 10 J/cm$^2$. The fluence rate is in the range of about 20 to about 500 mw/cm$^2$, preferably about 50 to about 300 mw/cm$^2$ and more preferably about 100 to about 200 mw/cm$^2$. There is a reciprocal relationship between photosensitizer compositions and light dose, thus, determination of suitable wavelength, light intensity, and duration of illumination is within ordinary skill in the art.

Dosage regimens can be adjusted to provide the optimum desired response (e.g., a therapeutic response). For example, a single bolus may be administered, several divided doses may be administered over time, or the dose may be proportionally reduced or increased as indicated by the exigencies of the therapeutic situation.

Irradiation of the appropriate wavelength for a given compound for the therapeutic or diagnostic methods of the invention may be administered by a variety of wavelengths. Methods for irradiation include, but are not limited to, the administration of laser, nonlaser, or broad band light. Irradiation can be produced by extracorporeal or intraarticular generation of light of the appropriate wavelength. Light used in the invention may be administered using any device capable of delivering the requisite power of light including, but not limited to, fiber optic instruments, arthroscopic instruments, or instruments that provide transillumination.

The wavelength and power of light can be adjusted according to standard methods known in the art to control the production of phototoxic species or a fluorescence resonse. Thus, under certain conditions (e.g., low power, low fluence rate, shorter wavelength of light or some combination thereof), a fluorescent species is primarily produced from the photosensitizer and any reactive species produced has a negligible effect. These conditions are easily adapted to bring about the production of a phototoxic species. For example, where the photosensitizer is chlorin$_{e6}$, the light dose administered to produce a fluorescent species and an insubstantial reactive species is less than about 10 J/cm, preferably less than about 5 J/cm and more preferably less than about 1 J/cm. Determination of suitable wavelength, light intensity, and duration of illumination for any photosensitizer is within the level of ordinary skill in the art.

In certain aspects directed to diagnostic methods, dequenched or photoactivatable photosensitizers (e.g., following cleavage of linker) can be detected by illuminating the photosensitizers with suitable wavelength of light and then detecting the response (e.g., fluorescence emission).

A sample can be illuminated with a wavelength of light selected to give a detectable optical response, and observed with a means for detecting the optical response. Equipment that is useful for illuminating the present compounds and compositions of the invention includes, but is not limited to, hand-held ultraviolet lamps, mercury arc lamps, xenon lamps, lasers and laser diodes. These illumination sources are optically integrated into laser scanners, fluorescence microplate readers or standard or microfluorometers, or any other suitable known means for detecting and/or measuring the signal (e.g., a fluorescence signal).

The herein disclosed photosensitizers may, at any time after or during an assay, be illuminated with a wavelength of light that results in a detectable optical response, and observed with a means for detecting and measuring the optical response. Upon illumination, such as by an ultraviolet or visible wavelength emission lamp, an arc lamp, a laser, or even sunlight or ordinary room light, the fluorescent compounds, including those bound to the complementary specific binding pair member, display intense visible absorption as well as fluorescence emission. Selected equipment that is useful for illuminating the fluorescent compounds of the invention includes, but is not limited to, hand-held ultraviolet lamps, mercury arc lamps, xenon lamps, argon lasers, laser diodes, and YAG lasers. These illumination sources can be optionally integrated into laser scanners, fluorescence microplate readers, standard or mini fluorometers, or chromatographic detectors. Any suitable computer software for measuring, processing and displaying images and/or data pertaining to the process of detecting and measuring signal sequences will be known to the skilled artisan and are contemplated by the invention.

Fluorescence emissions can be optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds of the invention and a second fluorophore with detectably different optical properties, typically by distinguishing the fluorescence response of the fluorescent compounds of the invention from that of the second fluorophore. Where a sample is examined using a flow cytometer, examination of the sample optionally includes isolation of particles within the sample based on the fluorescence response by using a sorting device.

The above description is not meant to limit the means, methods or instrumentation that can be used to detect, measure, quantitate, and analyze signals (e.g., fluorescence) produced by the photosensitizers of the invention in connection with those embodiments pertaining to the diagnostic methods of the invention. Any suitable means, methods or instrumentation for detecting, measuring, quantitating and analyzying photosensitizer signals are contemplated.

Targets and Samples

In certain embodiments, the photosensitizer compositions of the invention can be used in therapeutic methods to treat a bacterial infection in a subject in need thereof, e.g., where the infection is due to an antibiotic resistant pathogen.

The subject can be a living animal or human (e.g., host) carrying an unwanted organism (e.g., pathogen), that is, an organism that is a target for photodynamic therapy. The subject can be a mammal, such as a human or a non-human mammal (e.g., a dog, cat, pig, cow, sheep, goat, horse, rat, or mouse). The subject may be further immune deficient; presently or previously undergoing treatment for cancer (e.g., by chemotherapy or radiation therapy); or presently or previously undergoing antibiotic therapy or an immunosuppressive therapy.

In certain other aspects relating to use of the photosensitizer compositions of the invention for diagnostic purposes, e.g., detection of and/or quantitation of a beta-lactamase activity, a sample can be from any source, including samples obtained directly from infected tissues or bodily fluids (e.g., blood, urine, feces, skin, lymph, spinal fluid, muscle, heart, brain, stomach, intestine, and any other organ that my be carrying an infection to be treated with antibiotics), or bacterial cultures obtained from natural sources (e.g., patients, soils, sediments) or from commercial or stock sources which are desired to be assayed or tested for antibiotic resistance.

In aspects relating to therapeutic uses, an organism that is targeted for destruction by the methods and compositions described herein is an unwanted organism, unwanted in that it infects a host organism (or a cell thereof) and causes or aggravates a disease or disorder in that host.

Target organisms can be cellular. Such target organisms include at least a boundary cell membrane and are capable of energy production, nucleic acid synthesis, and contain ribosomes and are capable of ribosomal protein synthesis. Cells can be unicellular or multicellular, and said unicellular organisms can be prokaryotic or eukaryotic. The target cells may express or produce an antibiotic resistance phenotype (e.g., beta-lactamase phenotype) to be tested or evaluated using the herewith disclosed methods.

Prokaryotic target organisms for treatment and/or diagnosis in accordance with the method of the invention include bacteria, which bacteria can be Gram negative or Gram positive, or which are lacking cell walls. The Gram stain basis of distinguishing bacteria, based on whether or not cells of a specific strain or species of bacteria take up a stain, or are stained with the counterstain only, is known to those of skill in the art.

Gram negative, largely β lactamase-producing, bacterial genera suitable as target organisms for treatment and/or diagnosis include *Neisseria, Pasteurella, Proteus, Pseudomonas, Streptophomonas, Burkholderia, Acinetobacter, Serratia, Salmonella, Enterobacter, Escherichia, Haemophilus,* and *Klebsiella. Streptophomonas maltophilia, Burkholderia cepacia,* and *Acinetobacter baumannii* are, for example, common colonizers of patients in an intensive care setting. Gram positive bacterial genera suitable as target organisms include *Staphylococcus* and *Enterococcus.*

Other bacterial pathogens to be contemplated herein as "unwanted organisms" and, thus, to be targeted for destruction and or diagnostic analysis, include, without limitation, *Mycobacterium tuberculosis, Leishmania, Mycobacterium leprae,* and *Sheigella. Leishmania* do not produce β lactamase. Rather, they produce surface metalloproteinase gp63, which can, for example, cleave the heptapeptide AYLK-KWV. Thus, the latter polypeptide may serve as a suitable enzyme cleavage site within a linker in a photosensitizer composition according to the invention, for use in the therapeutic and/or diagnostic methods of the invention.

In some therapeutic aspects, pathogens that can be targeted by the compositions and methods of the present invention can be found on any light-accessible surfaces or in light-accessible areas, for example, in human and animal subjects. In the cases of humans and animals, infections of the epidermis, oral cavity, nasal cavity, sinuses, ears, lungs, urogenital tract, and gastrointestinal tract are light accessible. Epidermal infections include subcutaneous infections, especially localized lesions, which infections are light-accessible. Infections of the peritoneal cavity, such as those resulting from burst appendicitis, are light accessible via at least laparoscopic devices. A variety of skin infections which are refractory to antibiotics or long-term antifungal treatment, for example, dermatophycoses of the toenail, are suitable for photodynamic therapy using the methods and compositions of the invention. In certain diagnostic methods of the invention, samples comprising beta-lactamase enzymes or bacterial beta-lactamase producers can be obtained from any of the above diseased or infectious cells and/or tissues to identify and evaluate suitable antibiotic regimes that can be used in treatment.

Lung infection can occur with a variety of bacterial genera and species, which include the pseudomonads, which are the primary cause of death of cystic fibrosis patients, Klebsiella, and can also occur with a variety of virus strains. As pathogens of the lung are increasingly resistant to classical antibiotic therapies, photodynamic therapy and/or diagnosis with the compositions of the instant invention offer an alternative method for eliminating and/or diagnosing these unwanted organisms that is independent of the microbial mechanisms of resistance.

Additional epidermal infections and infections of deeper tissues arise from burns, scrapes, cuts, and puncture wounds. In one aspect, PDT treatment and/or diagnosis with the compositions of the instant invention are useful for sterilization of such potential infectious sites, which can rapidly lead to toxic shock, a frequent concomitant of bullet wounds, and for treating the sites to eliminate or reduce unwanted infectious organisms or determining a suitable and effective antibiotic regimen. A major cause of infection in wounds, especially burns, is the Gram negative aerobic bacterium *Pseudomonas*. This organism produces an exotoxin which has been shown to retard wound healing. Multi-antibiotic resistant *P. aeruginosa* strains are becoming a significant problem, especially in burns units of large hospitals. Pseudomonads also produce fulminating infections of the cornea. *Escherichia coli* along with *Staphylococcus aureus* are the two most common bacteria in infected wounds.

Other sites of unwanted target organisms include the urogenital tract, the peritoneal cavity, the inner and outer ear, the nasal cavity and the gastrointestinal tract. Infectious sites of proliferation of unwanted target organisms in tissues of mesothelial and endothelial origin are also accessible to PDT by minimally invasive techniques.

In other specific embodiments, areas of infection are not light-accessible. Such areas can be accessed, for example, with the use of light-emitting probes or catheters. Thus, delivery of the light to a recessed, or otherwise inaccessible physiological location can be facilitated by flexible fiber optics (implicit in this statement is the idea that one can irradiate either a broad field, such as the lung or a lobe of the lung, or a narrow field where bacterial cells may have localized). The source of the light needed to inactivate the compounds of the invention can be an inexpensive diode laser or a non-coherent light source.

The pathogens to be targeted by the diagnostic and/or therapeutic methods of the invention using the compositions of the invention may be naturally or non-naturally occurring. Non-naturally occurring pathogens comprise pathogens recombinantly engineered, for example, to exhibit resistance to certain standard antibodies. In a situation of bioterrorism, for example, one might envision a pathogen that does not naturally produce β lactamase being engineered to produce the latter. Recombinantly engineering a naturally occurring pathogen to exhibit multiple antibody resistance would yield a highly virulent strain difficult to combat by standard treatment measures (such as penicillin).

These and other bacterial groups and genera not listed here will be recognized by the skilled artisan as suitable target bacteria for the compositions of the invention. Thus, the above lists are used to illustrate applications of the present invention to major groups of suitable target organisms, but not to delimit the invention to the species, genera, families, orders or classes so listed.

The pathogen may be contained within a host cell, such as a phagocyte (e.g., a macrophage). Further, within that cell, the pathogen may be contained (wholly or partly) within a vacuole, vesicle, or organelle.

In aspects involving diagnostic uses of the photosensitizer compositions of the inventions, biological samples can be obtained from any of the above mentioned physiological locations for bacterial infection in order to measure, assay, or evaluate the production of various enzymatic virulence factors, e.g., beta-lactamase.

Antibacterial Compositions

In certain embodiments, the photosensitizer compositions of the present invention, or their pharmaceutically acceptable salts or esters, may be formulated into an antibacterial composition for treating target bacterial infections in accordance with the invention. The antibacterial compositions comprise one or more photosensitizer compositons as the active ingredient(s), in association with an organic or inorganic, solid or liquid carrier suitable for oral administration or non-oral administration or external applications, when said photosensitizer compositon is to be administered for the purpose of therapeutically treating bacterial infections, in particular, those bacterial infections that are resistant to antibiotics.

This antibacterial composition may be prepared in the form of any conventional formulations, which include capsules, tablets, ointments, suppositories, solutions, suspensions, emulsions and so on. If necessary, the above formulation may further contain a supplementary agent, stabilizer, wetting agent or emulsifier, or buffering agent, or any of other conventional additives.

Thus, the antibacterial composition of the invention may be administered in the form of a formulation, such as intravenous or intramuscular injections, orally administrable preparations, suppositories or the like. The excipient or carrier present in the composition may be chosen from the pharmaceutically acceptable ones, and the sort of the excipient or carrier varies depending on the route of administration and the method of administration. For instance, a liquid carrier may be used, which can include water, ethanol, or animal and vegetable oils, such as soybean oil, sesame oil, or mineral oil or synthetic oil, and so on. As a solid carrier, sugar, such as maltose and sucrose, an amino acid, such as lysine, a cellulose derivative, such as hydroxypropylcellulose and the like, a polysaccharide, such as cyclodextrins, and an organic acid salt, such as magnesium stearate, and the like.

When the antibacterial composition is formulated into an injection, in general, the carrier may desirably be physiological saline, various buffered solutions, aqueous solutions of a sugar such as glucose, inositol, mannitol and the like, or a glycol such as ethylene glycol, polyethylene glycol and the like. Further, the anti-bacterial composition may also be formulated into a lyophilised preparation in association with an excipient which may be a sugar such as inositol, mannitol, glucose, mannose, maltose, sucrose and the like, or an amino acid such as phenylalanine and the like. Upon administration, the lyophilised preparation may be dissolved into a solvent suitable for the injection, for example, a liquid available for intravenous injection, which may be sterile water, physiological saline, aqueous solution of glucose, solution of electrolytes and aqueous solution of amino acids, and the like.

The proportion of the photosensitizer composition formulated as an antibacterial composition may vary according to the type of the formulation but usually may be 0.1 to 99% by weight, preferably 1 to 90% by weight of the composition. For instance, an injectable solution may normally contain 0.1 to 10% by weight of the active ingredient compound. When the anti-bacterial composition is to be given orally, it is used in the form of a preparation such as tablets, capsules, powders, granules, dry syrups, liquids, syrups and the like, in association with a solid carrier or a liquid carrier as mentioned in the above. For the capsules, tablets, granules and powders, in general, the proportion of the active ingredient compound present therein may be 3 to 99% by weight, preferably 5 to 90% by weight of the composition, with the balance being the carrier.

The dosage of the photosensitizer composition of the invention to be used as the active ingredient, or its salt or ester depends on the age, body weight and symptoms of patients, and the purposes of the therapeutic treatment, and other factors. The dosage is to give an effective amount of the photosensitizer composition to combat against the infecting bacteria. The photosensitizer composition at a necessary dosage may be administered continuously or intermittently as long as a total dosage of the photosensitizer composition does not exceed a specific level which is decided in view of the results of animal tests and various circumstances.

When administered parenterally, the total dosage of the photosensitizer composition of this invention is, of course, administered with appropriate adjustments being done in view of the way of administration, the conditions of patients such as age, body weight and sex, as well as foods and medicines concurrently administered. Suitable dosage and administration frequency of the photosensitizer composition of this invention under given conditions can be determined by expert physician through the tests of determining optimal dosage in light of the above-mentioned guidelines. These guidelines for administration also apply to oral administration of the photosensitizer composition of the invention.

Diagnostic Methods and Kits

In yet another aspect, the present invention provides methods and diagnostic kits for using the photosensitizer compositions described herein for a wide array of diagnostic applications relating generally to the qualitative and/or quantitative detection of enzymes involved in antibiotic resistance, such as, beta-lactamase enzymes. In some aspects, the photosensitizer molecules of the invention are quenched prior to cleavage of the linker joining them together. Once the linker is cleaved, however, the photosensitizer molecules become physically separated, upon which time, they become activatable such that, when activated, they produce a detectable signal, e.g., a fluorescence signal. This feature can be utilized in accordance with the invention for qualitative and/or quantitative detection and/or measurement of the enzyme utilizing the linker as substrate, i.e., the "the activity of interest," e.g., a beta-lactamase. Such methods can also be used to obtain information regarding the substrate specificity of the activity of interest, e.g., a beta-lactamase activity, which can aid in the determination of an appropriate antibiotic therapy can be implemented.

The enzymes that are tested using the methods of the invention can be from any organism of interest, either isolated from an infection or directly from a cell or tissue, or those organisms that are isolated from the body and kept in culture or storage etc. The inventive assays can also be directed against the enzymes themselves, either in purified or non-purified form. The enzymes can be from any organism, for example, a Gram negative bacterium, such as, β lactamase-producing bacteria, including *Neisseria, Pasteurella, Proteus, Pseudomonas, Streptophomonas, Burkholderia, Acinetobacter, Serratia, Salmonella, Enterobacter, Escherichia, Haemophilus*, and *Klebsiella. Streptophomonas maltophilia, Burkholderia cepacia*, and *Acinetobacter baumannii* are, for example, common colonizers of patients in an intensive care setting. Gram positive bacterial genera suitable as target organisms include *Staphylococcus* and *Enterococcus*.

In one aspect, the present invention provides a method for detecting the presence of an enzyme activity of interest, e.g., a beta-lactamase activity, in a sample. The method includes contacting the sample with at least one photosensitizer composition described herein, and photoactivating the sample to induce a signal to be released from unquenched photosensitizers, and detecting the signal, e.g., a fluorescence signal.

The "signal" as used herein refers to a detectable response produced by photoactivation of the unquenched photosensitizers of the invention which is directly or indirectly detectable (observable) either by visual observation or by instrumentation or other suitable means for detection. Typically, the detectable response is a detectable response in an optical property, such as a change in the wavelength distribution patterns or intensity of absorbance or fluorescence or a change in light scatter, fluorescence lifetime, fluorescence polarization, or a combination of such parameters in a sample. The signal may occur throughout the sample or in a localized portion of the sample. The presence or absence of the signal after the elapsed time is indicative of one or more characteristics of the sample. Comparison of the amount of the compound of the invention with a standard or expected response can be used to determine whether and to what degree a sample possesses the enzyme (and enzymatic activity) of interest.

In one aspect, the present invention provides methods for detecting an enzyme activity of interest, e.g., beta-lactamase activity, from a sample by use of the photosensitizer compositions of the invention. Such detection methods can be per se detection methods, which, as used herein, refers to a qualitative, 'yes/no,' detection of a an enzyme activity of interest, e.g., beta-lactamase activity. In advantageous aspects, the methods of the invention provide for per se detection methods to detect beta-lactamase activity in a sample, wherein the detection of activity against a photosensitizer composition of the invention indicates a resistance to the particular antibiotic-based linker because said linker is cleaved by the activity. In other aspects, information regarding the susceptibility of a linker of the invention to a bacterial enzyme, e.g., a beta-lactamase enzyme from a biological sample, can be used to determine an effective antibiotic regimen to be applied against an infection. In some aspects, the antibiotic regimen can comprise the administration of an antibiotic which has a different structure than that of the cleaved linker. In still other aspects, information regarding linker susceptibility can be used to determine the type or class of beta-lactamase enzyme produced by the bacteria causing an infection. Beta-lactamase types or classes are discussed herein above. It will be understood that knowledge of the type or class of the beta-lactamase enzyme of a pathogenic organism can provide information regarding the particular antibiotics that might be effective against the pathogen of interest.

In other aspects, the detection methods of the invention provide a means for detecting an enzyme activity of interest, e.g., beta-lactamase activity, as a function of another process that involves production of that particular enzyme having the activity. In a particular aspect, the invention provides a method of detecting a beta-lactamase activity as a function of the production of said enzyme due to another process (such as where a beta-lactamase encoding nucleic acid is used as a reporter gene to measure expression of the nucleic acid). Such detection methods may be practiced on both cell-free and cellular systems (e.g., intracellular detection). Examples of methods for detecting beta-lactamase activity in which the presently disclosed photosensitizer compositions of the invention may be utilized as susbstrates for a beta-lactamase include those methods disclosed in U.S. Pat. Nos. 5,955,604, 5,741,657, 6,031,094, 6,291,162, and 6,472,205, each of which are incorporated herein by reference.

As described in the above-referenced United States patents (such as, U.S. Pat. No. 6,472,205), cells to be assayed for beta-lactamase activity may be contacted with a photosensitizer composition described herein. In the presence of a beta-lactamase, the linker substrate is cleaved, rendering the photosensitizers to transition into an unquenched state, i.e., activatable state. Upon illumination with the appropriate wavelength and/or quantity of light, a detectable signal is produced, such as the generation of fluorescence emissions. If a beta-lactamase is present in the sample, and the linker is susceptible to being cleaved by the said enzyme, then the sample will exhibit increased fluorescence when contacted with a photosenstitizer composition of the invention. Such fluorescence changes can be detected by exciting the sample with radiation of a first wavelength, which excites the photosensitizer group, which emits radiation of a second wavelength, which can be detected. The amount of the emission is measured, and compared to proper control or background values. The amount of emitted radiation that differs from the background and control levels, either increased or decreased, correlates with the amount or activity of the beta-lactamase in the sample. Standard curves can be determined for quantitative measurements.

In a further aspect, the present invention provides a method for determining whether an enzyme of interest in a sample, e.g., beta-lactamase enzyme, can cleave a disclosed linker of a photosensitizer composition of the invention. The method involves contacting the sample with a photosensitizer composition of the present invention, thereby leading to the cleavage of any susceptible linkers, followed by exciting the sample with radiation of one or more wavelengths that are suitable for the cleaved compound, and determining the degree of fluorescence emitted from the sample. A degree of fluorescence emitted from the sample that is greater than an expected degree (or baseline level) indicates that the beta-lactamase enzyme can cleave the compound and that the compound is a substrate for the beta-lactamase enzyme.

In another aspect, a method for determining whether a sample contains beta-lactamase activity is provided. The method involves contacting the sample comprising a beta-lactamase activity with a photosensitizer composition of the invention under conditions sufficient to allow the cleavage of any susceptible linker moiety by the beta-lactamase activity. Cleavage of a linker causes the photosensitizers to separate and become unquenched and consequently, photo-activatable. The sample is then irradiated with one or more wavelengths that are absorbed by the unquenched photosensitizers, which then emit fluorescence of a particular wavelength and strength. A degree of fluorescence emitted from the sample that is greater than expected, i.e., greater than a baseline control sample containing no beta-lactamase activity, indicates the presence of beta-lactamase activity in the sample. One aspect of this method is for determining the amount of an enzyme in a sample by determining the degree of fluorescence emitted at a first and second time after contacting the sample with a compound of the present invention. The difference in the degree of fluorescence emitted from the sample at the first and second time is determined, and the difference reflects the amount of a beta-lactamase enzyme in the sample.

In another aspect, the present invention provides screening assays that utilize the disclosed photosensitizer compositions and a host cell, such as a mammalian cell, transfected with at least one recombinant nucleic acid molecule encoding at least one protein having beta-lactamase activity. Such recombinant nucleic acid molecules can include expression control sequences adapted for function in a eukaryotic cell, such as a vertebrate cell, operatively linked to a nucleotide sequence coding for the expression of a beta-lactamase enzyme.

In yet another aspect, methods are provided for determining the amount of beta-lactamase activity in a cell. This method involves contacting a sample, including a host cell that is transfected with a recombinant nucleic acid molecule that includes a nucleic acid sequence coding for the expression of a beta-lactamase. The sample can comprise whole host cells, or an extract of the host cells, which is contacted with a photosenstitizer composition of the present invention. The amount of photosensitizer composition cleaved is measured by measuring a detectable response, whereby the amount of substrate cleaved is related to the amount of beta-lactamase activity in the host cell.

In another aspect, a method for monitoring the expression of a gene operably linked to a set of expression control sequences is provided. The method involves providing a host cell transfected with a recombinant nucleic acid molecule, where the nucleic acid molecule comprises a set of expression control sequences operatively linked to nucleic acid sequences coding for the expression of a beta-lactamase enzyme, except if the host cell is a fungus, the beta-lactamase is a cytosolic beta-lactamase enzyme. A sample comprising the host cell, or an extract or conditioned medium produced therefrom or thereby, is contacted with a disclosed compound. The amount of compound cleaved is determined, wherein the amount of substrate cleaved is related to the amount of beta-lactamase activity in the host eukaryotic cell, which is related to the expression of the gene.

In another aspect, a method is provided for determining whether a test compound alters the expression of nucleic acid sequence operably linked to an expression control sequence(s). The method involves contacting a host cell transfected with a recombinant nucleic acid sequence, where the recombinant nucleic acid comprises an expression control sequence(s) operably linked to a nucleic acid sequence coding for a beta-lactamase. The host cell is contacted with the test compound, and the host cell is then contacted with a disclosed photosenstitizer composition. The amount of the photosenstitizer composition cleaved is then measured, whereby the amount of the photosenstitizer composition cleaved is related to the amount of beta-lactamase activity in the cell. In addition, the amount of photosenstitizer composition cleaved in the presence of the test compound can be compared to the amount of photosensitizer composition cleaved in the absence of the test compound to determine if the test compound alters expression regulated by the control sequence.

In another aspect, a method for clonal selection is provided, wherein cells that are presumably transfected with a recombinant nucleic acid molecule comprising a sequence coding for a beta-lactamase are contacted with a disclosed compound. Those cells that are in fact transfected with the recombinant nucleic acid molecule will exhibit beta-lactamase activity, which is detected by measuring the detectable optical change produced upon cleavage of the photosensitizer composition. Cells that exhibit beta-lactamase activity, or greater than a predetermined level of beta-lactamase activity may be selected, and propagated if desired. Selection of cells exhibiting beta-lactamase acitvity can be accomplished using fluorescence activated cell sorting (FACS), using, for example, a Becton Dickinson FACS Vantage.

Another aspect is to use a beta-lactamase reporter gene and a compound of the present invention to screen test chemicals for biochemical activity. A cell transfected with a recombinant nucleic acid molecule that includes at least one expression control sequence operably linked to at least one nucleic acid sequence encoding for the expression of a beta-lactamase enzyme is contacted with a test chemical. The cell is then contacted with a disclosed photosenstitizer composition and the amount of the photosenstitizer composition cleaved is measured. The amount of photosensitizer composition cleaved reflects the amount of beta-lactamase activity within the at least one cell, and reflects the biochemical activity of the test chemical. The amount of photosenstitizer composition cleaved in the presence of the test chemical is compared to the amount of photosensitizer composition cleaved in the absence of the test chemical to determine if the test chemical increases, decreases or does not alter expression under control of the control sequence.

The interaction of a particular disclosed photosensitizer composition with a particular beta-lactamase enzyme can be readily determined. In one embodiment, such a method involves contacting the sample with a photosensitizer composition to cause the cleavage of the linker, exciting at one or more wavelengths that are suitable for the unquenched photosensitizers, and determining the degree of fluorescence in the sample. A degree of fluorescence that is greater than an expected amount in the absence of beta-lactamase activity indicates that the particular beta-lactamase enzyme can cleave the particular compound. The amount of fluorescence expected can be determined using, for example, a control sample, or control values determined contemporaneously, prior to, or after a particular assay was performed. Such expected values can include a statistical analysis, such as a mean and standard deviation, to provide a chosen statistical confidence level. Both naturally occurring beta-lactamase enzymes and beta-lactamase enzymes prepared by mutagenesis can be tested with a particular disclosed compound.

Any of the above methods specifically disclosed, and other method that include the use of the disclosed photosenstitizer compositions to detect beta-lactamase activity may further include use of the methods described in U.S. Pat. No. 6,284,461 to increase the signal to noise ratio of the disclosed assays.

In addition, the disclosed compounds may be used to detect beta-lactamase activity in a wide variety of biologically important environments, such as human blood serum, the cytoplasm of cells and intracellular compartments, which can facilitate the measurement of periplasmic or secreted beta-lactamase enzyme. In addition, the presence (for example, in human serum, pus, urine, or other fluid, sample, or tissue) of bacteria resistant to beta-lactam antibiotics may be readily detected by using the disclosed compounds. Only in the presence of an active beta-lactamase enzyme is there a fluorescence spectrum that is characteristic of the photosensitizers. Such methods include contacting the environment with a disclosed photosensitizer composition and detecting any beta-lactamase activity present by measuring the detectable optical change that occurs upon cleavage of the photosensitizer composition by a beta-lactamase. Further, the expression of any target protein may be detected by fusing a gene encoding the target protein to a beta-lactamase gene, which can be localized by immunostaining or fluorescence or electron microscopy. For example, beta-lactamase fusion proteins can be detected in the lumen of organelles through the use of the substrates of the invention. In this instance, only subcellular compartments containing the fusion protein fluoresce at a wavelength characteristic of the cleaved substrate, whereas all others fluoresce at a wavelength characteristic of the intact molecule.

In yet another aspect, the present invention provides a method of evaluating the substrate specificities of various beta-lactamases, i.e., typing a beta-lactamase in one of the known classes of beta-lactamase enzymes (e.g., type A, B, C, or D). In one aspect, the substrate specificity of a beta-lactamase can be determined by contacting a series of photosensitizer compositions comprising a plurality of different linkers. The linkers of the series of photosensitizer compositions of the invention can be any of the herein disclosed linkers, e.g., cephalosporin, penicillin, penem, a carbapenem or a moncyclic mobactem, along with numerous others, including any fragments and/or derivatives thereof. Linkers that are susceptible to cleavage represent those compounds against which the beta-lactamase shows substrate specificity. Linkers that are not susceptible to cleavage represent those compounds against which the beta-lactamase enzymes are not effective and which do not have substrate specificity. Those linkers showing substrate specificity represent those antibiotics which would be not be effective in treating an infection caused by an organism expressing such beta-lactamases. In this way, an appropriate antibiotic regime can be designed and which would reflect the particular substrate specificity of the encoded beta-lactamase of the infective organism. Thus, ineffective antibiotics can be avoided.

Samples may be obtained and/or prepared from any suitable source using any suitable means for preparation. Samples include, without limitation, any biological material that is thought to contain an enzyme activity of interest, e.g., a beta-lactamase. The enzyme activity of interest is advantageously an enzyme which confers antibiotic-resistance in a bacterium (e.g., beta-lactamase). Alternatively, samples also include material in which a beta-lactamase has been added. The samples can be a biological fluid, such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, beta cells, hepatocytes, and neurons.

In many instances, it may be advantageous to add a small amount of a non-ionic detergent to the sample. Generally the detergent will be present in from about 0.01 to 0.1 vol. %. Illustrative non-ionic detergents include the polyoxyalkylene diols, e.g. Pluronics, Tweens, Triton X-100, etc.

Kits

In another aspect, the present invention provides a kit that includes one or more of the disclosed photosensitizer compositions. The kit can also include an additional component, for example, instructions for using the photosensitizer compositions in one or more methods, additional molecules (such as a beta-lactamase, or a nucleic acid coding for a beta-lactamase such as a vector having a beta-lactamase sequence as a reporter), substances (such as a reaction buffer), or biological components (such as cells, or cell extracts). For example, cells (e.g., prokaryotic or eukaryotic cells) which contain beta-lactamase activity and/or at least one beta-lactamase substrate, as well as compositions and reaction mixtures which contain such cells can be included in the kits. Cells may further include receptor and signaling molecules that regulate expression of nucleic acid sequences within the cell, either sequences found on vectors, or in the nucleus or mitochondria of the cells. Cells, compositions and reaction mixtures that include at least one of the disclosed compounds are also part of the disclosure, regardless of whether or not they are part of a "kit" per se.

In some aspects, the kit includes a solid support covalently bonded to a disclosed photosenstitizer composition and instructions for detecting a beta-lactamase in a sample with the solid support. In other aspects, the kit includes a disclosed photosensitizer composition that includes a reactive group, a solid support and instructions which specify how to immobilize the compound on the solid support and how, after forming the immobilized photosenstitizer composition, to detect a beta-lactamase. Alternatively, the kit includes a solid support bearing reactive groups that can react with and immobilize a beta-lactamase, and instructions that specify how to immobilize beta-lactamases to the solid support and to detect such immobilized beta-lactamases using one or more of the photosenstitizer compositions of the disclosure. Methods of detecting immobilized beta-lactamases are presented above.

In another aspect, the kit may include compositions for the quantitative determination of a beta-lactamase in a sample. In an aspect, the composition comprises a sample containing a known amount of a beta-lactamase (such as a solution containing the known amount of beta-lactamase or cells expressing known amounts of the beta-lactmase) and a disclosed photosenstitizer composition of the invention, wherein the photosenstitizer composition reacts with a beta-lactamase to produce a detectable optical response that is proportional to the amount of the beta-lactamase in the sample, for example, an amount of a fluorescent product or fluorescence emission that is proportional to the amount of the beta-lactmase in the sample.

Beta-lactamases that may be included in a kit according to the disclosure can be of any type, and include both naturally-occurring beta-lactmases and non-naturally-occurring beta-lactamases, such as those disclosed in Bush et al. (1995) Antimicrob. Agents Chemother. 39:1211-1233, which is incorporated herein by reference.

Those skilled in the art will appreciate that the polypeptides having beta-lactamase activity disclosed herein may be altered by, for example, mutating, deleting, and/or adding one or more amino acids and may still be used in the practice of the invention so long as the polypeptide retains detectable beta-lactamase activity toward at least one disclosed compound. An example of a suitably altered polypeptide having beta-lactamase activity is one from which a signal peptide sequence has been deleted and/or altered such that the polypeptide is retained in the cytosol of prokaryotic and/or eukaryotic cells.

In yet another aspect, the present invention provides a method and kit for typing or characterizing a beta-lactamase enzyme in terms of its substrate specificity. In this embodiment, the kit comprises one or more photosensitizer compositions disclosed herein. The kit further comprises one or more competing beta-lactam antibiotics or derivatives thereof, such as any of those beta-lactam antibiotics described herein. In practice, the kit can be used generally to compare the level of signal generated by reaction of the one or more photosensitizer compositions with the beta-lactamase enzyme of the kit in the presence and absence of the one or more competing beta-lactam antibiotics (or fragments or derivatives thereof). By comparing the signals generated with and without the one or more competing beta-lactam antibiotics, the skill artisan can determine the substrate specificity of the enzyme. It would be expected that a reduced signal (relative to a baseline of a photosensitizer composition without a competing beta-lactam) of the photosensitizer composition of the invention when in the presence of a competing beta-lactam antibiotic suggests that the competing beta-lactam antibiotic is a cleavable substrate of the beta-lactamase, and as such would not be effective against a bacterium that expresses the tested beta-lactamase. On the other hand, it would be expected that an unaffected or unchanged signal (relative to a baseline of a photosensitizer composition without a competeing beta-lactam) of the photosensitizer composition of the invention when in the presence of a competing beta-lactam antibiotic suggests that the competing beta-lactam antibiotic is not a cleavable substrate of the beta-lactamase, and as such would be effective against a bacterium that expresses the tested beta-lactamase.

Thus, in one aspect, the present invention provides a method and/or kit that allows for the typing and/or classification of a beta-lactamase in terms of substrate specificity with instructions for: performing a non-competitive reaction comprising the steps of (a) contacting the sample with a photosensitizer composition comprising a plurality of photosensitizers that are conjugated to a linker, wherein the linker comprise a cleavage site for a beta-lactamase and wherein the photosensitizers are in a quenched state; (b) cleaving the linker to dequench the photosensitizers; (c) light-activating the composition to produce a fluorescence signal; and (d) quantifying the fluorescence signal with a detector.

EXAMPLES

Example 1. Preparation of a Photosensitizer Composition Comprising a Polymer, β-Lactam Moiety and Photosensitizer In one approach, the synthesis of the conjugates is based on cephalosporin, a commonly used β-lactam. It is conceivable to develop penem or carbapenem derivatives subsequently.

In the following, the photosensitizer (a porphyrin molecule with at least one propionic side chain) is represented by PS-$CH_2$—$CH_2$—COOH. The polymer used in the synthetic routes shown below is a linear or branched poly(ethylene glycol) with propionic acid groups (PEG-CH$_2$—CH$_2$—COOH) (Senter, P. D., et al. (1995) Bioconjug. Chem. 6:389-394). However, the chemistry is applicable to similar polymeric materials containing available carboxylic side chains. In order to be released upon enzymatic hydrolysis, the porphyrin molecule is advantageously linked at the 3'-position of the cephalosporin. The cephalosporin-porphyrin moiety obtained can then be conjugated to the polymer using the amino group on the β-lactam ring.

The preparation of three different conjugates is proposed, where the porphyrin and cephalosporin are linked via an ester:

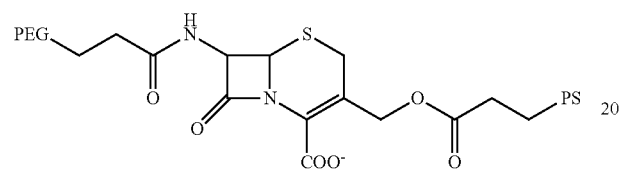

or via a carbamate group:

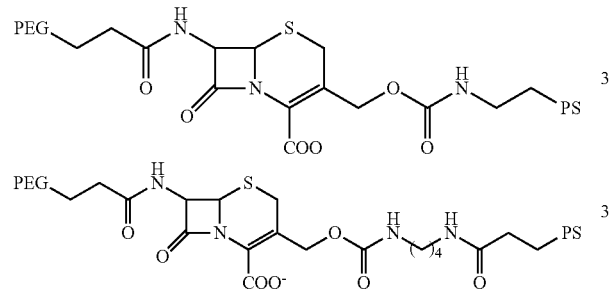

The preparation of a cephalosporin-prophyrin ester comprises the following steps:

A. Protection of the amino-group in the β-lactam ring

There are several ways to protect the amino group. One is represented below (Hanessian, S., et al. (1993) Can. J. Chem. 71:896-906):

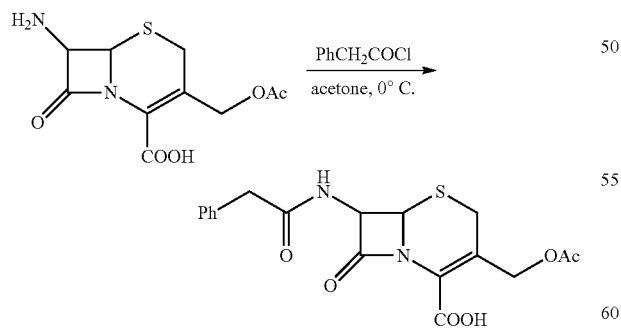

Protected cephalosporin derivatives are commercially available. Other protecting groups include (Albrecht, H. A., et al., (1990) J. Med. Chem. 33:77-86; Albrecht, H. A., et al. (1991) J. Med. Chem. 34:2857-2864; Alexander, R. P., et al. (1991) Tetrahedron Lett. 32:3269-3272):

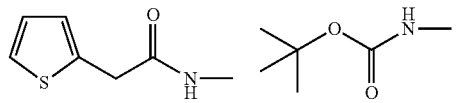

For example, the following molecule (which comes with a protected amino group) is called cephalothin.

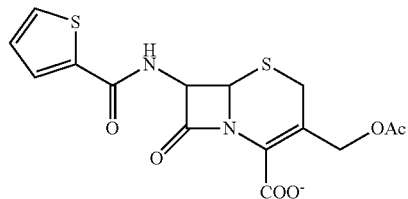

B. Binding of the porphyrin at the 3'-position of the cephalosporin via an ester function i. Through a diazomethyl intermediate (Mobashery, S., et al. (1986) J. Biol. Chem. 261:7879-7887)

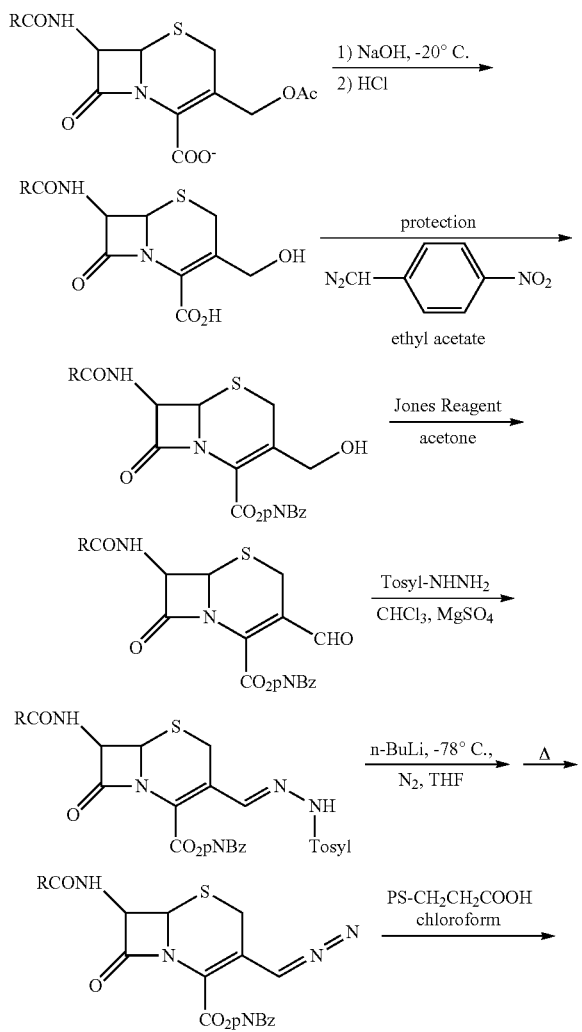

53

-continued

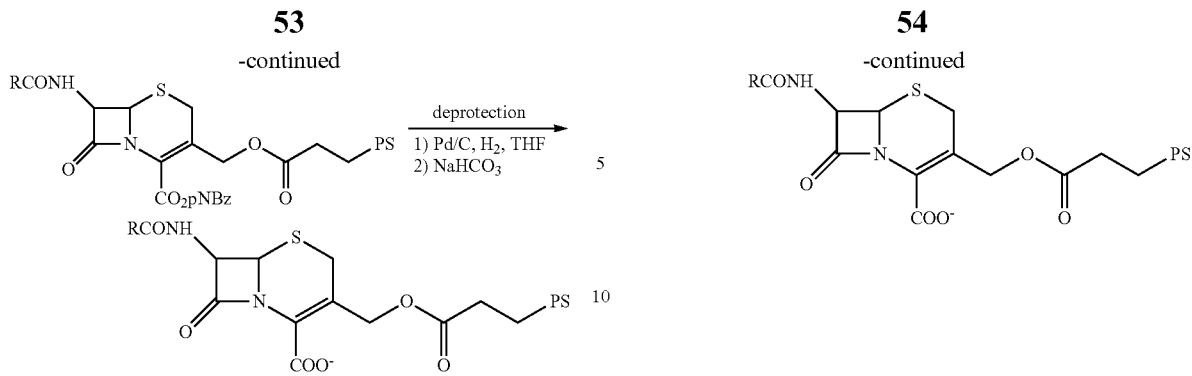

In this scheme, pNBz=para-nitro-benzyl.

ii. Through a halogenated intermediate (Mobashery, S., et al. (1986) J. Biol. Chem. 261:7879-7887)

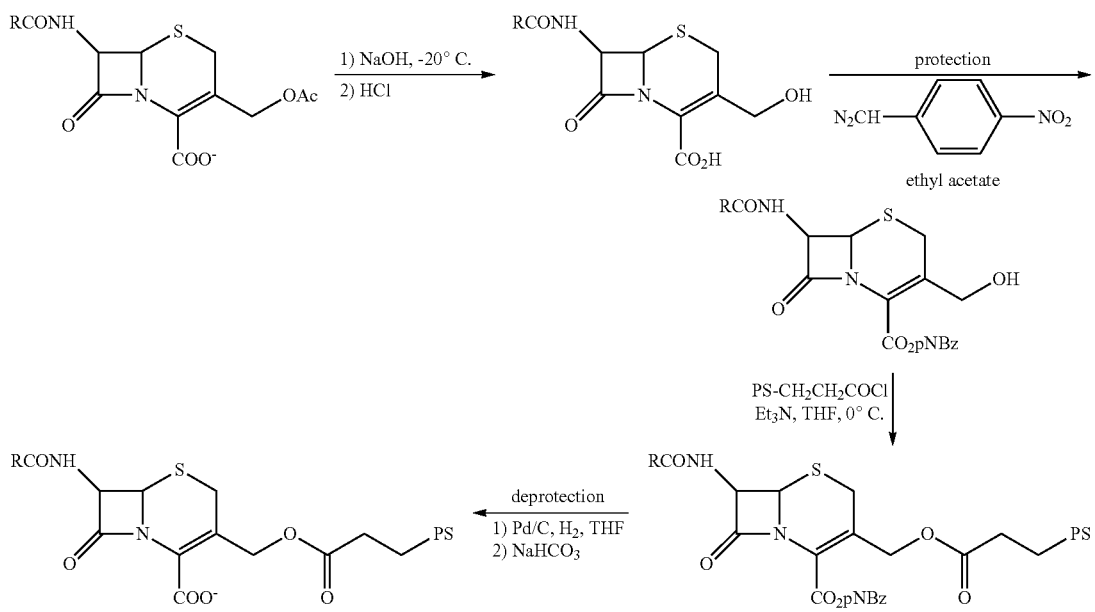

54

-continued iii. Through a hydroxymethyl intermediate (Hanessian, S., et al. (1993) Can. J. Chem. 71:896-906)

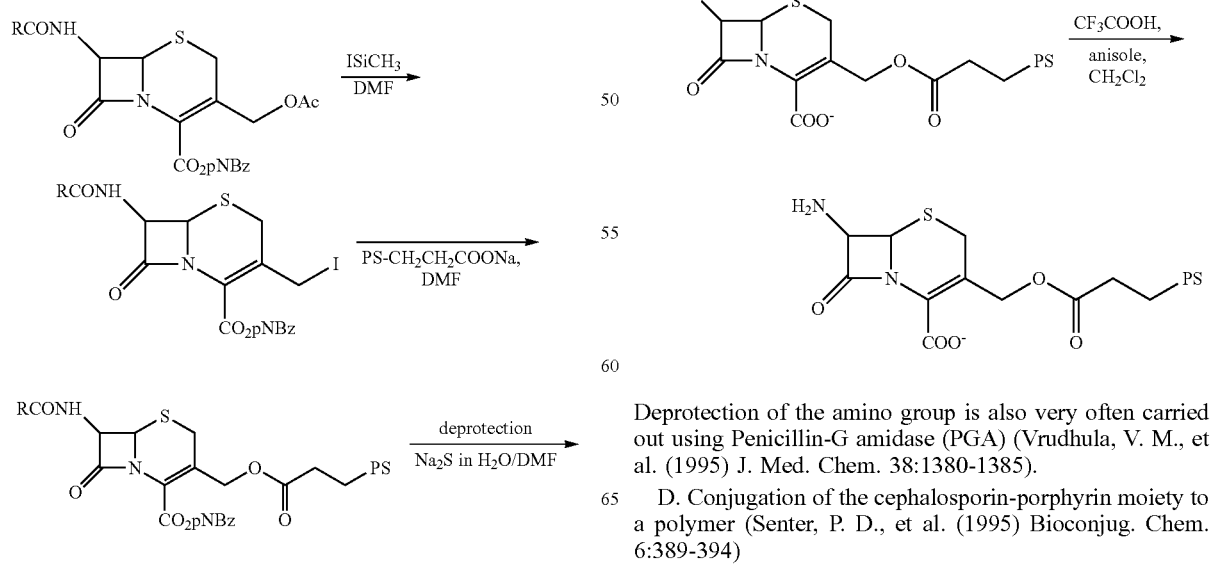

C. Deprotection of the amino-group in the B-lactam ring (Albrecht, H. A., et al. (1991) J. Med. Chem. 34:669-675)

Deprotection of the amino group is also very often carried out using Penicillin-G amidase (PGA) (Vrudhula, V. M., et al. (1995) J. Med. Chem. 38:1380-1385).

D. Conjugation of the cephalosporin-porphyrin moiety to a polymer (Senter, P. D., et al. (1995) Bioconjug. Chem. 6:389-394)

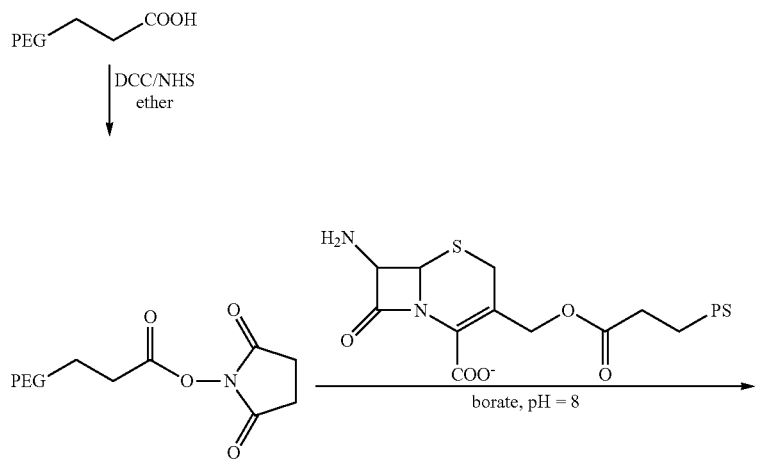

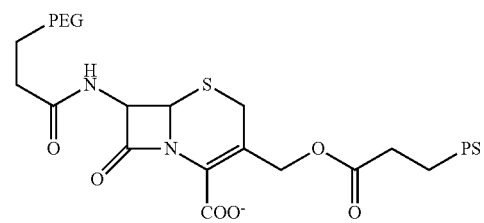

The preparation of a cephalosporin-porphyrin carbamate comprises the following steps:

A. Protection of the amino-group in the β-lactam ring (see above)

B. Binding of the porphyrin at the 3'-position of the cephalosporin via a carbamate i. Direct coupling between the porphyrin and cephalosporin (Alexander, R. P., et al. (1991) Tetrahedron Lett. 32:3269-3272; Rodrigues, M. L., et al. (1995) Chem. & Biol. 2:223-227; Smith, K. M., et al. (1987) Heterocycles 26:1947-1963)

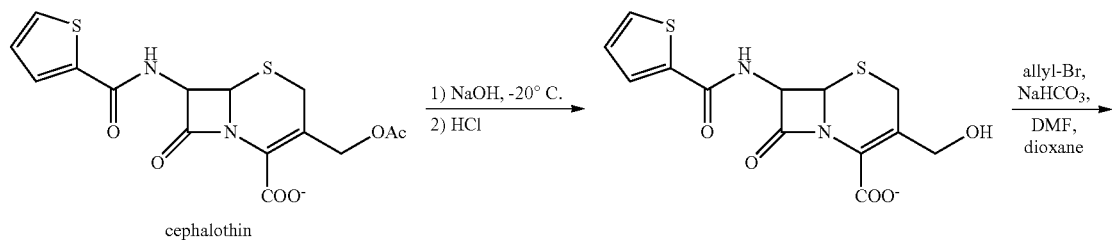

cephalothin

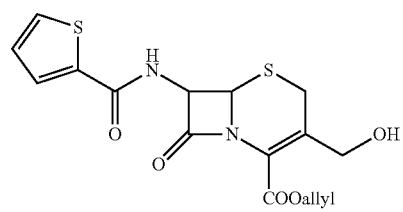

nitrophenyl chloroformate, pyridine/THF

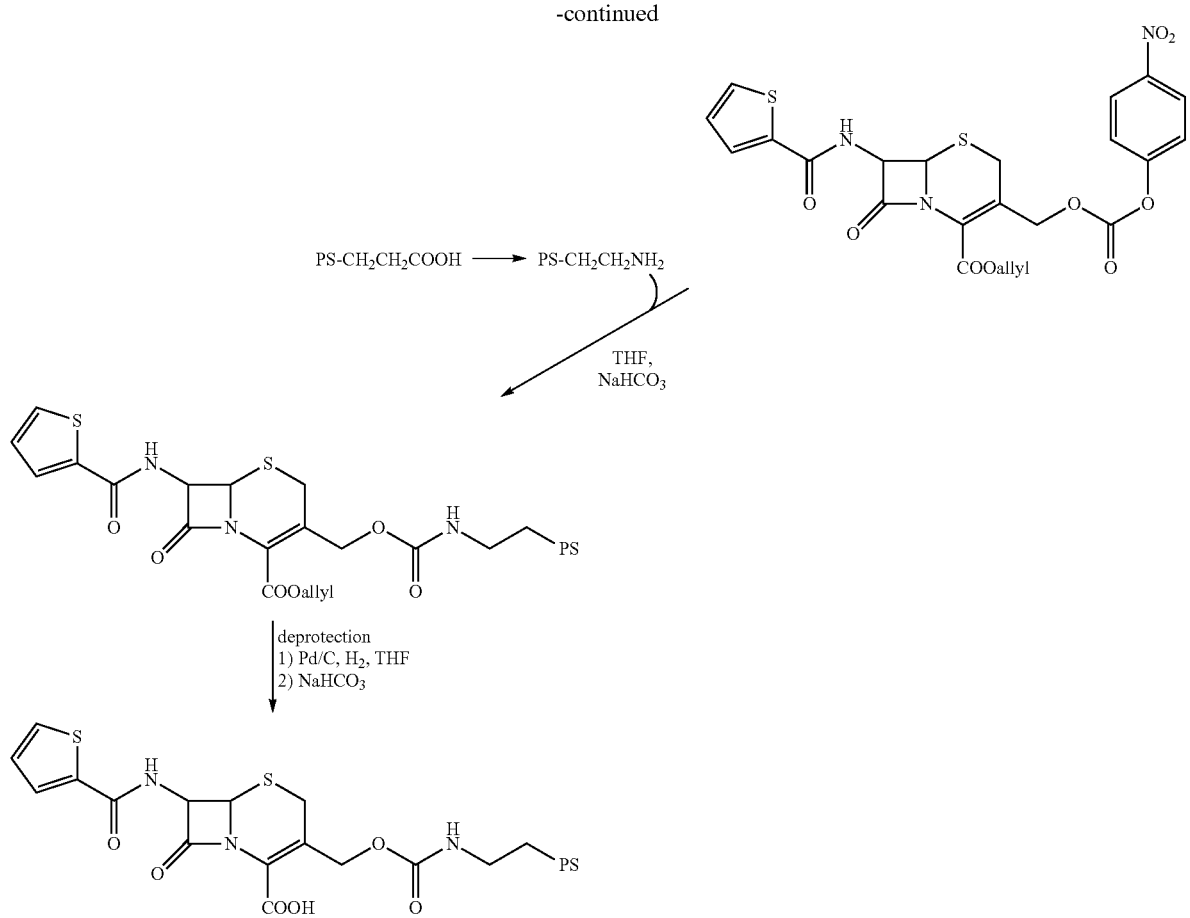
ii. Coupling through a linker (Alexander, R. P., et al. (1991) Tetrahedron Lett. 32:3269-3272; Rodrigues, M. L., et al. (1995) Chem. & Biol. 2:223-227; Boutorine, A. S., et al. (1996) J. Am. Chem. Soc. 118:9469-9476)
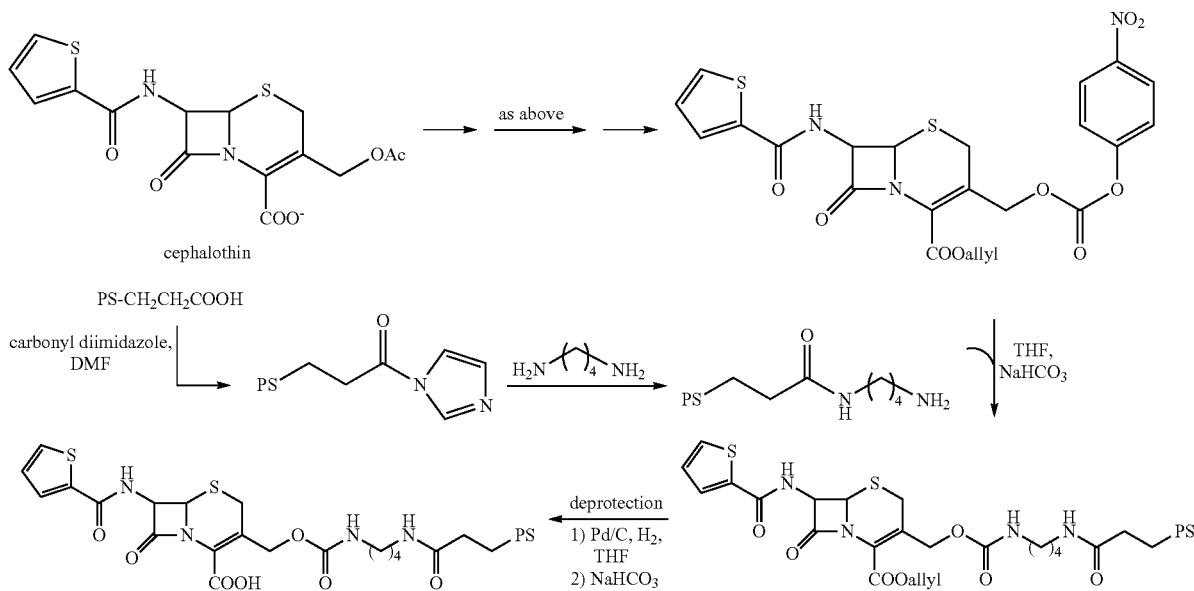

C. Deprotection of the amino-group in the β-lacatam ring (see above)

D. Conjugation of the cephalosporin-porphyrin moiety to a polymer (Senter, P. D., et al. (1995) Bioconjug. Chem. 6:389-394) (see above)

Of additional note, if, after these chemical modifications, the cephalosporin derivatives described above retain their properties as substrates for β-lactamases, one can expect to observe the enzyme-dependent release of three different porphyrin moieties:

$PS-CH_2-CH_3$:

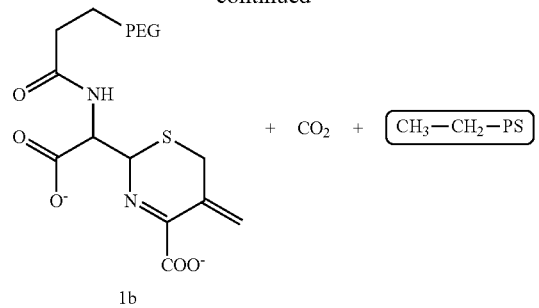

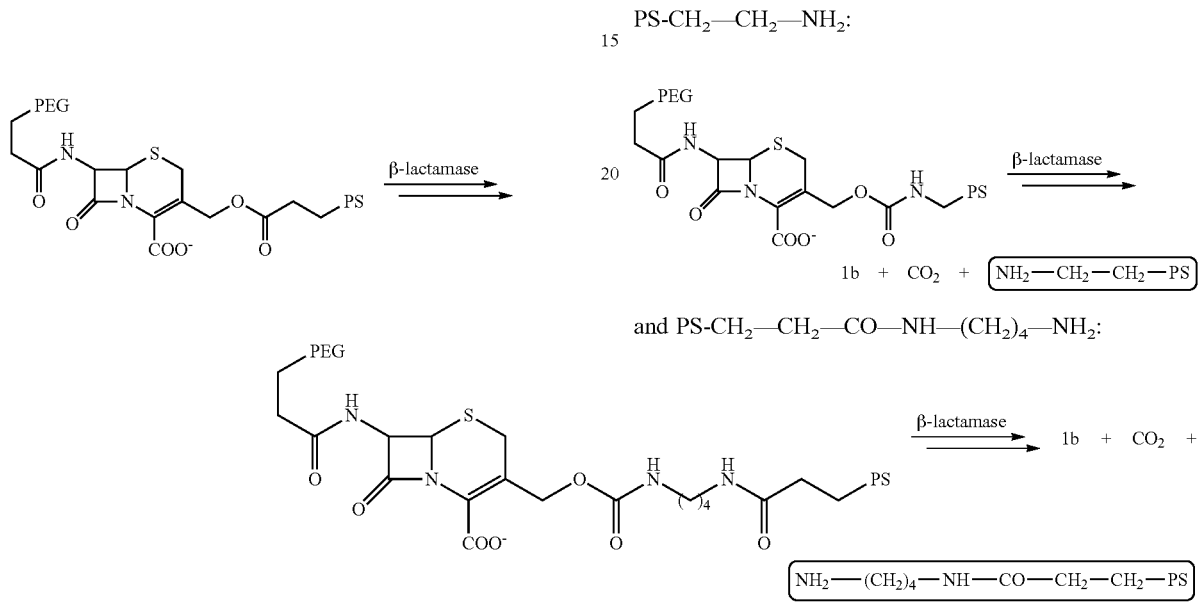

$PS-CH_2-CH_2-NH_2$:

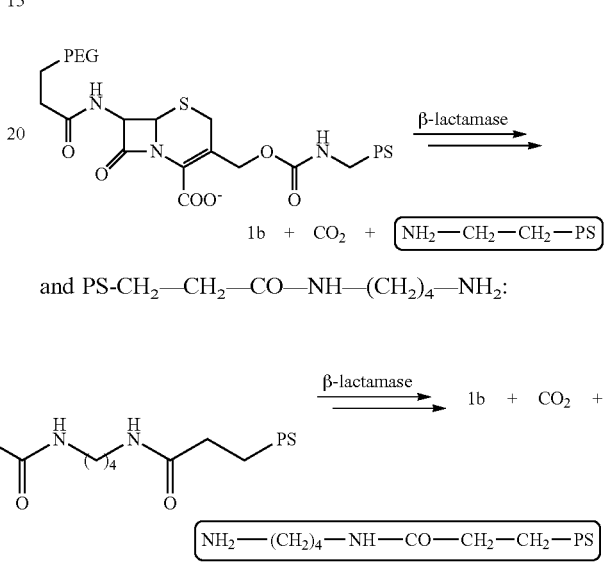

and $PS-CH_2-CH_2-CO-NH-(CH_2)_4-NH_2$:

Example 2. Development of Carbamate-Linked Photosensitizer, Inactive (with or without Light) while Linked and Light-Activatable Only when Released by the β-Lactamase Enzyme-Mediated Cleavage Unlike conventional antibiotics, where hydrolysis of the beta-lactam ring by β-lactamases causes inactivation, the beta-lactam ring opening of the prodrugs releases the photosensitizer and make it light-activatable for photokilling (FIG. 1).

Synthesis

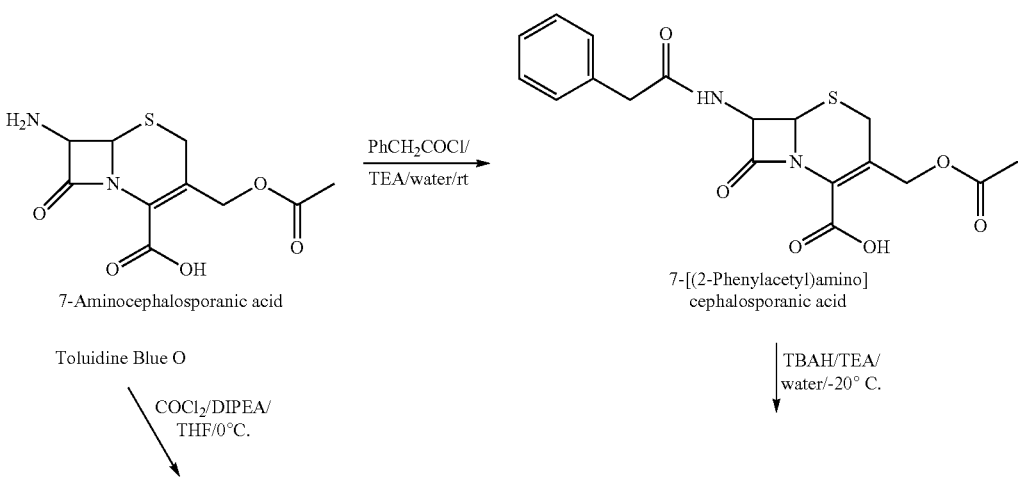

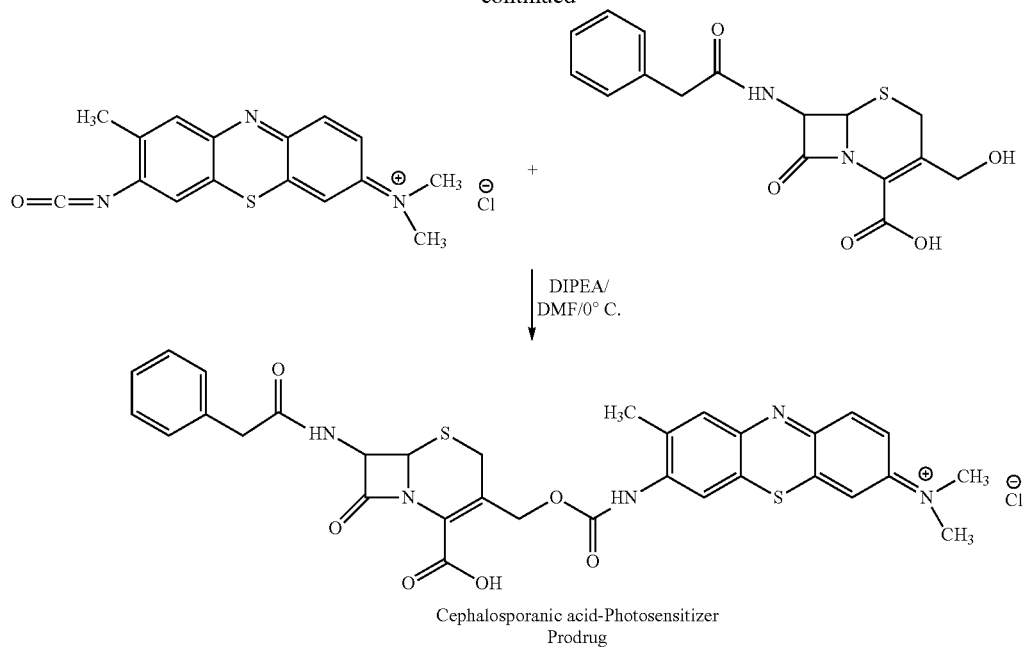

Cephalosporanic acid-Photosensitizer
Prodrug

Commercially available 7-aminochephalosporanic acid was reacted with phenylacetyl chloride under Shotten-Baumann reaction conditions to achieve an amino protected chephalosporin molecule. This was further de-esterified using tetrabutylammonium hydroxide as a base to yield easily functionalizable hydroxy end group on cephalosporin. The last step of the synthesis was achieved in a one-pot reaction sequence. Toluidine Blue O (TBO) was converted into its isocynate derivative in the presence of diphosgene. The carbamate-linked prodrug (herein sometimes referred to as prodrug 1) was obtained by adding Cephalosporin derivative to the same reaction mixture.

Synthesis of 7-[(2-phenylacetyl)amino]
cephalosporanic acid

To a stirred mixture of sodium bicarbonate (2.1 g, 25 mmol) in water (40 ml) and acetone (30 ml), added 7-(phenylacetyl)amino cephalosporanic acid. Stirred this solution for nearly 15 min in ice bath and slowly added phenylacetyl chloride (2.5 ml, 20 mmol) over the period of 30 min. This reaction mixture was stirred overnight and acidified to pH 2.0 with 1N hydrochloric acid. Precipitates obtained were extracted with dichloromethane and washed with water. Dried over magnesium sulphate and solvent evaporated to give off-white solid. The solid sample was stirred overnight in diethyl ether and filters to obtain crude product in 80% yield.

Synthesis of
7-[(2-phenylacetyl)amino]3-hydrodxymethy
cephalosporanic acid

To a suspension of 7-[(2-phenylacetyl)amino] cephalosporanic acid (0.5 g, 1.28 mmol) in a mixture of methane (4 ml) and water (2.5 ml), triethylamine (0.21 ml, 1.54 mmol) was added in 15 min at 0-5° C. To this solution, tetrabutylammonium hydroxide (30% solution in water, 1.53 g, 1.92 mmol) was added at −18° C. in 30 minutes. The reaction mixture was maintained at −18° C. for nearly 7.0 h and acidified to pH 5.0 using glacial acetic acid. Purification was done using C-18 reverse phase column and pure product was obtained as white solid in 67% yield.

Synthesis of Cephalosporanic Acid-Toluidine
BlueO Prodrug

To a magnetically stirred suspension of toludine blue O (0.1 g, 0.33 mmol) in anhydrous THF (3 ml) under nitrogen was added a solution of tricholoromethyl chloroformate (19.7 µl, 0.164 mmol) over activated charcoal as a catalyst. The reaction mixture was stirred at 55° C. for 30 min. Progress of reaction was monitored using mass spectroscopy for formation of isocynate derivative of toludine blue O. Cooled the flask to room temperature and added a solution of 7-[(2-phenylacetyl)amino] 3-hydrodxymethy cephalosporanic acid (0.15 g, 0.33 mmol) in anhydrous dichloromethane (1 ml). The reaction flask was cooled to 0° C. and slowly added diisopropylethylamine (57.0 µl, 0.33 mmol). Stirred for 3.0 h and purified using C18 column with acetonirile and water as eluting solvents. Pure product obtained as a blue solid in 25% yield.

Figures 2A, 2B:
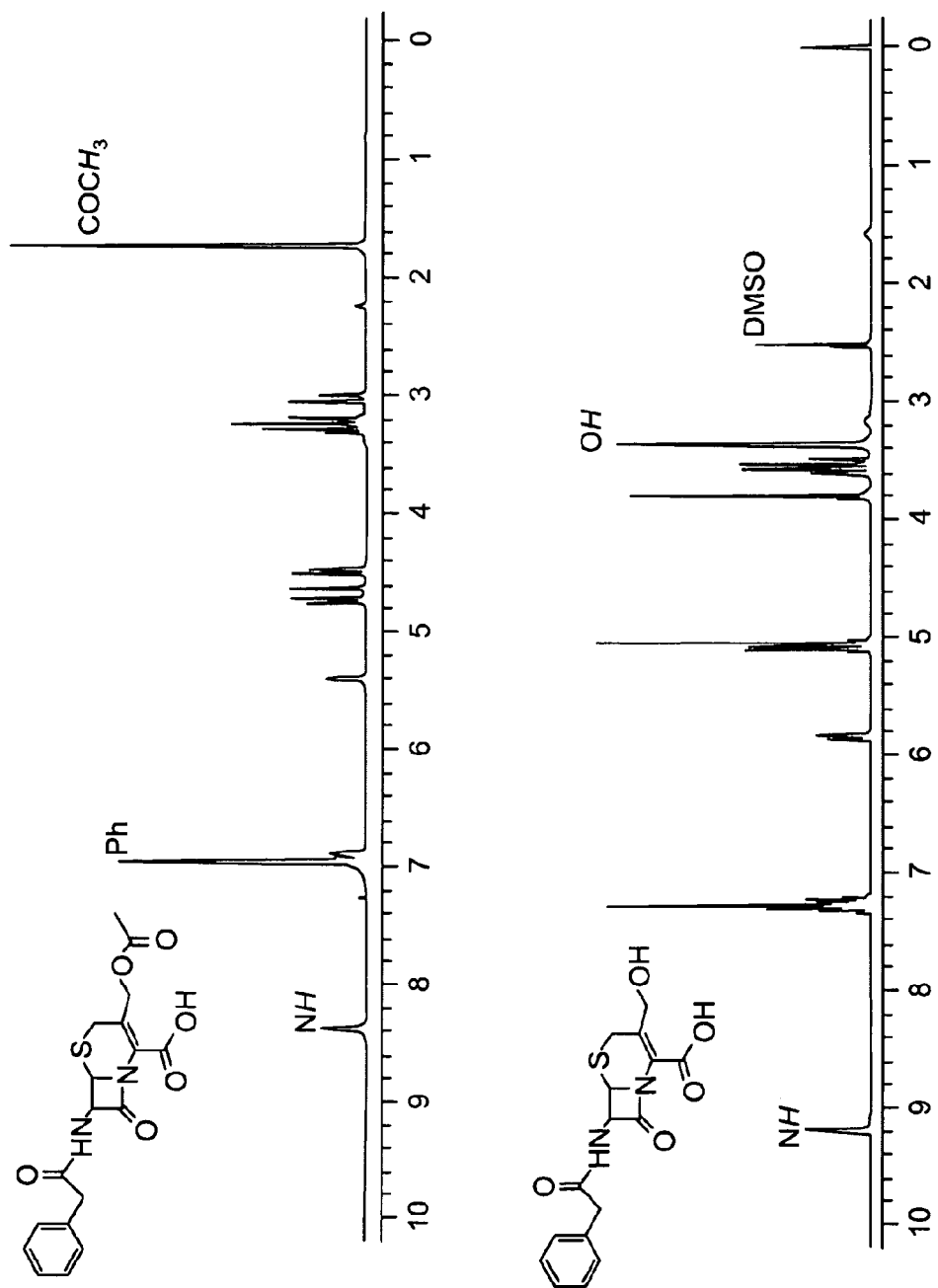
FIG. 2a shows $^1$H NMR spectra obtained for 7-[(2-phenylacetyl)amino] cephalosporanic acid in $CDCl_3$ as a solvent.
FIG. 2b shows $^1$H NMR spectrum obtained for 7-[(2-phenylacetyl)amino] 3-hydrodxymethy cephalosporanic acid in DMSO-$d_6$ as a solvent. Major proton peaks are marked on the spectra.

$^1$H NMR spectra were obtained for 7-[(2-phenylacetyl)amino] cephalosporanic acid in CDCl$_3$ as a solvent, as well as for 7-[(2-phenylacetyl)amino] 3-hydrodxymethy cephalosporanic acid in DMSO-d$_6$ as a solvent (FIG. 2). MS spectra were obtained for 7-[(2-phenylacetyl)amino] 3-hydrodxymethy cephalosporanic acid and cephalosporanic acid-toluidine blue O prodrug (FIG. 3).

Figure 4:
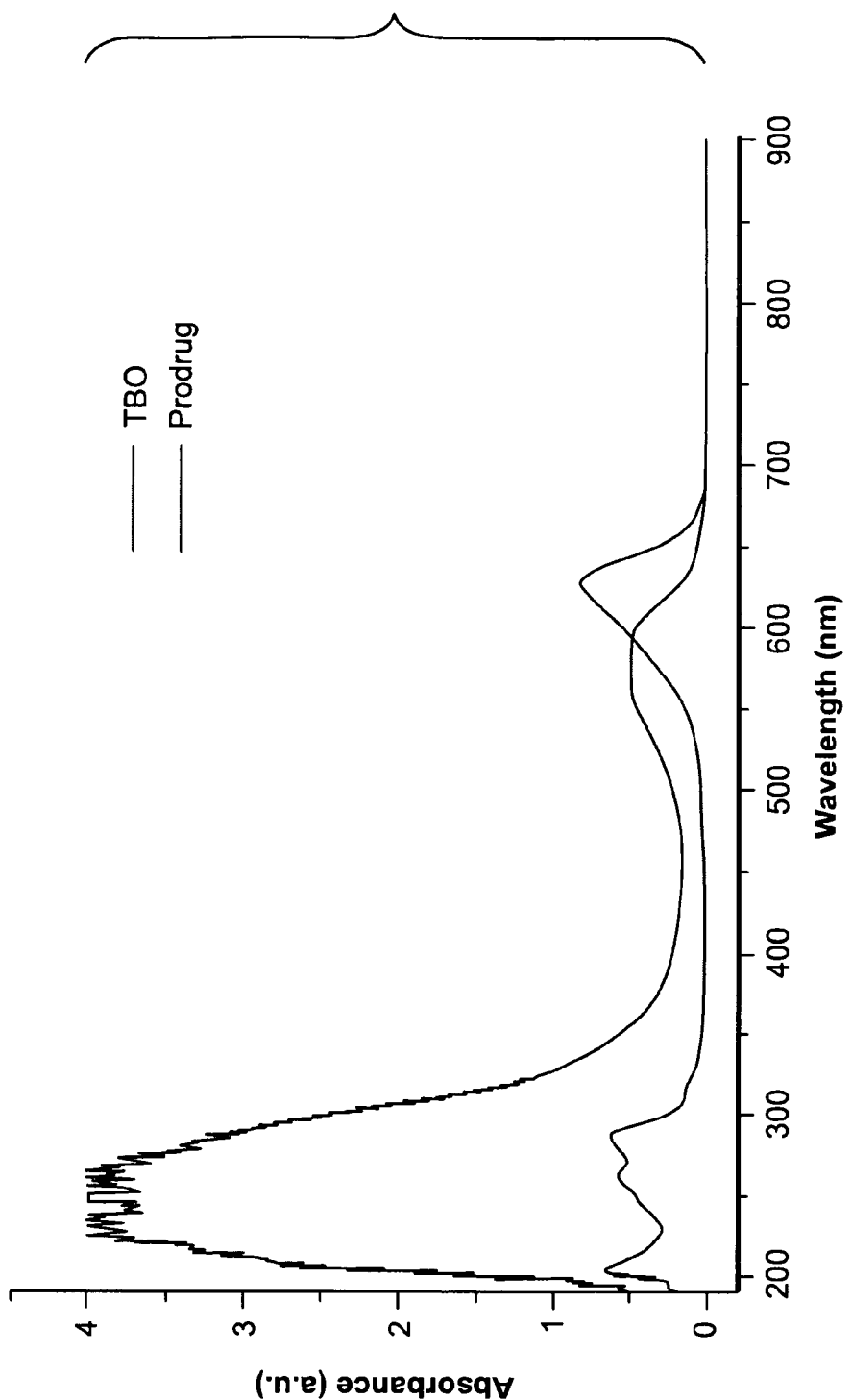
FIG. 4 shows UV-visible spectra obtained for the photosensitizer (TBO) vs. the cephalosporanic acid-photo sensitizer prodrug in ethanol at a concentration of $2.0 \times 10^{-5}$ M.
Figure 5:
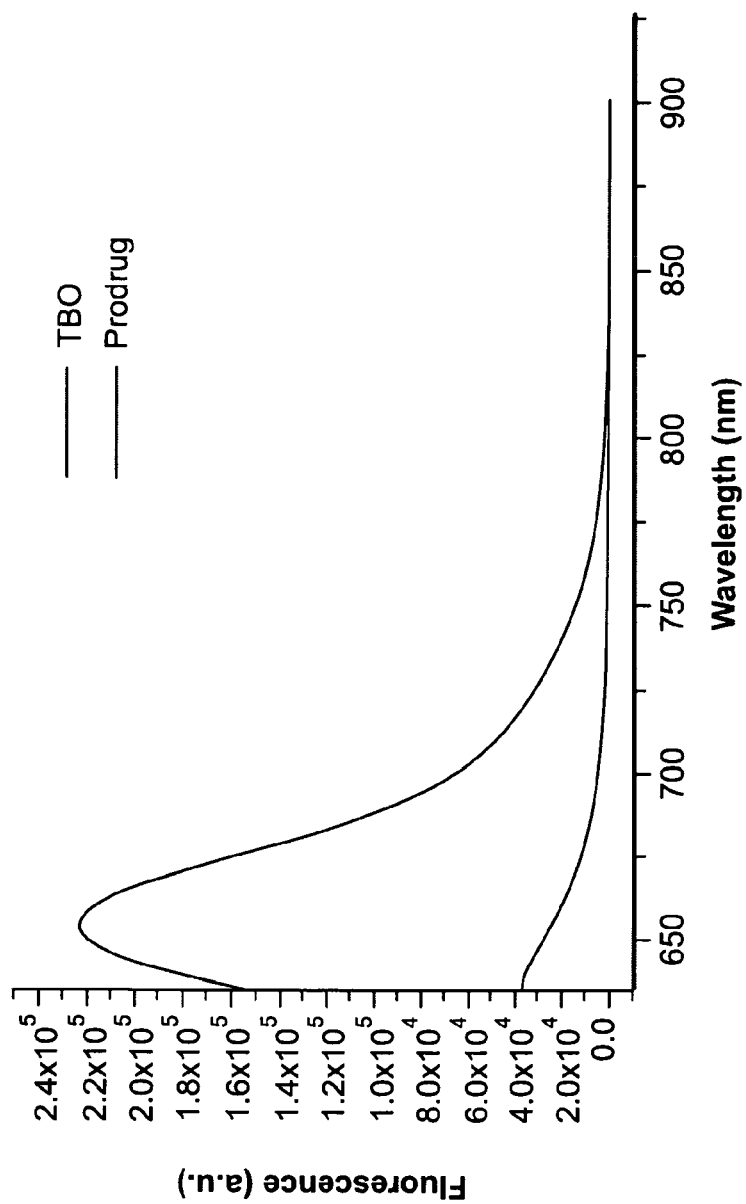
FIG. 5 shows fluorescence emission spectra obtained for the photosensitizer (TBO) vs. the cephalosporanic acid-photosensitizer prodrug in ethanol at 635 nm excitation.

UV-visible spectra revealed blue shift in the absorption spectra of the prodrug, indicating extended conjugation, as well as quenching, of carbamate linked TBO photosensitizer (FIG. 4). Fluorescence spectra revealed nearly an 8-fold reduction in fluorescence emission maxima at 635 nm excitation, indicating quantitative quenching of the photosensitizer upon conjugation with the cephalosporin moiety (FIG. 5).

Enzyme-Mediated Cleavage of the Prodrug

Figures 6A, 6B:
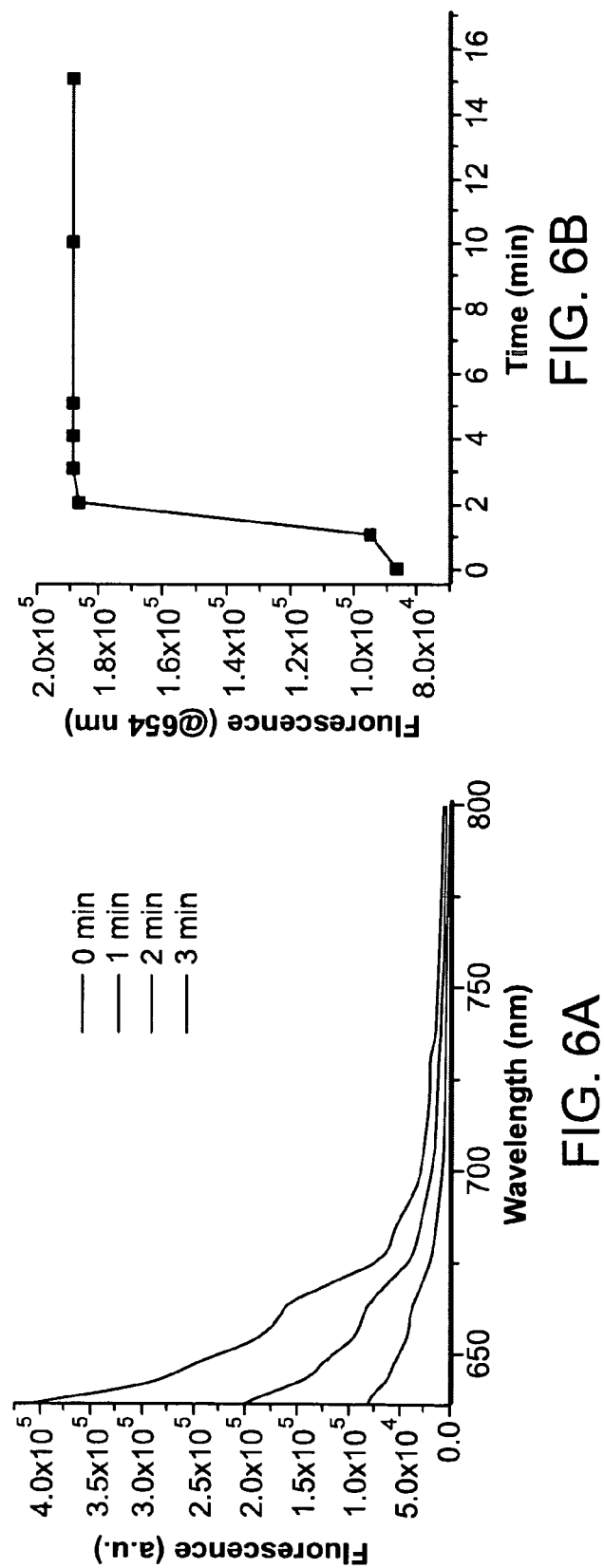
FIG. 6 shows plots of (a) fluorescence emission vs. wavelength and (b) fluororescence emission vs. time for the cephalosporanic acid-photosensitizer prodrug, depicting the enzyme-mediated cleavage of the prodrug.

The prodrug obtained was further studied for release of photosensitizer in presence of β-lactamase from *Enterobacter cloacae*. For the fluorescence emission study of the prodrug, the solvent employed was water, and the excitation wavelength 635 nm in the presence of beta-lactamase enzyme (from *Enterobacter cloacae*). Time-dependent fluorescence emission was also measured for photosensitizer release from the prodrug in the presence of enzyme. The results indicate an easy release and nearly 5-fold increase in excited stated properties within minutes of incubation of prodrug with enzyme (FIG. 6).

Thus, the prodrug was synthesized and characterized. Furthermore, the prodrug showed quantitative quenching of the photosensitizer in the conjugated form. Additionally, the product demonstrated lactamase-specific activity.

Example 3. Construction and Use of a Beta-Lactamase Enzyme Activated Photosensitizer Prodrug (β-LEAPP)

Background

Photodynamic therapy (PDT) is an emerging approach for the treatment of antibiotic resistant bacterial infections (Hamblin et al., 2004, Photochem. Photobiol. Sci., 3:436-50; Wainwright, J. Antimicrob. Chemother., 1998, 42:13-28). There are four fundamental constituents of PDT: light, a photosensitizer, oxygen and a target. Photosensitizers (PS) are dyes that absorb light energy and transfer that energy to a recipient molecule thus producing reactive molecular intermediates that destroy the biological target (Hamblin et al., 2004, Photochem. Photobiol. Sci., 3:436-50). The effective doses required for the inactivation of bacteria via PDT can damage the surrounding host tissue (Gad et al., Photochm. Photobiol. Sci., 2004, 3:451-8). The development of more specific photosensitizers for the PDT of bacterial infections would reduce damage to host tissue and enhance the antibacterial effect. This example also demonstrates that such compounds are useful for the detection, quantitation and typing of a target virulence enzyme (e.g. beta-lactamase) and may advantageously be used to determine an appropriate course of antibiotic therapy.

The present invention involves, in one aspect, the use of a substrate for a hydrolytic bacterial virulence enzyme (e.g., beta-lactamase) as a linker (e.g., beta-lactam ring) for two photosensitizers or fluorophores. The proximity of the linked fluorophores to each other results in a quenched (non-photoactive) state (see FIG. 7).

Figure 7:
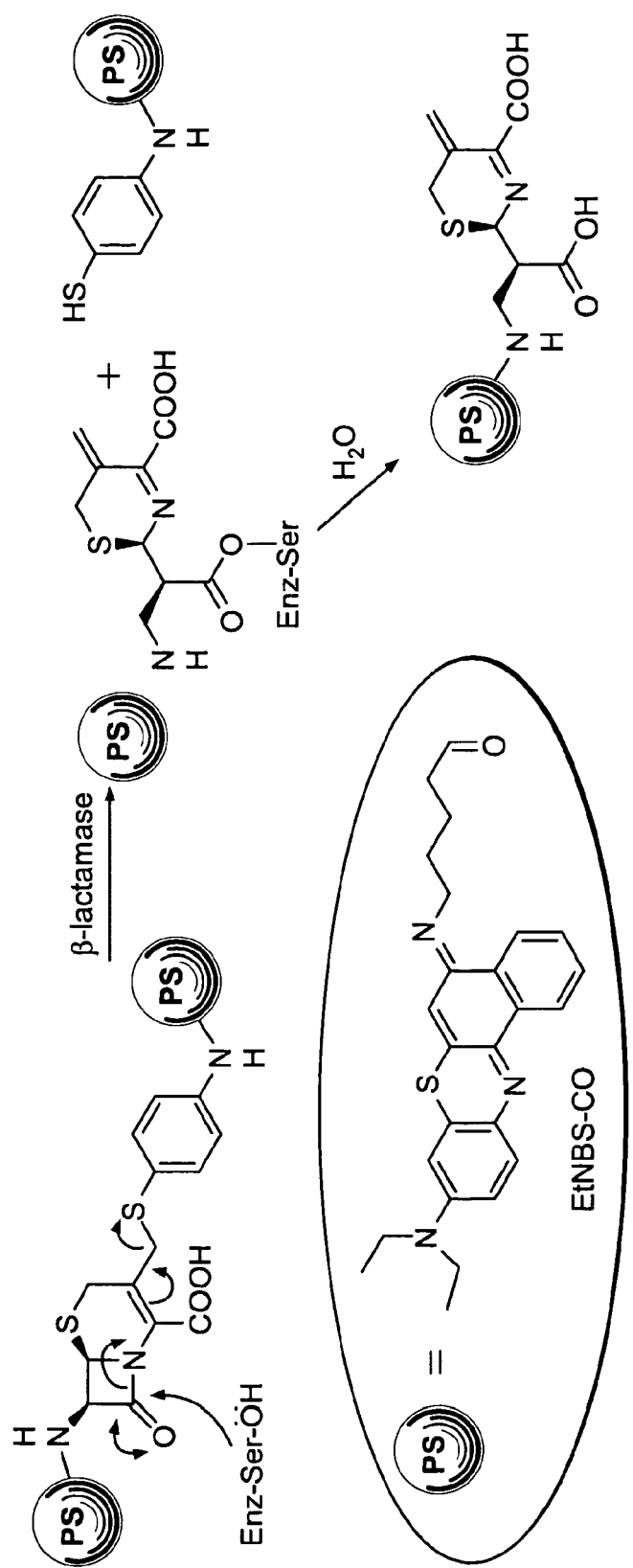
FIG. 7 depicts the specific mechanism for bacterial beta-lactamase enzyme mediated photosensitizer prodrug (β-LEAPP) activation in demonstrating the principle of the use of hydrolytic bacterial virulence enzymes for the specific release of active photosensitizer from a quenched state.

Upon hydrolysis of the substrate, the fluorophores are released from quenching and become photoactive, capable of the absorption of light energy and the transfer of that energy to another molecule or the release of that energy in the form of light fluorescence (see FIG. 7).

The photoactive phenothiazines are a group of tricyclic PSs that absorb in the red region of the electromagnetic spectrum (Cincotta et al., Photochem. Photobiol., 1987, 46:751-8). EtNBS is a benzo[a]phenthiazinium photosensitizer (PS) that is highly phototoxic to a broad spectrum of bacteria (Cincotta et al., Photochem. Photobiol., 1987, 46:751-8). Recently, the present inventors have synthesized and characterized derivatives of the phenothiazine EtNBS that are functionalized for conjugation to substrates of hydrolytic enzymes produced specifically by pathogens and not by the host (e.g., humans) (see FIG. 7). When the substrate is intact, the proximity of the PS molecules to each other results in static quenching that is defined by reduced light absorbance and energy transfer capacities. Following the enzymatic cleavage of the substrate molecule, the PS molecules are separated and therein released from quenching. When free, the PS exhibits increased absorbance and energy transfer capacity. The result is a PS prodrug that is activated in and around the infectious drug resistant bacteria by a bacterial virulence enzyme and/or which is capable of releasing a fluorescence signal when light-activated.

Figure 8:
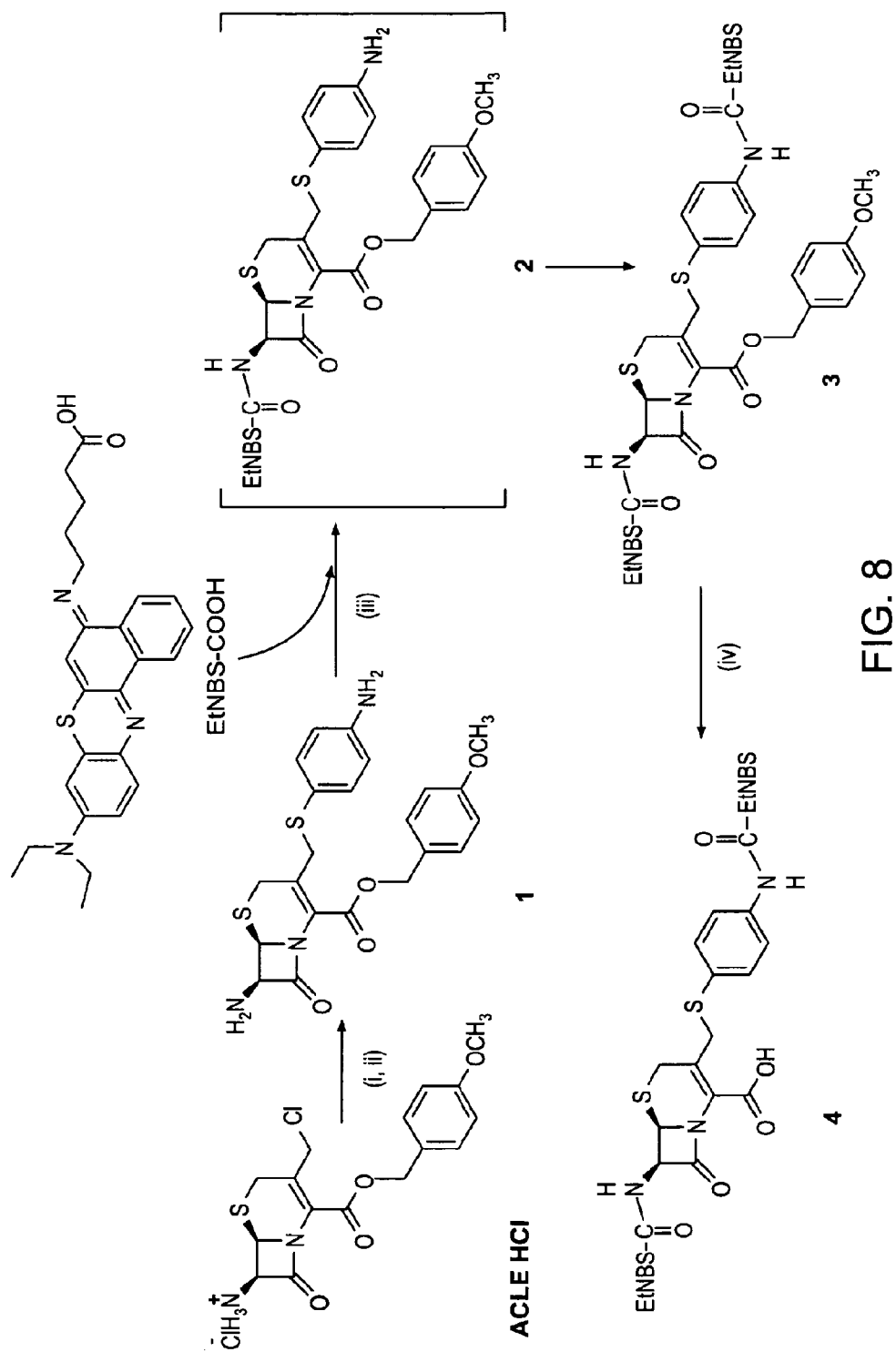
FIG. 8 depicts the synthesis of β-LEAPP.

This example describes the use of a photosensitizer composition ("β-LEAPP") comprising two EtNBS molecules conjugated to cephalosporin, a substrate molecule for beta-lactamase (see FIG. 8). The synthesis scheme depicted in FIG. 8 can be summarized as follows: 7-amino-3-(4-aminophenylthio)methyl-3-cephem-4-carboxylic acid p-methoxybenzyl ester (1). ACLE hydrochloride (100 mg, 0.247 mmol) was suspended in dichloromethane (DCM, 3 ml) at 0° C. Triethylamine (40 ul, 0.287 mmol) was added in three portions over a 20 min period. 4-methylmorpholine (NMM, 35 ul, 0.032 mmol) was added, followed with 4-aminothiophenol (32 ul, 0.3 mmol). Reaction mixture was stirred at 0° C. for 2 h then purified using silica gel chromatography (1.5% methanol in DCM as eluent) to afford 46 mg (40%) of 1 as white solid. EtNBS-ACLE Conjugates with p-methoxybenzyl protection group (3 and 4). EtNBS-COOH (130 mg, 0.3 mmol) and HATU (114 mg, 0.3 mmol) were stirred in DMF (500 ul) for 30 min and 1 (46 mg, 0.1 mmol) was added to this reaction mixture. The reaction mixture was stirred at 4° C. for 72 h to allow for complete conversion of mono-substituted intermediate (2) to di-substituted product (3). The solvent was removed in vacuo and the residue was redissolved in dichloromethane. The organic layer was washed with brine and dried over sodium sulfate. After removing the solvent, the crude product was purified on silica preparative PLC (10% methanol in DCM as eluent) to afford 27 mg of di-EtNBS conjugate 3 (21%) and 26 mg of mono-EtNBS conjugate 2 (30%). Compound 3 (6 mg, 0.0046 mmol) was further dissolved in a mixture of trifluoroacetic acid, anisole and DCM (1.5 ml, 1:1:5) and stirred at 0° C. for 2 h. The solvent was removed in vacuo and the residue was purified by RP-HPLC to yield 4 (5 mg, 90% yield).

Beta-lactamase is a hydrolytic enzyme expressed by many antibiotic resistant bacteria and not by humans. Initial studies by the inventors have demonstrated that the beta-lactamase enzyme activated photosensitizer prodrug (β-LEAPP) exhibits increased in vitro antibacterial PDT effect against MRSA when compared to a betalactamase non-producing *S. aureus* (unpublished data). These findings promise advantage for the use of the prodrug in the PDT of antibiotic resistant bacterial infections, e.g., for use in the treatment of Methicillin-Resistant *Staphylococcus aureus* (MRSA) and other drug resistant bacterial infections.

An advantageous feature of β-LEAPP is that the hydrolytic cleavage that results in its activation also results in the increase of its fluorescence emission. In experimentation towards evaluating the ability of various beta-lactamase producing strains of bacteria to activate, (cleave), β-LEAPP, it was discovered that the resultant increase in fluorescence emission was rapidly detectable and provided quantitative data. This finding indicated that β-LEAPP is ideal for the detection and quantitation of beta-lactamase activity, among other uses.

Detection and Quantitation of Beta-Lactamase Activity

Figure 9:
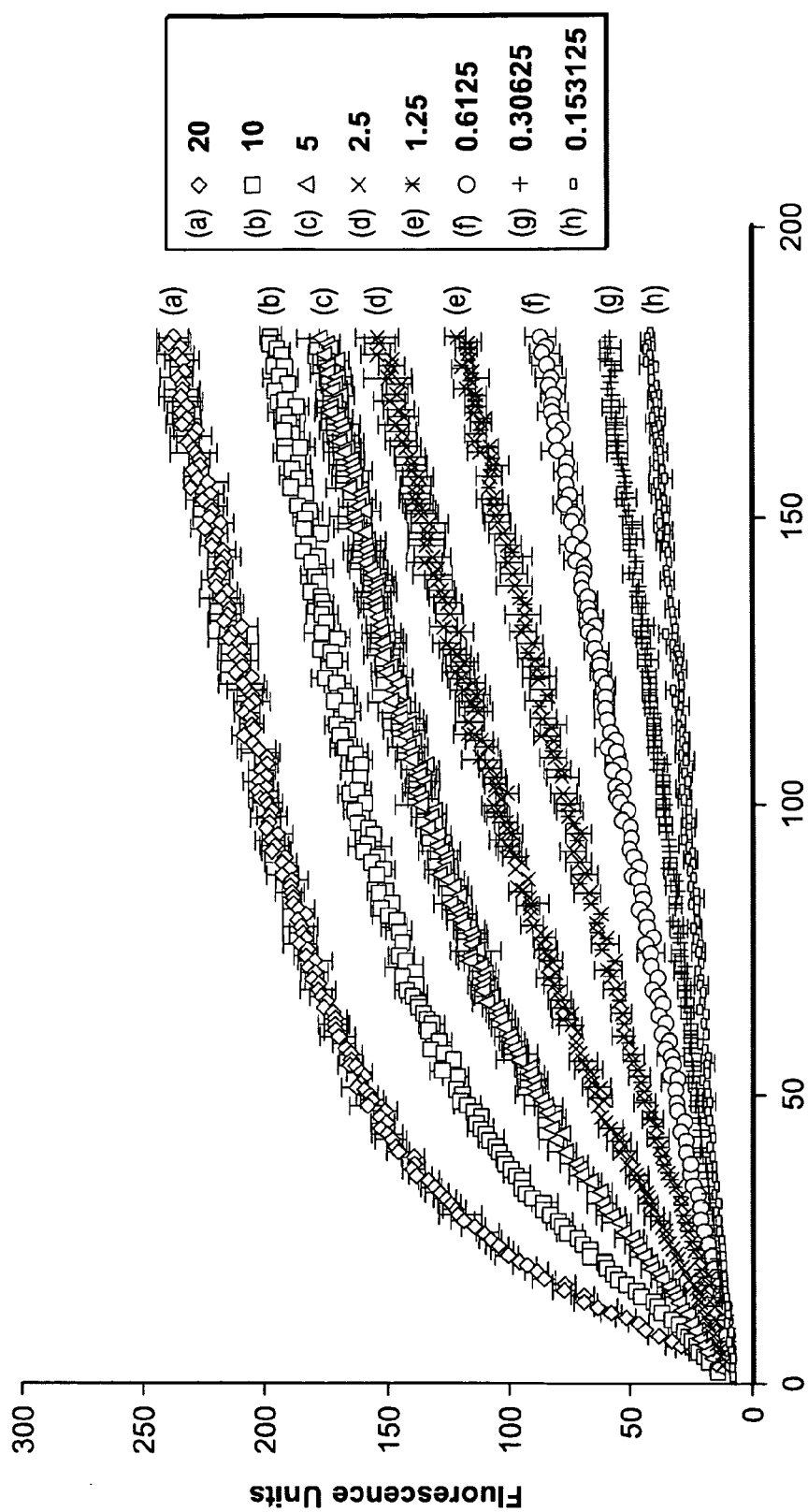
FIG. 9 shows the fluorescence emission of β-LEAPP incubated with different concentrations of *B. cereus* Penicillinase expressed as a function of time. The values listed in the chart legend are the concentrations of Penicillinase in units of enzyme per milliliter. Data is representative of three experimental repeats.
Figure 10:
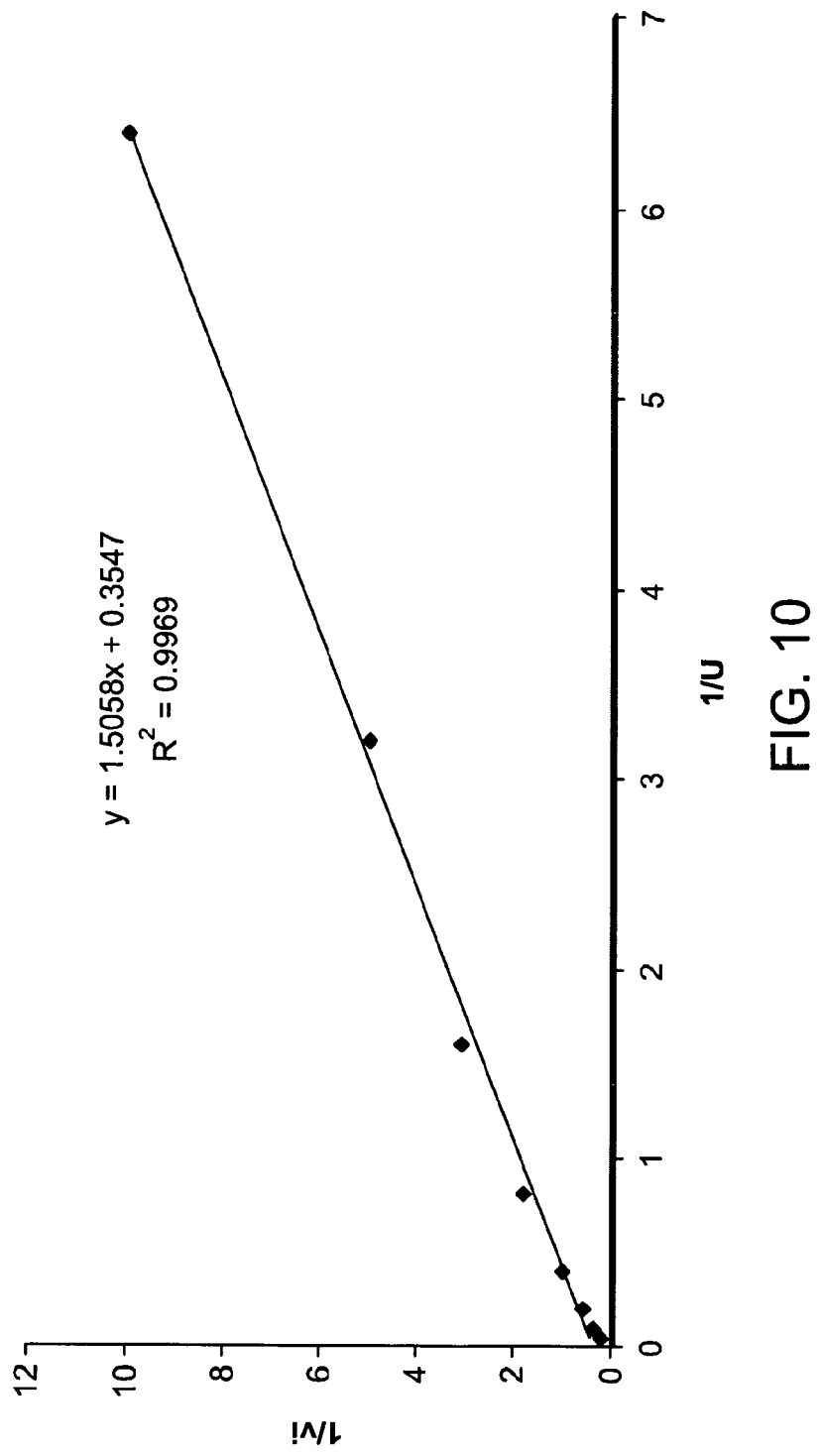
FIG. 10 shows the double reciprocal plot of the instantaneous velocity of the increase in β-LEAPP fluorescence as a function of the concentration of *B. cereus* Penicillinase. The instantaneous velocity was determined over the range of the first 20 readings taken over the first 20 minutes. Data consists of experimental repeats.

The ability of commercially available Penicillinase to hydrolyze the β-LEAPP substrate was characterized in FIG. 9. The plots of fluorescence units as a function of time demonstrate the dependence of β-LEAPP fluorescence on Penicillinase concentration. Within the first 20 minutes of incubation the slopes of all of the plots are significantly different from one another (see FIG. 9). From this data, a standard curve was generated (see FIG. 10) through plotting the reciprocal of the instantaneous velocity of the increase in β-LEAPP fluorescence (1/Vi) as a function of the reciprocal of the concentration of Penicillinase in units per milliliter (1/U*ml-1). The instantaneous velocity (Vi) is the rate of change in fluorescence within the region of the curve where the slope is linear. The linear region of the curve depends on the concentration of enzyme. For the generation of a standard curve for β-LEAPP fluorescence as a function of Penicillinase concentration the first 20 readings, taken over the first 20 minutes proved sufficient yielding an $R^2$ value of 0.9969 for the linear fit (see FIG. 10). The equation that corresponds to the linear trend line of the double reciprocal plot can be used to determine the beta-lactamase activity present in experimental samples where y equals the reciprocal of the Vi and x equals the reciprocal of U (see FIG. 10 and Table 1 below).

Figure 11A:
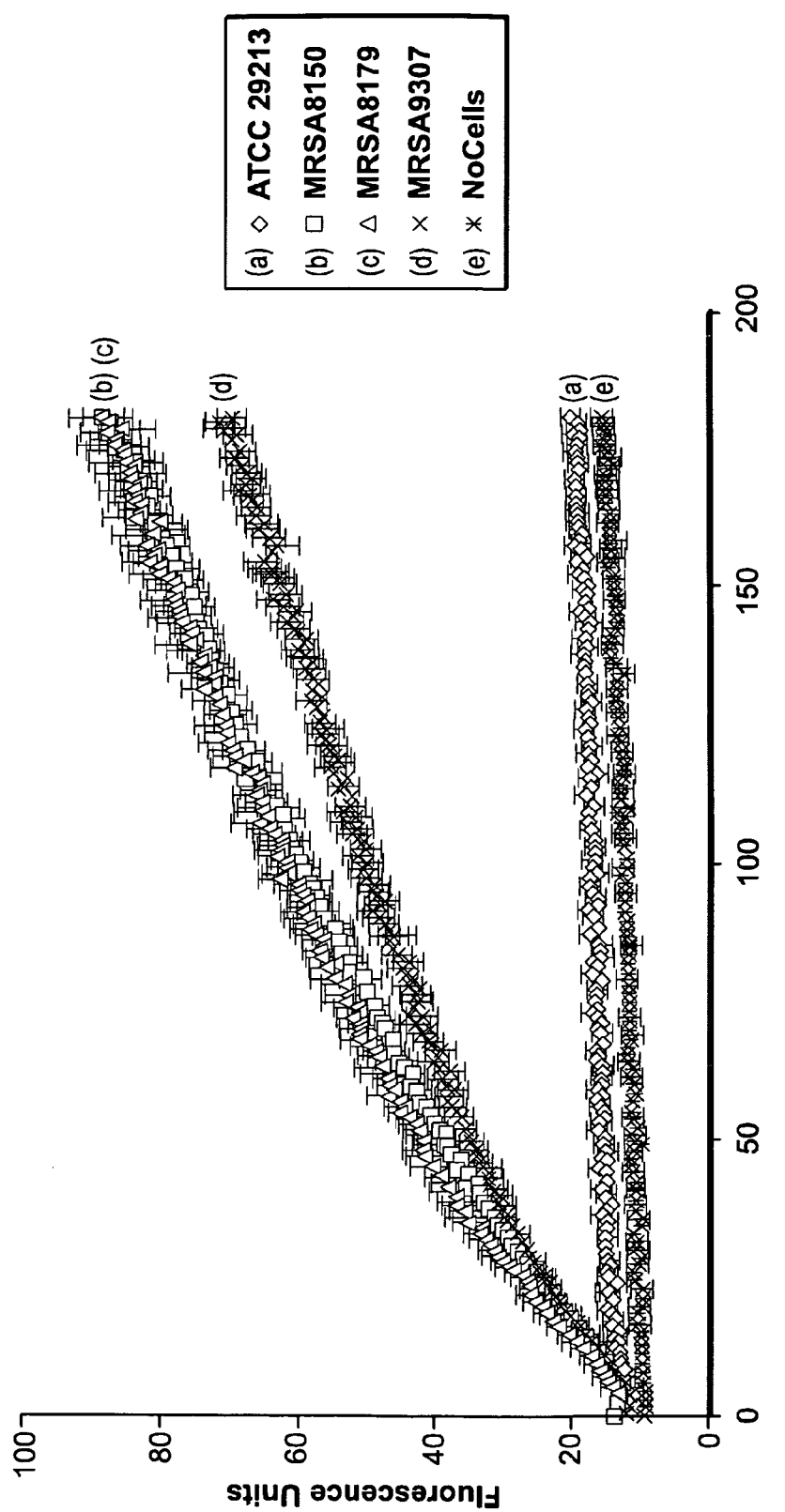
FIG. 11 shows the fluorescence emission of β-LEAPP produced in incubation with various strains of bacteria as a function of time. Graph A shows ATCC 29213 *S. aureus* beta-lactamase non-producer, MRSA 8150, 8179, 9307 (all clinical isolates and beta-lactamase producers), and a no-cell control. Gra "conservative variations." Variants of a peptide are typically characterized by possession of at least about 50% sequence identity counted over the full length alignment with the amino acid sequence of the peptide using the NCBI Blast 2.0, gapped blastp set to default parameters, more preferably about 60% or 70%, even more preferably about 80% or 90%, or even 95% or 99% sequence identity.
Figure 11B:
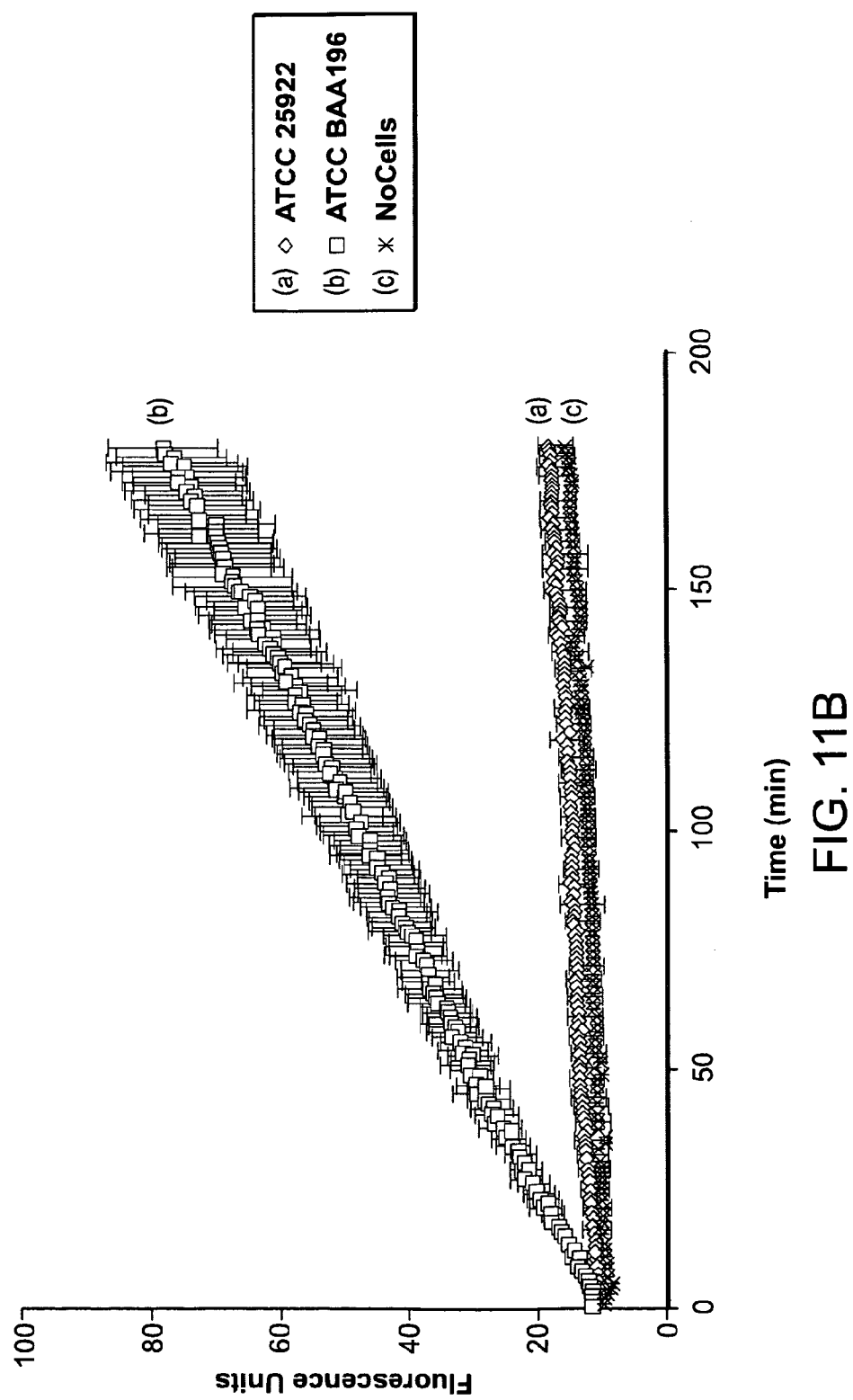

The ability of various strains of bacteria, beta-lactamase producers, betalactamase non-producers, Gram positive, and Gram negative, to hydrolyze β-LEAPP was determined under conditions identical to those used for the assay of the hydrolytic cleavage by Penicillinase (see FIGS. 11A and 11B). Beta-lactamase activity was detectable in cultures of both Gram positive and Gram negative bacteria. Only those bacterial strains that produced beta-lactamase resulted in an increase in fluorescence emission when in incubation with β-LEAPP (see FIGS. 11A and 11B).

The difference in the level of fluorescence emission produced by beta-lactamase producing and non-producing strains of bacteria is clear (as shown in FIGS. 11A and 11B). All of the beta-lactamase producing strains of MRSA and the ESBL producing strain of Escherichia coli showed a dramatic increase in fluorescence emission when compared to that produced by the beta-lactamase non-producing strains. The increase in fluorescence emission due to the incubation of β-LEAPP with the beta-lactamase non-producing bacteria was identical to that produced by reaction buffer alone indicating that the marginal increase was due the minor degradation of β-LEAPP when under the reaction conditions.

TABLE 1

The values of the instanteous velocity (Vi) of β-LEAPP fluorescence emission produced by various beta-lactamase producing bacteria were used to calculate the amount of beta-lactamase activity present in the bacterial cultures.

| Strain | Slope (m) or (Vi) | 1/Vi | 1/Units activity * ml$^{-1}$ | Units Activity/ml |
|---|---|---|---|---|
| MRSA 8179 | 0.635756 | 1.57293 | 0.811415 | 1.232415 |
| MRSA 8150 | 0.4423 | 2.260909 | 1.266883 | 0.789339 |
| MRSA 9307 | 0.466859 | 2.141973 | 1.188143 | 0.841649 |
| ATCC BAA196 | 0.338173 | 2.957069 | 1.727768 | 0.578782 |

Discussion

There are over 500 different beta-lactamases known and over 200 of them are extended-spectrum-beta-lactamases (ESBLs) (Paterson et al., Clin. Microbio. Rev. 2005, 18:657-686). Commercially available substrates for the detection of bacterial beta-lactamase produce a colorimetric change upon hydrolysis where the color of the substrate changes hue or intensity. The substrates nitrocefin and centa, for example, both exhibit a colorimetric change when hydrolyzed by beta-lactamase. The former, nitrocefin, is distributed in the form of impregnated paper discs. The application of a bacterial colony to a disc results in the development of a pink color. These prior known methods provide qualitative (yes/no) detection, but do not provide any information regarding the relative amount of enzymatic activity or any insight into the type of beta-lactamase activity. The amount of beta-lactamase activity and the substrate specificity of that activity are important considerations in determining the appropriate antibiotic therapy for patients suffering from drug resistant bacterial infections. The nitrocephin disk test alone does not provide sufficient information to determine the appropriate course of therapy in a clinical setting. Centa is distributed in the form of a powdered salt and also provides qualitative information, at a more reasonable cost, but requires the extended incubation of broth cultures for the development of color.

The enzymatic hydrolysis of β-LEAPP, in accordance with an embodiment of the present invention, results in an increase in fluorescence emission, thus providing a more sensitively detectable change than that of colorimetric substrates. This feature allows for the rapid quantification of enzyme activity and also has the potential for use in the identification of the substrate specificity of various beta-lactamase enzymes. The use of β-LEAPP for these purposes offers significant advantages not only for the researcher of bacterial beta-lactamase, but also for the clinical characterization beta-lactamase activity in that it provides more useful information. The researcher can determine the amount beta-lactamase activity and the substrate specificity of that activity simultaneously whereas the current commercially available substrates provide only a qualitative answer. The assay time to determine the amount of enzyme activity possessed by a particular strain of beta-lactamase producing bacteria can be within about 20 minutes or even less. Through the inclusion of various beta-lactams in the assay buffer one creates a competition between β-LEAPP and the beta-lactam for binding the active site of the enzyme. Through comparison of the fluorescence emission over time between the competitive and non-competitive reactions the researcher can determine whether or not a particular infectious bacteria is capable of hydrolyzing the competitor substrate. The use of β-LEAPP in a clinical diagnostic role could provide the research with the valuable information of whether or not the infectious bacteria has the capacity to hydrolyze extended spectrum cephalosporins in a relatively short amount of time. This information is critical for the clinician to determine the appropriate course of antibiotic therapy and could result in improved patient outcomes through reducing the amount of time required for such evaluations.

Example 4. Synthesis of β-LEAPP

This example describes the synthesis of a photosensitizer composition ("β-LEAPP") comprising two EtNBS molecules conjugated to cephalosporin, a substrate molecule for beta-lactamase (see FIG. 8).

Rationale

The photosensitivity of phenothiazine is advantageously quenched until released from the cephalosporin linked quencher in the presence of β-lactamase. Two quenching mechanisms are widely acknowledged. One is static (ground-state) quenching, achieved by homo- or hetero-fluorophore dimerization. The other is dynamic (excited-state) quenching, achievable by Forster resonance energy transfer (FRET). In this example, the photosensitizer composition, β-LEAPP, was synthesized using a static quenching mechanism. However, the same design can also be easily adapted to FRET quenching.

Homo-dimerization (PS-PS pair) was advantageous in this example over hetero-dimerization (PS-quencher pair) for at least the following two reasons: 1) it is readily synthesized; 2) cleavage of each prodrug (β-LEAPP) will generate two PSs therefore in theory can achieve twice the phototoxicity and/or fluorescence signaling.

The photosensitizing component in β-LEAPP (also referred to herein as "prodrug 2") is 5-(4'-carboxybutylamino)-9-diethylaminobenzo[a]phenothiazine (EtNBS-COOH), which was developed by the inventors and was shown to have excellent photosensitizing efficacy. The terminal carboxyl group with the flexible alkyl chain provides an ideal site for conjugation. 7-amino-3-chloromethyl-3-cephem-4-carboxylic acid p-methoxybenzyl ester (ACLE, commercial available) is used as cephalosporin scaffold. ACLE is a common starting material to synthesize cephalosporin derivatives. It integrates an amino group at 7-position. By replacing chlorine at 3'-position with 4-aminothiophenol provides an additional amino group therefore each ACLE molecule can accommodate two EtNBS-COOH molecules to form a static quenching pair.

Instrumentation $^1$H and $^{13}$C-NMR were recorded on Varian 400 MHz instrument, using 15-20 mg of material in CDCl3 or DMSO-d6 as solvents. ESI mass spectra were recorded with a Bruker Daltonics Esquire 3000 plus spectrometer. UV-visible absorption spectra were recorded using a Hewlett Packard 8453 spectrophotometer equipped with a diode array detector system. Fluorescence spectra were obtained in aqueous/organic solutions of products using Jobin Yvon Horiba FluoroMax-3 fluorometer. HPLC analysis were performed using Shimadzu VP series of SCL 10A controller, SPD-M10A diode array detector, LC-LOAD pumps, DGU-14A degasser and C18 reverse phase column controlled by Class VP software.

Synthesis and Characterization of β-LEAPP

Commercially available ACLE is a hydrochloride salt. Mild base as used to treat the ACLE, resulting in the freeing of the amino group at 7-position which is readily undergoing acylation. The chlorine at 3'-position of ACLE was displaced by 4-aminothiophenol. As an excellent leaving group, the thiophenol residue facilitated the fragmentation after β-lactamase hydrolysis, and the amino group on thiophenol introduced an additional coupling site. EtNBS-COOH was coupled to both 7- and 3'-amino in the presence of O-(7-Azabenzotriazole-1-yl)-N,N,N,N'-tetramethyluronium hexafluorophosphate (HATU) as coupling reagent. A subsequent treatment with TFA in the presence of anisole gave unprotected prodrug 2 in excellent yield. Purification of prodrug was carried on RP-HPLC. Characterization of prodrug 2 used NMR spectroscopy and mass spectrometry.

Quenching Phenomena

The concentration of constituents in prodrug conjugates was routinely scanned by absorption spectroscopy (between 200 nm and 800 nm) on dilute equimolar solutions of starting materials (EtNBS-COOH and ACLE) and synthesized prodrug. Fluorescence quenching phenomena in prodrug with respect to EtNBS-COOH was demonstrated using fluorescence emission experiments. Equimolar solutions of EtNBS-COOH and prodrug were compared at 655 nm excitation with emissions scanned in the range of 655 nm to 800 nm.

Lactamase Controlled Photosensitizer Release

Two commercial enzymes, a β-lactamase from *Enterobacter cloacae* and a penicillinase from *Bacillus cereus* were used to demonstrate release and dequenching. For this study, solutions of prodrugs were treated with required units of both enzymes. Time dependent fluorescence emission, indicating release of photosensitizer from conjugate, will be recorded and compared to free photosensitizer. Released photosensitizer will further be analyzed for its photosensitivity using Invitrogen's reactive oxygen species detection kit (Posner et al., Biochem. Biophys. Res. Commun., 1984, 123:869-873; Thompson et al., Methods Enzymol., 1986, 133:569-584; Li et al., J. Biol. Chem., 1998, 283:2015-2023) or using dihydroethidium as an oxidizing probe (Dolgachev et al., Biochem. Biophys. Res. Commun., 2005, 332:411-417).

Results Anticipated

It is anticipate that β-LEAPP will achieve satisfied yield at more than 95% purity. Due to very short distance between two photosensitizers, high quenching efficiency is anticipated. β-LEAPP is also anticipated to show efficient recovery in excited state properties (such as fluorescence, singlet oxygen yield, cytotoxic effect) upon enzymatic cleavage/photosensitizer release.

Example 4. (Prophetic) Use of β-LEAPP to Determine Substrate Specificity of a Beta-Lactamase Activity of a Sample The following example describes how to determine the specificity of a given beta-lactamase enzyme.

Methods

Any suitable multiwell optically transparent plate i.e. 96 well culture plate can be used according to this example to carry out the reactions to determine enzyme substrate specificity. A useful configuration is described in FIG. 12.

Set-up: "Criss-Cross Serial Dilution"

Serial concentrations of β-LEAPP are made from left to right across the plate or from top to bottom across the plate. Serial concentrations of Competitor Substrates are deposited from left to right across the plate or from top to bottom across the plate: These preferably include all beta-lactam antibiotics. Serial concentrations of Beta-lactamase inhibitors from left to right across the plate or from top to bottom across the plate: These include clavulanic acid, sulbactam, and tazobactam Add Sample and Monitor Fluorescence:

The rate of fluorescence emission change as a function of time for each experimental condition would be compared and the specificity of the enzyme would be determined.

Example 5. Use of β-LEAPP to Determine β-Lactamase Functionality in a Competitive Substrate Inhibition Assay Due to overlapping and similar characteristics of many beta-lactamases, it has become important and critical to the development of appropriate antibiotic regimens to have a means of distinguishing between different beta-lactamases associated with infectious bacterial agents, e.g., multi-drug resistant *S. aureus*. It is well established that beta-lactamases can be characterized by their interactions with inhibitors and substrates (see *Molecular Bacteriology: protocols and clinical applications*, Ed. Woodford et al., Humana Press 1998, Chapter 26: Biochemical and Enzyme Kinetic Applications for the Characterization of β-lactamases, David J. Payne and Tony H. Farmer, pp. 513-537, incorporated herein by reference). For example, beta-lactamases can be characterized based on their rates of hydrolysis of different beta-lactam substrates (e.g., penicillin, ampicillin, etc.) at fixed concentrations or based on determining the $I_{50}$ (the concentration of an inhibitor that inhibits the hydrolytic activity of a beta-lactamase by 50% compared with a control).

Other known methods relate to determining the susceptibility (e.g., Minimum Inhibitory Concentrations—MIC) of bacteria to individual beta-lactams, followed by determining their susceptibility to combinations of beta-lactams (as recommended by the Clinical Laboratory Institute). Such an approach involves and, in fact, requires bacterial growth, and, thus, requires at least about 20 hours to achieve reliable results. This type of approach is further described in Farber et al., 2008, "Extended-spectrum Beta-lactamase detection with different panels for automated susceptibility testing and with a chromogenic medium," J Clin Microbiol 46:3721-7 and Spanu et al., 2006, "Evaluation of the new VITEK 2 extended-spectrum beta-lactamase (ESBL) test for rapid detection of ESBL production in Enterobacteriaceae isolates," J Clin Microbiol, 44:3257-62, each of which are incorporated herein by reference.

Due to the fact that many of the standard techniques for characterizing beta-lactamases are typically slow and/or require bacterial growth, methods that are sensitive, rapid and easy to use would be desirable.

This Example describes a new methodology for use in characterizing beta-lactamases by using a competitive substrate inhibition assay. It is believed that no competitive substrate inhibition assays for determining beta-lactamase functionality are currently in use by clinical microbiology laboratories. This new approach is based on exploiting the sensitivity and mechanism of the β-LEAP compound of the invention. More in particular, this approach is based on measuring the level of induced-fluorescence caused by the cleavage/hydrolysis and consequent activation of the β-LEAP compound by beta-lactamase enzymes under evaluation while also in the presence of, or "in competition" with, different types and amounts of beta-lactamase enzyme substrates. The degree of inhibition of β-LEAP hydrolysis/ fluorescence due to competition with the beta-lactam competitor substrates is determined, which provides the basis for determining beta-lactamase functionality.

Methods for making the β-LEAP of the invention and its quenching/activation properties are described elsewhere in this application (e.g., see Example 3) and by the inventors in Zheng et al., 2009, "Exploiting a bacterial drug-resistance mechanism: a light-activated construct for the destruction of MRSA," Angew Chem Int Ed Engl, 48:2148-51, which is incorporated herein be reference in its entirety.)

Figure 13C:
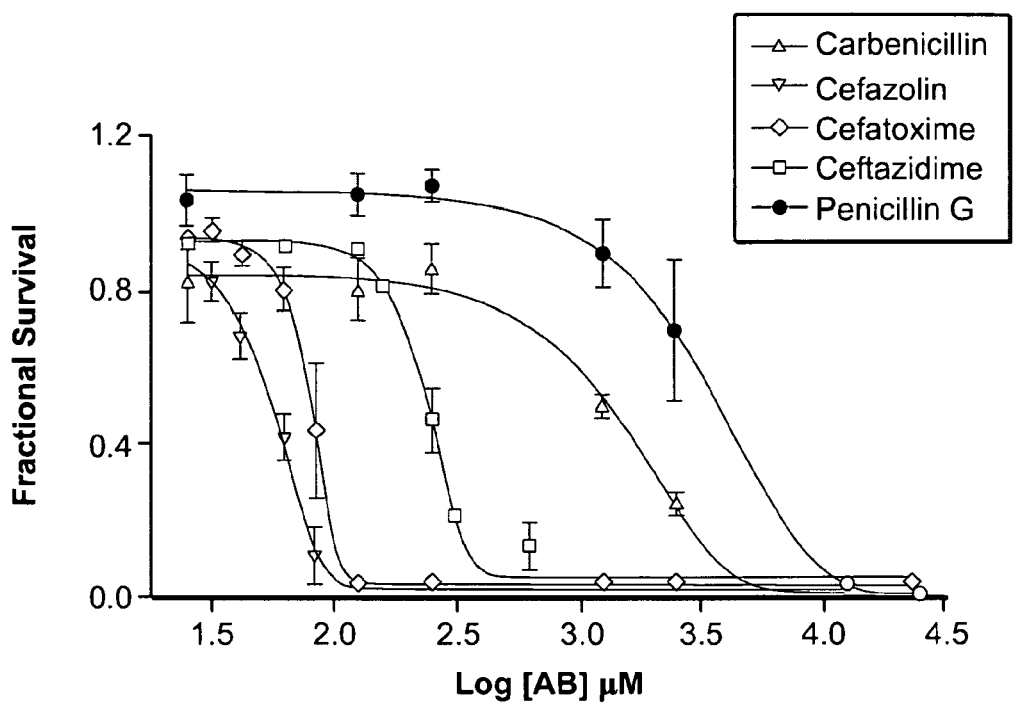

This approach involved combining in a 384 multi-well assay plate format purified B. cereus beta-lactamase or bacterial suspensions with the β-LEAP of the invention and a competitive beta-lactam substrate, including amoxicillin, clavulanic acid, ampicillin, penicillin G, carbenicillin, cefazolin, cefotaxime or ceftazidime. For both purified B. cereus beta-lactamase enzyme and whole bacteria suspensions, the cephalosporins (ceftazidime, cefotaxime, and cephalothin) were more effective inhibitors of β-LEAP hydrolysis/fluorescence than were the penicillins (amoxicillin, ampicilin, penicillin G, and carbenicillin) (FIG. 13a, which shows the inhibition constants (Ki) of a panel of beta-lactams for the competitive substrate inhibition of β-LEAP hydrolysis by B. cereus beta-lactamase; and FIG. 13b, which shows the inhibition constants (Ki) of a panel of beta-lactams for the competitive substrate inhibition of β-LEAP hydrolysis by bacterial suspensions). These results correlate with those obtained using a conventional MIC (Minimum Inhibitory Concentration) assay (see FIG. 13d, which shows the MICs of a panel of beta-lactams for B. cereus) and provided more useful information. Importantly, the inhibitory effects of ampicillin and amoxicillin on β-LEAP hydrolysis were detected using a the β-LEAP competitive inhibition assay; however, neither ampicillin nor amoxicillin resulted in any in vitro growth inhibition (FIG. 13d, no inhibition by amoxicillin, clavulanic acid or ampillin, data not shown).

These results indicate that β-LEAP may be used to identify the functionality of β-lactamase enzymes even where assays that rely on bacterial growth cannot. Accordingly, the competitive inhibition assay based on inhibition of β-LEAP hydrolysis (i.e., decreased fluorescence) is a sensitive and rapid manner relative to previously known methods, e.g., MIC methods, by which to characterize the functionality of a given beta-lactamase enzyme from either a purified source or from a sample bacterial suspension.

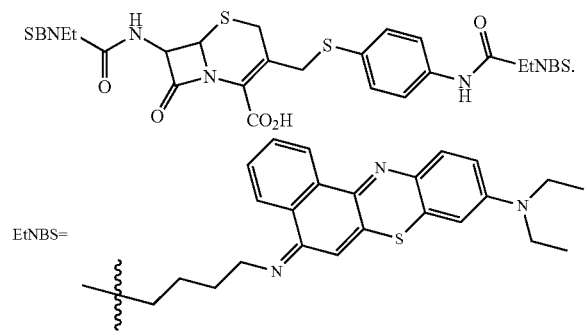

What is claimed is:

1. A method of measuring susceptibility of beta-lactamase secreting bacteria in a sample to a beta-lactam antibiotic, wherein, the method comprises:
   (a) contacting the sample with:
      (i) a composition comprising a cephalosporin linker compound linked with two benzophenothiazinium chloride (EtNBS) fluorophores (standard); and
      (ii) a composition comprising the beta-lactam antibiotic and the cephalosporin linker compound linked with two EtNBS fluorophores (test sample),
   wherein, the EtNBS fluorophores are (Z)-5-((9-(diethylamino)-5H-benzo[a]phenothiazin-5-ylidene)amino) pentanoic acid (EtNBS-COOH) derived fluorophores;
   (b) light-activating the standard and the test compositions to produce a fluorescence signal;
   (c) quantifying the fluorescence signal with a detector to obtain result;
   (d) comparing the test result to the standard result; and
   (e) if the amount of the measured fluorescence in the test sample is less than the amount of measured fluorescence in the standard sample, then the β-lactamase secreting bacteria is determined to be susceptible to the β-lactam antibiotic.

2. The method of claim 1, wherein, the EtNBS fluorophores are conjugated to the cephalosporin linker via amide bond.

3. The method of claim 2, wherein at least one fluorophore is bound at the 3' position of the cephalosporin linker.

4. The method of claim 3, wherein, the cephalosporin linker compound linked with two EtNBS fluorophores is a compound of the structure:

UNITED STATES PATENT AND TRADEMARK OFFICE
CERTIFICATE OF CORRECTION

PATENT NO.        : 9,828,622 B2
APPLICATION NO.   : 12/990997
DATED             : November 28, 2017
INVENTOR(S)       : Tayyaba Hasan et al.

Page 1 of 2

It is certified that error appears in the above-identified patent and that said Letters Patent is hereby corrected as shown below:

In the Specification

In Column 1, Line 10 (approx.), delete "Sera" and insert -- Ser.--;

In the Claims

In Column 70, Lines 20-42, Claim 1 delete
"1. A method of measuring susceptibility of beta-lactamase secreting bacteria in a sample to a beta-lactam antibiotic, wherein, the method comprises:
    (a) contacting the sample with:
    (i) a composition comprising a cephalosporin linker compound linked with two benzophenothiazinium chloride (EtNBS) fluorophores (standard); and
    (ii) a composition comprising the beta-lactam antibiotic and the cephalosporin linker compound linked with two EtNBS fluorophores (test sample),
    Wherein, the EtNBS fluorophores are (Z)-5-((9-(diethyl-amino)-5H-benzo[a]phenothiazine-5-ylidene)amino)pentanoic acid (EtNBS-COOH) derived fluorophores;
    (b) light-activating the standard and the test compositions to produce a fluorescence signal;
    (c) quantifying the fluorescence signal with a detector to obtain result;
    (d) comparing the test result to the standard result; and
    (e) if the amount of the measured fluorescence in the test sample is less than the amount of measured fluorescence in the standard sample, then the β-lactamase secreting bacteria is determined to be susceptible to the β-lactam antibiotic." and insert
-- 1. A method of measuring susceptibility of beta-lactamase secreting bacteria in a sample to a beta-lactam antibiotic, wherein, the method comprises:
    (a) contacting the sample with a composition comprising the beta-lactam antibiotic and a cephalosporin linker compound linked with two EtNBS fluorophores, wherein: (i) the linker comprises a cleavage site for a beta-lactamase that competes for binding to the beta-lactamase with the beta-lactam antibiotic; (ii) the fluorophores are in a static quenched state before contact with the sample; and (iii) the EtNBS fluorophores are (Z)-5-((9-(diethylamino)-5H-benzo[a]phenothiazin-5-ylidene)amino)pentanoic acid (EtNBS-COOH) derived fluorophores;

Signed and Sealed this
Sixth Day of March, 2018

Andrei Iancu
*Director of the United States Patent and Trademark Office*

(b) maintaining the sample for a time and under conditions sufficient for cleaving the linker to dequench the fluorophores;
  (c) light-activating the composition to produce a fluorescence signal; and
  (d) quantifying the fluorescence signal with a detector to obtain a measurement. --.